(12) United States Patent
Kawano

(10) Patent No.: US 8,568,296 B2
(45) Date of Patent: Oct. 29, 2013

(54) IN-VIVO OBSERVING SYSTEM AND IN-VIVO OBSERVING METHOD

(75) Inventor: Hironao Kawano, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 758 days.

(21) Appl. No.: 12/704,908

(22) Filed: Feb. 12, 2010

(65) Prior Publication Data

US 2010/0198008 A1    Aug. 5, 2010

Related U.S. Application Data

(63) Continuation of application No. PCT/JP2008/064350, filed on Aug. 8, 2008.

(30) Foreign Application Priority Data

Aug. 13, 2007    (JP) .................................. 2007-211124

(51) Int. Cl.
*A61B 1/04* (2006.01)

(52) U.S. Cl.
USPC ............................ 600/109; 600/117; 600/118

(58) Field of Classification Search
USPC ......................................... 600/109, 117, 118
See application file for complete search history.

(56) References Cited

U.S. PATENT DOCUMENTS

| | | | |
|---|---|---|---|
| 7,697,970 B2 * | 4/2010 | Uchiyama et al. ............ | 600/407 |
| 2001/0055462 A1 * | 12/2001 | Seibel ........................... | 385/147 |
| 2006/0256191 A1 | 11/2006 | Iketani et al. | |
| 2007/0299301 A1 * | 12/2007 | Uchiyama et al. ............ | 600/101 |
| 2008/0300453 A1 * | 12/2008 | Aoki et al. ..................... | 600/103 |
| 2008/0306340 A1 * | 12/2008 | Uchiyama et al. ............ | 600/117 |

FOREIGN PATENT DOCUMENTS

| | | |
|---|---|---|
| JP | 2002-191547 | 7/2002 |
| JP | 2006-068501 | 3/2006 |
| JP | 2006-314680 | 11/2006 |
| JP | 2006-527012 | 11/2006 |
| JP | 2007-159641 | 6/2007 |
| JP | 2007159641 A * | 6/2007 |

OTHER PUBLICATIONS

Abstract of International Publication No. WO 2004/096008 A2, dated Nov. 11, 2004.
International Search Report dated Nov. 11, 2008.

* cited by examiner

*Primary Examiner* — Clayton E. LaBalle
*Assistant Examiner* — Linda B Smith
(74) *Attorney, Agent, or Firm* — Scully, Scott, Murphy & Presser, P.C.

(57) ABSTRACT

An in-vivo observing system for observing inside of a subject includes an illuminating unit configured to illuminate inside of the subject by illumination light; an imaging unit configured to sequentially capture in-vivo images of the subject illuminated by the illumination light; a direction change unit configured to change an image capturing direction of the imaging unit; and a control unit configured to control the direction change unit to set an angular difference in the imaging capturing direction less than an angle of view of the imaging unit when the imaging unit captures two continuous in-vivo images while causing the direction change unit to change the image capturing direction.

17 Claims, 23 Drawing Sheets

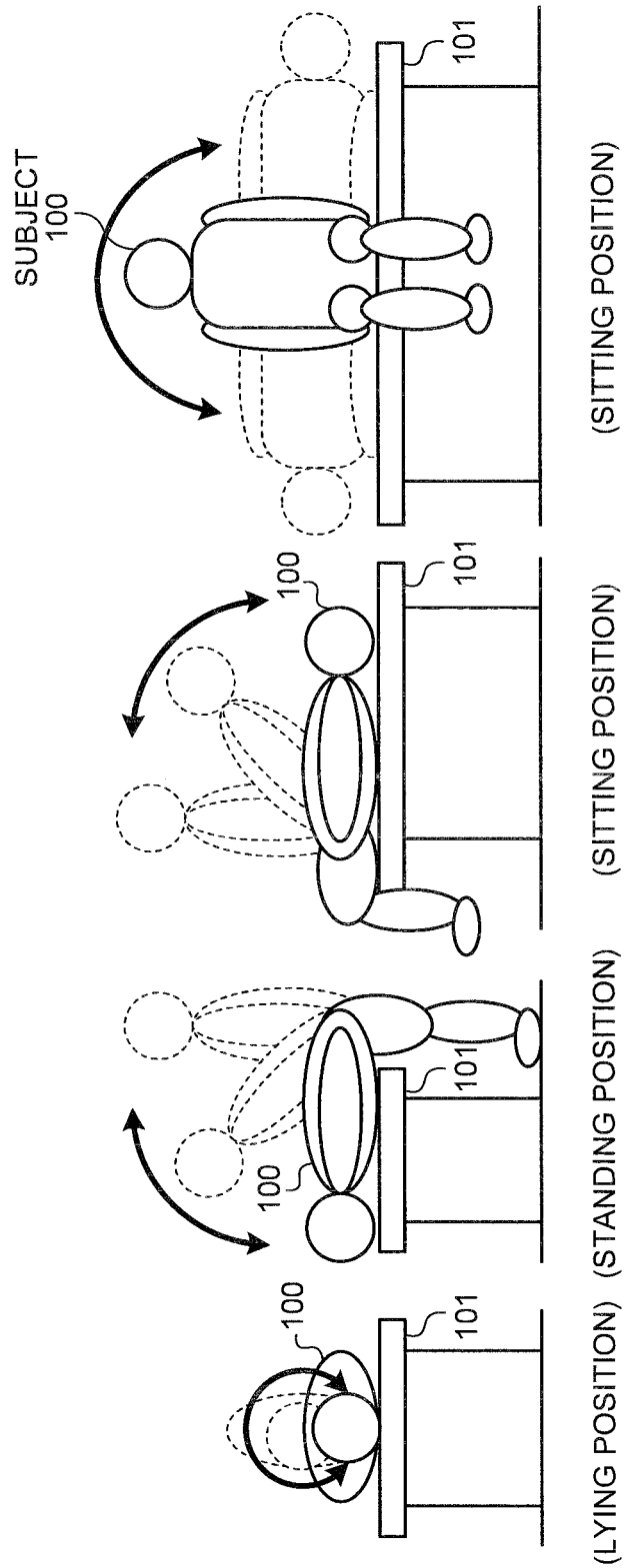

IN-VIVO OBSERVING SYSTEM AND IN-VIVO OBSERVING METHOD

CROSS-REFERENCE TO RELATED APPLICATIONS

This application is a continuation of PCT international application Ser. No. PCT/JP2008/064350 filed on Aug. 8, 2008 which designates the United States, incorporated herein by reference, and which claims the benefit of priority from Japanese Patent Applications No. 2007-211124, filed on Aug. 13, 2007, incorporated herein by reference.

BACKGROUND OF THE INVENTION

1. Field of the Invention

The invention relates to an in-vivo observing system and an in-vivo observing method for observing inside of an organ of a subject such as a patient.

2. Description of the Related Art

Conventionally, in a field of an endoscope, there are capsule endoscopes which are introduced into an organ of a subject to capture an image (hereinafter, called also an in-vivo image) inside of the organ. The capsule endoscope includes an imaging function and a radio communication function in a capsule casing and functions as an in-vivo image acquisition device for obtaining a group of in-vivo images of a subject. The capsule endoscope is swallowed through a mouth of a subject such as a patient, then sequentially captures in-vivo images of the subject while moving in a gastrointestinal tract by a peristaltic movement and the like during a period until it is naturally discharged to the outside of the subject and sequentially wirelessly transmits the captured in-vivo images to a receiving device outside of the subject.

The receiving device is carried by the subject, receives a group of in-vivo images from the capsule endoscope in the subject, and accumulates the received group of the in-vivo images to a detachable storage medium. The storage medium in which the group of the in-vivo images is accumulated is removed from the receiving device and inserted into a predetermined image display device. The image display device obtains the group of the in-vivo images of the subject through the storage medium and displays the group of the in-vivo images of the subject on a display. A user such as a doctor and a nurse examines inside of an organ of the subject by observing the in-vivo images displayed on the image display device and diagnoses the subject.

Further, there are recently proposed magnetic guide systems for guiding a capsule endoscope in a subject by a magnetic force (refer to, for example, Japanese Laid-open Patent Publication No. 2006-68501). In the magnetic guide systems, the capsule endoscope additionally includes a magnet magnetized in a longitudinal direction of a capsule casing in addition to the imaging function and the radio communication function described above and is guided by an external magnetic field formed by a magnetic field generating device outside of the subject. An image capturing direction of the capsule endoscope is controlled by the external magnetic field of the magnetic field generating device, and the capsule endoscope captures a group of in-vivo images inside of an organ of the subject while changing the image capturing direction in the organ.

However, when the capsule endoscope in a subject is caused to time-sequentially capture a group of in-vivo images while changing the image capturing direction thereof as described above by the external magnetic field, there is a possibility that a group of discontinuous in-vivo images in which overlapping image portions do not exist between the in-vivo images adjacent to each other in time, are captured. More specifically, there is a possibility that out-of-capture portions, which are not captured by the capsule endoscope, exist in an organ in which a group of in-vivo images is captured. As a result, it becomes difficult to observe (examine) inside of an organ of a subject without remaining uncaptured portions.

SUMMARY OF THE INVENTION

An in-vivo observing system for observing inside of a subject according to an aspect of the present invention includes an illuminating unit configured to illuminate inside of the subject by illumination light; an imaging unit configured to sequentially capture in-vivo images of the subject illuminated by the illumination light; a direction change unit configured to change an image capturing direction of the imaging unit; and a control unit configured to control the direction change unit to set an angular difference in the imaging capturing direction less than an angle of view of the imaging unit when the imaging unit captures two continuous in-vivo images while causing the direction change unit to change the image capturing direction.

An in-vivo observing method according to an another aspect of the present invention is for observing inside of an organ of a subject by observing in-vivo images of the subject captured by an in-vivo image acquisition device introduced into the organ of the subject. The method includes a first image capturing step of capturing a first in-vivo image of the subject by the in-vivo image acquisition device; an image capturing direction change step of changing an image capturing direction of the in-vivo image acquisition device; and a second image capturing step of capturing a second in-vivo image of the subject by the in-vivo image acquisition device whose image capturing direction has been changed at the image capturing direction change step. At the image capturing direction change step, the image capturing direction of the in-vivo image acquisition device is changed so that the first in-vivo image and the second in-vivo image have image portions overlapping each other.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 25 is a schematic view exemplifying a state in which an image capturing direction of the capsule endoscope is changed by changing a body position of a subject.

DETAILED DESCRIPTION OF THE PREFERRED EMBODIMENTS

Figure 1:
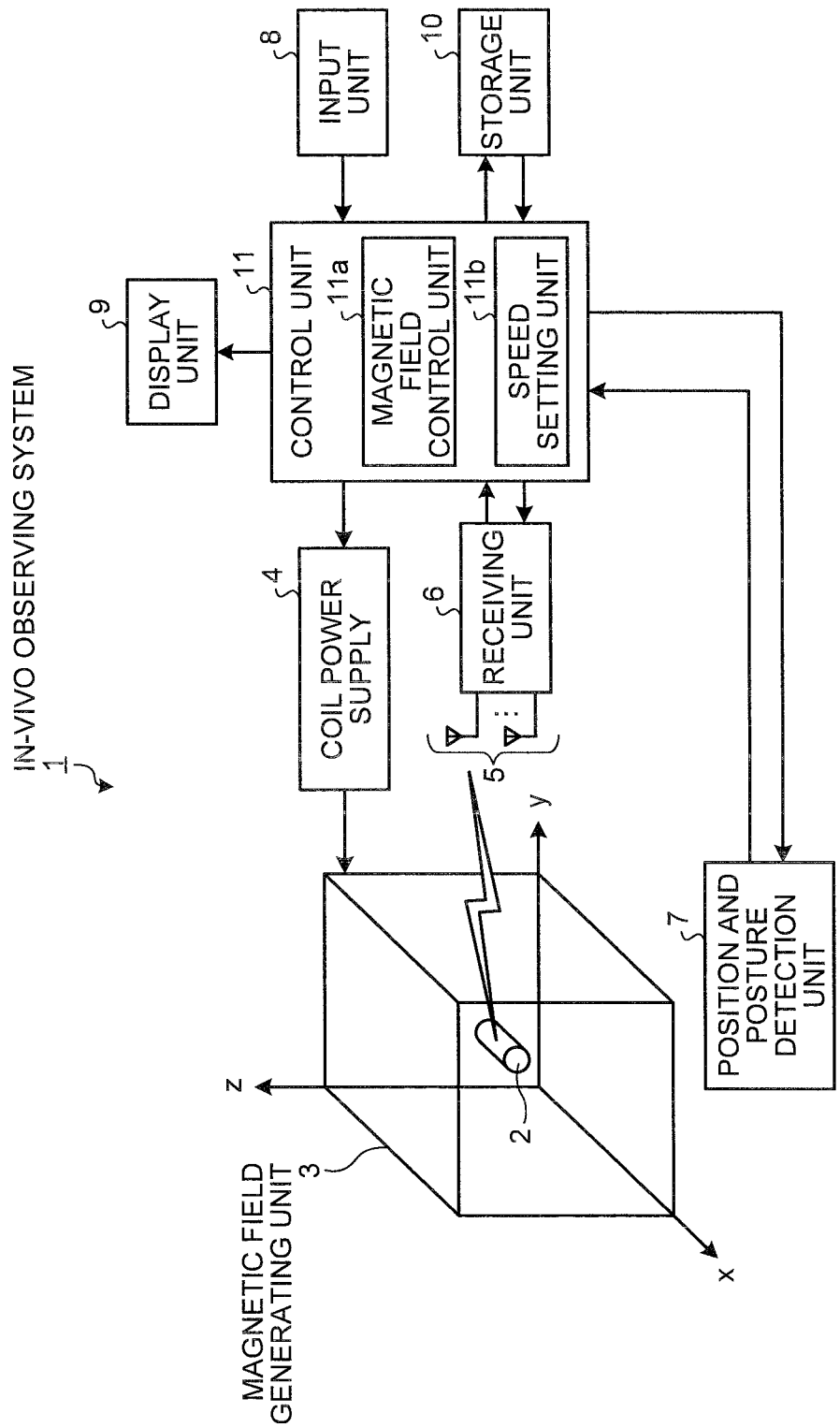
FIG. 1 is a block diagram schematically showing an arrangement example of an in-vivo observing system according to a first embodiment of the invention.

Preferred embodiments of an in-vivo observing system and an in-vivo observing method according to the invention will be explained below in detail referring to the drawings. Note that the invention is by no means limited by the embodiments.

First Embodiment

FIG. 1 is a block diagram schematically showing an arrangement example of an in-vivo observing system according to a first embodiment of the invention. As shown in FIG. 1, an in-vivo observing system 1 according to the first embodiment includes a capsule endoscope 2, which is introduced into an organ of a subject (not shown) such as a patient, a magnetic field generating unit 3, which generates an external magnetic field to magnetically guide the capsule endoscope 2 in the subject, and a coil power supply 4 which supplies a current to a coil (electromagnet) of the magnetic field generating unit 3. The in-vivo observing system 1 includes a plurality of receiving antennas 5 disposed on a body surface of the subject, a receiving unit 6 for receiving an image signal from the capsule endoscope 2 through the receiving antennas 5, and a position and posture detection unit 7 for detecting a present position and a present posture of the capsule endoscope 2 in the subject. Further, the in-vivo observing system 1 includes an input unit 8 for receiving various kinds of information, a display unit 9 for displaying various kinds of information of an in-vivo image and the like of the subject, a storage unit 10 for storing therein the various kinds of information, and a control unit 11 for controlling the respective components of the in-vivo observing system 1.

The capsule endoscope 2 is an example of an in-vivo image acquisition device for obtaining a group of in-vivo images of the subject and has an imaging function for capturing in-vivo images of the subject and a radio communication function for wirelessly transmitting the in-vivo images captured by the imaging function to the outside of the subject. Specifically, the capsule endoscope 2 is introduced into an organ of the subject such as a patient and moves in an organ of the subject by a peristaltic movement and the like. The capsule endoscope 2 sequentially obtains in-vivo images of the subject during a period until it is naturally discharged to the outside of the subject and sequentially wirelessly transmits an image signal including the obtained in-vivo images to the receiving unit 6 outside of the subject. Further, the capsule endoscope 2 contains magnetic substances such as permanent magnets or electromagnets (hereinafter, simply called magnets) and is guided by external magnetic fields formed by the magnetic field generating unit 3 from outside of the subject. A detailed arrangement of the capsule endoscope 2 will be described later.

The magnetic field generating unit 3 is realized by combining the electromagnets such as Helmholtz coils and generates magnetic fields (external magnetic fields) which can guide the capsule endoscope 2 in the subject. Specifically, the magnetic field generating unit 3 is prescribed by a three-axis orthogonal coordinate system having three orthogonal axes (x-axis, y-axis, z-axis) (hereinafter, called an xyz coordinate system) and generates magnetic fields of a desired intensity to respective axis directions (x-axis, y-axis, and z-axis directions) of the xyz coordinate system, respectively. A subject (not shown), who is placed on, for example, a bed and the like, is positioned in a space (i.e., a space surrounded by the electromagnets of the magnetic field generating unit 3) of the xyz coordinate system, and the magnetic field generating unit 3 applies the external magnetic fields which are formed by magnetic fields in the respective axis directions of the xyz coordinate system, i.e., three-dimensional rotating magnetic fields or three-dimensional gradient magnetic fields to the capsule endoscope 2 (more specifically, a magnet 28 to be described later) in the subject. The magnetic field generating unit 3 guides (offsets) the capsule endoscope 2 in the subject to a desired position by a magnetic attracting force or a magnetic repulsive force of the external magnetic fields.

Further, the magnetic field generating unit 3 acts as a direction change unit for changing an image capturing direction of the capsule endoscope 2 in the subject. Specifically, the magnetic field generating unit 3 changes a posture of the capsule endoscope 2 in the subject, i.e., a relative direction of the capsule endoscope 2 to the subject by changing the magnetic field directions of the external magnetic fields described above. With this operation, the magnetic field generating unit 3 changes the image capturing direction of the capsule endoscope 2 in the subject (more specifically, the image capturing direction of an imaging unit 23 to be described later). The magnetic fields in the respective axis directions of the xyz coordinate system (i.e., the external magnetic fields such as the rotating magnetic fields, the gradient magnetic fields, and the like) generated by the magnetic field generating unit 3 are controlled by an alternating current supplied from the coil power supply 4 (an amount of the current supplied from the coil power supply 4).

Although the xyz coordinate system may be the three-axis orthogonal coordinate system prescribed to the magnetic field generating unit 3 (that is, fixed to the magnetic field generating unit 3) as described above, it may be a three-axis orthogonal coordinate system fixed to a subject (not shown) including the capsule endoscope 2 in an organ or may be a three-axis orthogonal coordinate system fixed to a bed (not shown) on which the subject is placed.

The coil power supply 4 is used to supply the current to the magnetic field generating unit 3 to generate the external magnetic fields applied to the capsule endoscope 2 in the subject. The coil power supply 4 supplies the alternating current to the electromagnets of the magnetic field generating unit 3 based on a control of the control unit 11 and generates the magnetic fields in the respective axis directions of the xyz coordinate system described above.

The receiving antennas 5 are used to capture radio signals from the capsule endoscope 2 introduced into the subject. Specifically, the receiving antennas 5 are dispersingly disposed on a body surface of the subject into the organ of which the capsule endoscope 2 described above is introduced and capture the radio signals from the capsule endoscope 2 passing through inside of the organ. The receiving antennas 5 send the radio signals from the capsule endoscope 2 to the receiving unit 6. The radio signals from the capsule endoscope 2 correspond to image signals including the in-vivo images of the subject obtained by the capsule endoscope 2 using the imaging function.

The receiving unit 6 is connected to the receiving antennas 5 described above and receives the image signals from the capsule endoscope 2 through the receiving antennas 5. Specifically, the receiving unit 6 selects a receiving antenna having a strongest electric field intensity received thereby from the receiving antennas 5 and receives the radio signals from the capsule endoscope 2 through the selected receiving antenna. The receiving unit 6 performs a demodulation process and the like to the radio signals received from the capsule endoscope 2, extracts the image signals included in the radio signals, and sends the extracted image signals to the control unit 11.

The position and posture detection unit 7 three-dimensionally detects a position and a posture of the capsule endoscope 2 in the subject. Specifically, the position and posture detection unit 7 generates magnetic fields in two axis directions of the three axis directions of the xyz coordinate system described above based on the control of the control unit 11 and generates an induction magnetic field from the capsule endoscope 2 in the subject by the actions of the respective magnetic fields in the two axis directions. The position and posture detection unit 7 detects a magnetic field intensity and a magnetic field direction of the induction magnetic field from the capsule endoscope 2 in the subject as to the two axis directions of the xyz coordinate system described above. The position and posture detection unit 7 calculates a space coordinate and a direction vector (respective direction vectors in a longitudinal direction and a diameter direction of the capsule endoscope 2) of the capsule endoscope 2 in the xyz coordinate system described above based on a result of detection of the induction magnetic field. The position and posture detection unit 7 three-dimensionally detects a present position and a present posture of the capsule endoscope 2 in the subject based on the space coordinate and the direction vector of the capsule endoscope 2 in the xyz coordinate system. The position and posture detection unit 7 sends the present location information and the present posture information of the capsule endoscope 2 in the subject detected as described above to the control unit 11.

The posture of the capsule endoscope 2 is determined by a longitudinal direction of a capsule casing of the capsule endoscope 2 and a rotating state of a center of a longitudinal axis of the capsule endoscope 2 prescribed by a diameter direction of the capsule casing (a direction vertical to the longitudinal direction of the capsule casing).

The input unit 8 is realized using an input device such as a keyboard and a mouse and inputs various kinds of information to the control unit 11 in response to an input operation performed by users such as a doctor and a nurse. The various kinds of information input to the control unit 11 by the input unit 8 is, for example, instruction information instructed to the control unit 11, information as to the imaging function of the capsule endoscope 2, patient information of the subject, examination information of the subject, and the like. The information as to the imaging function of the capsule endoscope 2 is a plurality of types of capturing conditions and the like of in-vivo images, for example, a frame rate at the time the in-vivo images of the subject are sequentially captured, an angle of view, the number of pixels of one side of an in-vivo image, a focusing position or an image capturing time of an optical system, and the like. Further, the patient information of the subject is a patient name, a patient ID, a date of birth, sexuality, an age, and the like of the subject, and the examination information of the subject is an examination ID, an examination date, and the like of a capsule endoscope examination (examination for observing inside of a gastrointestinal tract by introducing the capsule endoscope 2 thereinto) performed to the subject.

The display unit 9 is realized using various types of displays such as a CRT display and a liquid crystal display and displays various kinds of information whose display is instructed by the control unit 11. Specifically, the display unit 9 displays information useful for the capsule endoscope examination such as a group of in-vivo images of the subject captured by the capsule endoscope 2, the patient information of the subject, examination information of the subject, and the like. The users such as the doctor and the nurse observe the group of the in-vivo images displayed on the display unit 9 and examine inside of an organ of the subject by observing the group of the in-vivo images. Further, the display unit 9 displays information useful for magnetically guiding the capsule endoscope 2 such as present position information, present posture information, and the like of the capsule endoscope 2 in the subject.

The storage unit 10 is realized using various storage mediums such as a RAM, an EEPROM, a flash memory, or a hard disk for rewritably storing information. The storage unit 10 stores therein the various kinds of information whose storage is instructed by the control unit 11 and sends information whose read-out is instruct by the control unit 11 to the control unit 11 from the various kinds of information stored. The information stored in the storage unit 10 are information, for example, the group of the in-vivo images of the subject, the patient information and the examination information of the subject, the present position information and the present posture information of the capsule endoscope 2 in the subject, the information as to the imaging function of the capsule endoscope 2, and the like.

The control unit 11 controls the operations of the respective units (the magnetic field generating unit 3, the coil power supply 4, the receiving unit 6, the position and posture detection unit 7, the input unit 8, the display unit 9, and the storage unit 10) of the in-vivo observing system 1 and controls signals which are input and output between the respective units. Specifically, the control unit 11 controls the respective operations of the receiving unit 6, the position and posture detection unit 7, the display unit 9, and the storage unit 10 described above based on the instruction information input by the input unit 8. Further, the control unit 11 controls the amount of current supplied to the magnetic field generating unit 3 from the coil power supply 4 based on the instruction information input by the input unit 8 and controls the magnetic field generating operation of the magnetic field generating unit 3 described above by controlling the coil power supply 4. In this case, the control unit 11 controls the respective operation timings of the magnetic field generating unit 3, the receiving unit 6, and the position and posture detection unit 7 so that a timing at which the magnetic field generating unit 3 generates the external magnetic fields to the capsule endoscope 2, a timing at which the receiving unit 6 receives the radio signals from the capsule endoscope 2, and a timing at which the position and posture detection unit 7 detects the present position and the present posture of the capsule endoscope 2 do not overlap each other.

Further, the control unit 11 includes a magnetic field control unit 11a and a speed setting unit 11b. The magnetic field generating unit 3 controls a guide of the capsule endoscope 2 in the subject (at least one of an offset in the subject and a change of the posture) by controlling the external magnetic fields applied to the capsule endoscope 2 in the subject. Specifically, the speed setting unit 11b calculates an angular speed based on the information (for example, the frame rate, the angle of view, the number of pixels of one side of the in-vivo image, and the plurality of types of the image capturing conditions) as to the imaging function of the capsule endoscope 2 input by the input unit 8 and sets the calculated angular speed as the angular speed used when the magnetic field directions of the external magnetic fields are changed by the magnetic field generating unit 3. The magnetic field control unit 11a controls a magnetic attracting force, a magnetic repulsive force, and magnetic field directions of the external magnetic fields (the gradient magnetic fields or the rotating magnetic fields) applied to the capsule endoscope 2 in the subject by the magnetic field generating unit 3 by controlling the amount of the alternating current supplied from the coil power supply 4 to the magnetic field generating unit 3. The magnetic field control unit 11a causes the magnetic field generating unit 3 to change the magnetic field directions of the external magnetic fields (i.e., the image capturing direction of the capsule endoscope 2 which changes the posture following the external magnetic fields) at the angular speed set by the speed setting unit 11b.

Further, the control unit 11 has an image processing function for creating (replaying) in-vivo images of the subject based on the image signals demodulated by the receiving unit 6 described above. Specifically, the control unit 11 obtains the image signals from the receiving unit 6, executes a predetermined image processing to the obtained image signals, and creates the in-vivo images of the subject. The control unit 11 causes the storage unit 10 to sequentially store the created in-vivo images of the subject and causes the display unit 9 to display a group of the in-vivo images of the subject based on the information instructed from the input unit 8.

Figure 2:
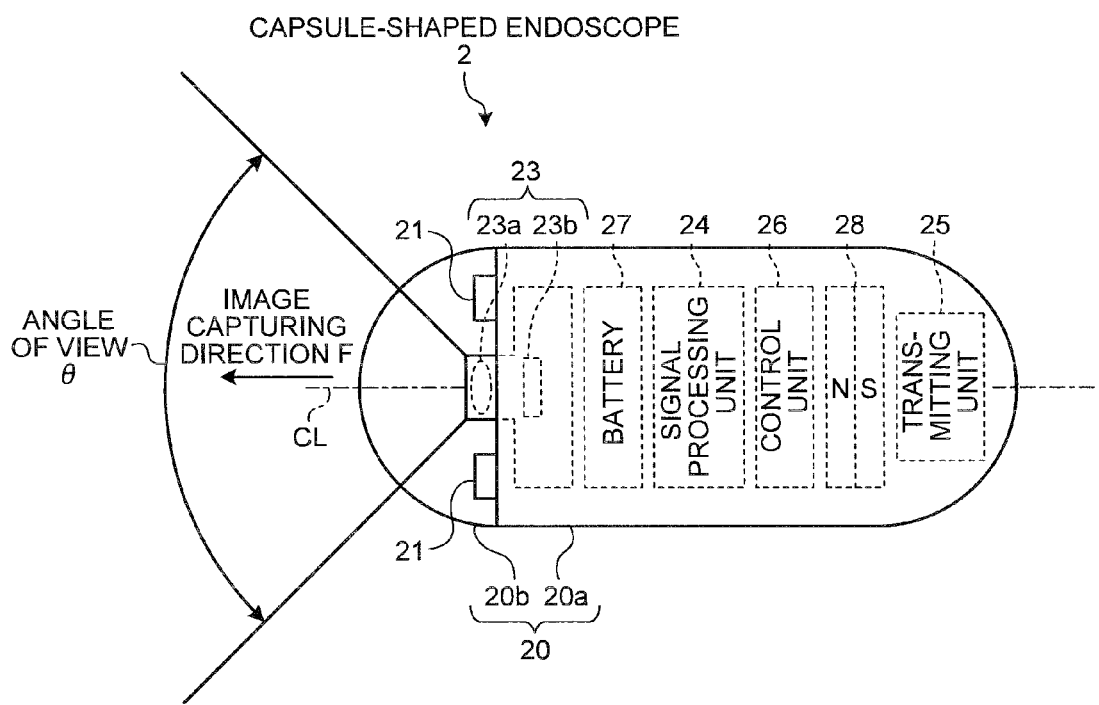
FIG. 2 is a schematic view showing an arrangement example of a capsule endoscope according to the first embodiment of the invention.
Figure 3:
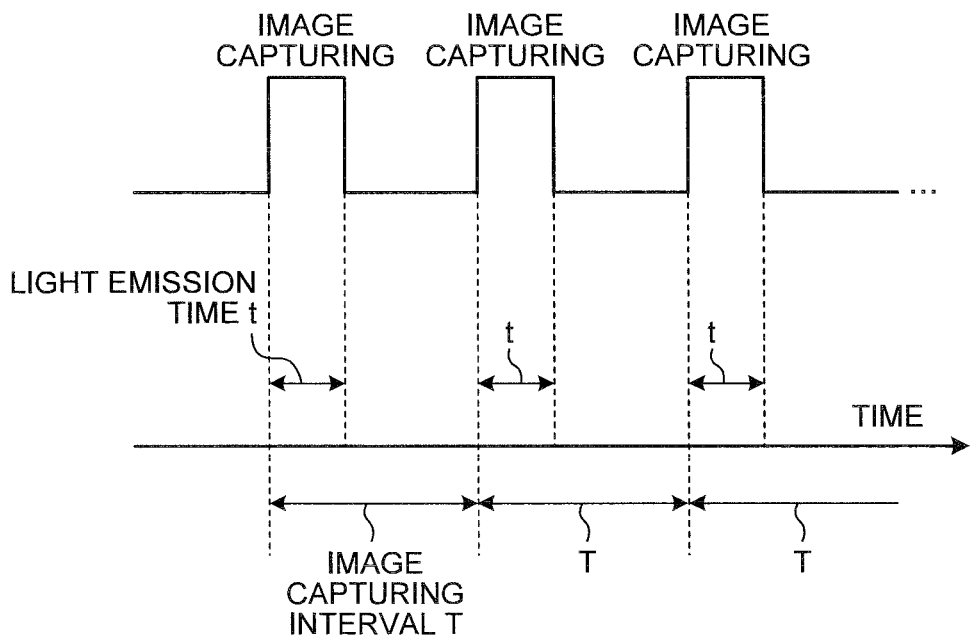
FIG. 3 is a schematic view exemplifying timings at which in-vivo images are captured by the capsule endoscope.

Next, an arrangement of the capsule endoscope 2 as an example of the in-vivo image acquisition device according to the first embodiment of the invention will be explained in detail. FIG. 2 is a block diagram schematically showing an arrangement example of the capsule endoscope 2 according to the first embodiment of the invention. FIG. 3 is a schematic view exemplifying timings at which in-vivo images are captured by the capsule endoscope 2. As shown in FIG. 2, the capsule endoscope 2 includes a capsule casing 20 formed in a size which can be easily introduced into an organ of the subject. Further, the capsule endoscope 2 includes illuminating units 21 for illuminating inside of the subject, the imaging unit 23 for capturing in-vivo images of the subject illuminated by the illuminating units 21, a signal processing unit 24 for creating the in-vivo images captured by the imaging unit 23, a transmitting unit 25 for wireless transmitting the in-vivo images to the outside, a control unit 26, a battery 27 for supplying power to the respective components of the capsule endoscope 2, and the magnet 28 for operating the casing 20 following the external magnetic field of the magnetic field generating unit 3 described above.

The casing 20 is a capsule casing formed in the size which can be easily introduced into an organ of the subject such as the patient and acts as an outer casing of the capsule endoscope 2. The casing 20 is formed by a cylindrical barrel 20a having a cylindrical structure and an optical dome 20b having a dome structure and contains the illuminating units 21, the imaging unit 23, the signal processing unit 24, the transmitting unit 25, the control unit 26, the battery 27, and the magnet 28 in a liquid tight state. The cylindrical barrel 20a is a cylindrical exterior member having one end formed in a dome shape and the other end having an aperture and accommodates therein the illuminating units 21, the imaging unit 23, the signal processing unit 24, the transmitting unit 25, the control unit 26, the battery 27, and the magnet 28. The optical dome 20b is attached to an aperture end of the cylindrical barrel 20a. The optical dome 20b is a dome-shaped optical member transparent to a predetermined light wavelength band and closes the aperture end of the cylindrical barrel 20a.

The illuminating units 21 are realized using a light emitting device such as an LED and illuminate inside of the subject (inside of an organ) by illumination light. Specifically, the illuminating units 21 radiate illumination light (for example, white light) to inside of an organ of the subject through the optical dome 20b and illuminate inside of the organ, which is an image capturing field of view of the imaging unit 23, by the illumination light through the optical dome 20b.

The imaging unit 23 is fixedly arranged in the casing 20 and captures in-vivo images of the subject illuminated by the illuminating units 21. Specifically, the imaging unit 23 includes an optical system 23*a* such as a condenser lens and a solid image capturing device 23*b* such as a CMOS image sensor and a CCD. The optical system 23*a* collects the light reflected from inside of an organ of the subject illuminated by the illuminating units 21 (that is, the image capturing field of view of the imaging unit 23) described above and focuses the image of the subject on a light receiving surface of the solid image capturing device 23*b*. The solid image capturing device 23*b* disposes its light receiving surface at a focus position of the optical system 23*a*, receives the light reflected from inside of an organ through the light receiving surface, and creates image data of an in-vivo image by subjecting the reflected light received to a photoelectric conversion process.

As shown in FIG. 2, the imaging unit 23 including the optical system 23*a* and the solid image capturing device 23*b* has an angle of view θ [degree] and the image capturing field of view (which may be called also an image capturing field of view of the capsule endoscope 2 below) prescribed by the angle of view θ in an image capturing direction F approximately parallel to a center axis CL in the longitudinal direction of the capsule casing 20. In this case, the optical axis of the imaging unit 23 is approximately parallel to the center axis CL of the casing 20 and preferably approximately agrees therewith. Further, the imaging unit 23 sequentially captures in-vivo images in an organ positioned in the image capturing field of view at a predetermined frame rate f [frame/second]. The image data of the in-vivo image captured by the imaging unit 23 is sequentially transmitted to the signal processing unit 24.

The signal processing unit 24 obtains the image data from the imaging unit 23, subjects the obtained image data to the predetermined image process, and creates image signals including the in-vivo image captured by the imaging unit 23. The image signals created by the signal processing unit 24 are sequentially transmitted to the transmitting unit 25. The transmitting unit 25 sequentially wirelessly transmits the in-vivo image captured by the imaging unit 23 described above to the outside. Specifically, the transmitting unit 25 obtains the image signals (that is, the image signals including the in-vivo images captured by the imaging unit) created by the signal processing unit 24, subjects the obtained image signals to a modulation processing and the like, and creates radio signals obtained by modulating the image signals. The transmitting unit 25 sequentially transmits the radio signals to the outside (specifically, to the receiving unit 6 shown in FIG. 1).

The control unit 26 controls the illuminating units 21, the imaging unit 23, and the transmitting unit 25 which are described above and controls a signal input and output between the respective components of the capsule endoscope 2. Specifically, as shown in FIG. 3, the control unit 26 causes the imaging unit 23 to capture the in-vivo images of the subject illuminated by illumination light from the illuminating units 21 at each predetermined image capturing interval T. In this case, the control unit 26 causes the illuminating units 21 to simultaneously emit illumination light for only a light emission time t at each image capturing interval T as well as exposes the imaging unit 23 in the same time as the light emission time t of the illumination light. Further, the control unit 26 causes the transmitting unit 25 to wirelessly transmit the in-vivo images captured by the imaging unit 23 to the transmitting unit 25 time-sequentially.

The image capturing interval T of the imaging unit 23 controlled by the control unit 26 is a time interval from a time at which an in-vivo image of one frame starts to be captured to a time at which an in-vivo image of a next frame starts to be captured and includes the light emission time t of the illumination light in which the illuminating units 21 are emitted, the light receiving time (exposure time) of the imaging unit 23, the image processing time of the in-vivo images processed by the signal processing unit 24 described above, and the like. The image capturing interval T prescribes the frame rate f of the imaging unit 23 described above. That is, the frame rate f of the imaging unit 23 has the same value as the inverted number of the image capturing interval T. Further, the light emission time t of the illuminating units 21 controlled by the control unit 26 is an example of an image capturing time when the imaging unit 23 captures the in-vivo image of one frame and has the same value as the light receiving time of the imaging unit 23.

The magnet 28 allows the capsule endoscope 2 to be guided by the external magnetic fields formed by the magnetic field generating unit 3 described above (refer to FIG. 1). Specifically, the magnet 28 is disposed at a predetermined position in the casing 20 and magnetized in a predetermined direction, for example, in the longitudinal direction of the casing 20 and more preferably in the same direction as the image capturing direction F of the imaging unit 23. The magnet 28 operates the casing 20 following the external magnetic fields of the magnetic field generating unit 3 described above. In this case, the magnet 28 moves the casing 20 by the magnetic attracting force or the magnetic repulsive force of the external magnetic fields generated by the magnetic field generating unit 3. The capsule endoscope 2 is offset to a desired position in the subject due to the action of the magnet 28. Further, the magnet 28 changes a posture of the casing 20, i.e., the posture of the capsule endoscope 2 following a change of the magnetic field directions of the external magnetic fields of the magnetic field generating unit 3. A relative direction of the capsule endoscope 2 to the subject is changed as well as the image capturing direction F of the imaging unit 23 is changed to a desired direction in the subject by the operation of the magnet 28.

Although not particularly shown in FIG. 2, a magnetic field generating coil is disposed in the casing 20 of the capsule endoscope 2 to generate an induction magnetic field due to the action of a magnetic field formed by the position and posture detection unit 7 described above. The magnetic field generating coil is realized using two coils having aperture directions thereof disposed in, for example, two orthogonal axis directions.

Figure 4:
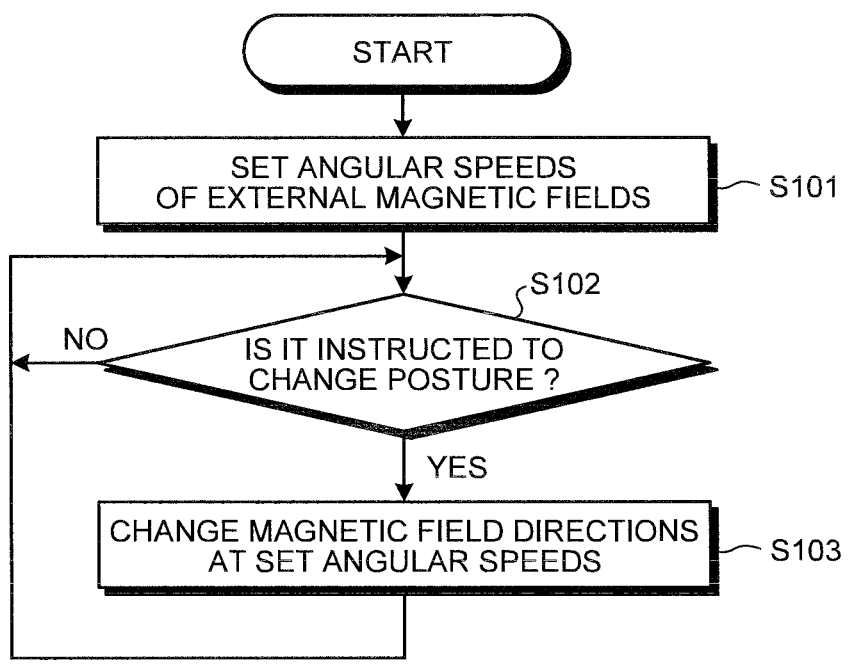
FIG. 4 is a flowchart exemplifying a process procedure of a control unit for controlling an image capturing direction of the capsule endoscope by controlling magnetic field directions of external magnetic fields by a magnetic field generating unit.

Next, an operation of the control unit 11 for causing the magnetic field generating unit 3 to change the relative image capturing direction F of the capsule endoscope 2 to the subject will be explained. FIG. 4 is a flowchart exemplifying a process procedure of the control unit 11 for controlling the image capturing direction F of the capsule endoscope 2 by controlling the magnetic field directions of the external magnetic fields by the magnetic field generating unit 3.

As described above, the control unit 11 causes the magnetic field generating unit 3 to generate the external magnetic fields applied to the magnet 28 of the capsule endoscope 2 in the subject. The control unit 11 causes the magnetic field generating unit 3 to change the relative direction of the capsule endoscope 2 to the subject (i.e., the posture of the capsule endoscope 2 in the subject) by controlling the magnetic field directions of the external magnetic fields. As a result, the control unit 11 causes the magnetic field generating unit 3 to change the image capturing direction F of the imaging unit 23 of the capsule endoscope 2.

More specifically, as shown in FIG. 4, the control unit 11 first sets angular speeds of the external magnetic fields for causing the magnetic field generating unit 3 described above to change the magnetic field directions (step S101). At step S101, the speed setting unit 11*b* obtains the angle of view θ and the frame rate of the imaging unit 23, the number of pixels m of one side of an in-vivo image, and the light emission time t of the illumination light as information as to the imaging function of the capsule endoscope 2 input by the input unit 8 and sets the angular speeds of the external magnetic fields appropriately using the thus obtained various kinds of information.

To explain this in detail, the speed setting unit 11b calculates an angular speed ω1 [degree/second] less than a multiplied value obtained by multiplying the angle of view θ by the frame rate f and sets the calculated angular speed ω1 as an average angular speed of the external magnetic fields when the magnetic field directions of the external magnetic fields are changed in the image capturing interval T described above. Further, the speed setting unit 11b calculates an angular speed ω2 [degree/second] less than a divided value obtained by dividing the angle of view θ by a multiplied value obtained by multiplying the number of pixels m of one side of the in-vivo image by the light emission time t and sets the calculated angular speed ω2 as an average angular speed of the external magnetic fields when the magnetic field directions of the external magnetic fields are changed in an image capturing time (for example, the light emission time t) of the image capturing interval T described above. These angular speeds ω1, ω2 are stored to the storage unit 10 and read out by the control unit 11 when necessary.

The number of pixels m of the one side of the in-vivo image is any one of the number of pixels of one side (for example, a long side) of a light receiving surface of the imaging unit 23 for capturing the in-vivo image and the number of pixels of one side of an in-vivo image display system (for example, the display unit 9 shown in FIG. 1) corresponding to the one side of the light receiving surface. When the number of pixels of the one side of the imaging unit 23 is equal to or less than the number of pixels of the one side of the display system, the speed setting unit 11b uses the number of pixels of the one side of the imaging unit 23 as the number of pixels m of the one side described above, whereas when the number of pixels of the one side of the imaging unit 23 exceeds the number of pixels of the one side of the display system, the speed setting unit 11b uses the number of pixels of the one side of the display system as the number of pixels m of the one side described above.

Next, the control unit 11 determines whether or not it is instructed to change the posture of the capsule endoscope 2 in the subject (step S102). At step S102, when the instruction information for changing the posture of the capsule endoscope 2 in the subject is not input, the control unit 11 determines that it is not instructed to change the posture of the capsule endoscope 2 (step S102, No) and repeats a process procedure at step S102. In contrast, when the instruction information for changing the posture of the capsule endoscope 2 is input by the input unit 8, the control unit 11 determines that it is instructed to change the posture of the capsule endoscope 2 (step S102, Yes) and causes the magnetic field generating unit 3 to change the magnetic field directions of the external magnetic fields at the angular speeds ω1, ω2 set at step S101 described above (step S103).

At step S103, the magnetic field control unit 11a controls the magnetic field generating unit 3 so that it changes the magnetic field directions of the external magnetic fields at the angular speed ω1 described above (<frame rate f×angle of view θ) in the image capturing interval T of the imaging unit 23 excluding an image capturing time of an in-vivo image (the light emission time t of the illumination light or the light receiving time of the imaging unit 23). In contrast, the magnetic field control unit 11a controls the magnetic field generating unit 3 so that it changes the magnetic field directions of the external magnetic fields at the angular speed ω2 described above (<angle of view θ÷(number of pixels m of one side× light emission time t)) in the image capturing time of the in-vivo image of the image capturing interval T of the imaging unit 23, i.e., during a period in which the imaging unit 23 captures the in-vivo image.

The magnetic field control unit 11a detects the image capturing interval T of the imaging unit 23 based on the frame rate f of the imaging unit 23 input by the input unit 8 and detects the image capture timing of the imaging unit 23 based on the information (in-vivo image and the like) from the capsule endoscope 2 received by the receiving unit 6 or on synchronization signals such as reception timing.

As described above, the magnetic field control unit 11a controls the magnetic field directions of the external magnetic fields of the magnetic field generating unit 3, whereby the magnetic field generating unit 3 changes the image capturing direction F of the capsule endoscope 2 following the magnetic field directions of the external magnetic fields in the image capturing interval T of the imaging unit 23 excluding the image capturing time of the in-vivo image at the angular speed ω1 described above and changes the image capturing direction F of the capsule endoscope 2 following the magnetic field directions of the external magnetic fields at the angular speed ω2 described above during the period in which the imaging unit 23 captures the in-vivo image. Thereafter, the control unit 11 returns to step S102 described above and repeats process procedures at step S102 and subsequent steps.

Figure 5:
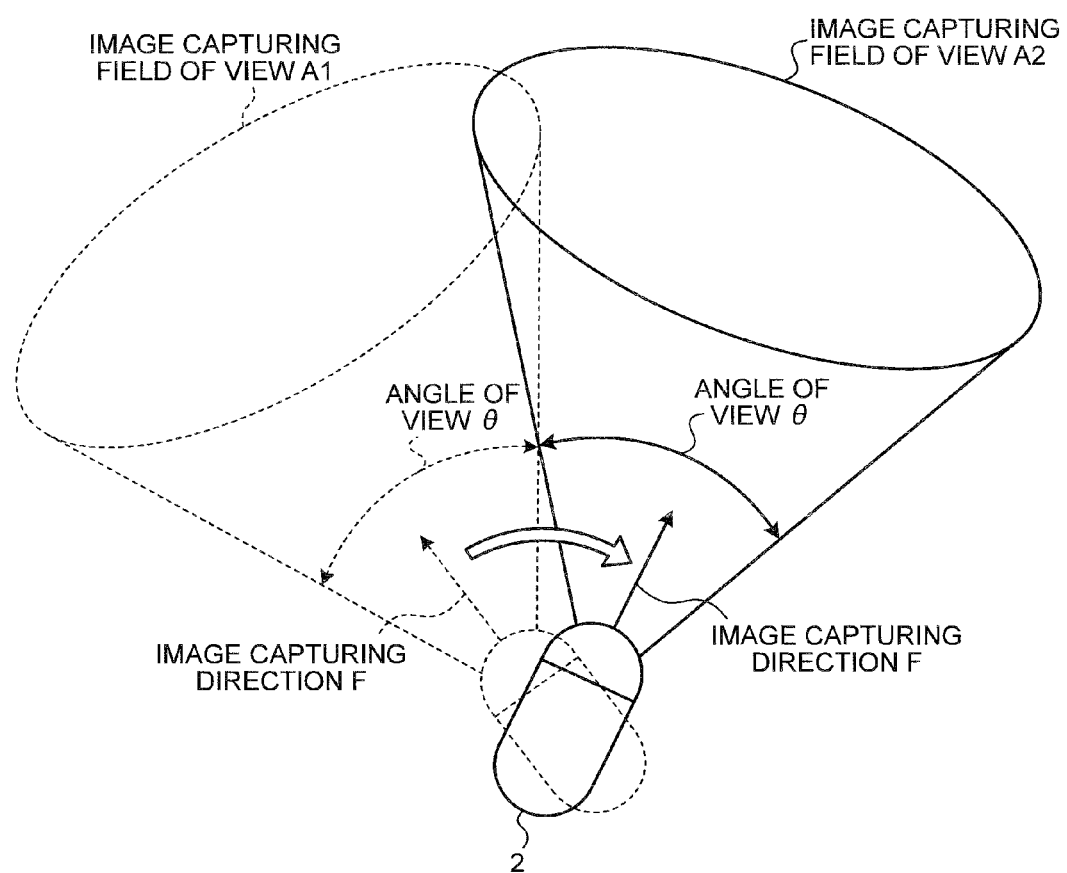
FIG. 5 is a schematic view exemplifying an image capturing state in which the capsule endoscope sequentially captures in-vivo images while changing an image capturing direction following the magnetic field direction of the external magnetic field.
Figure 6:
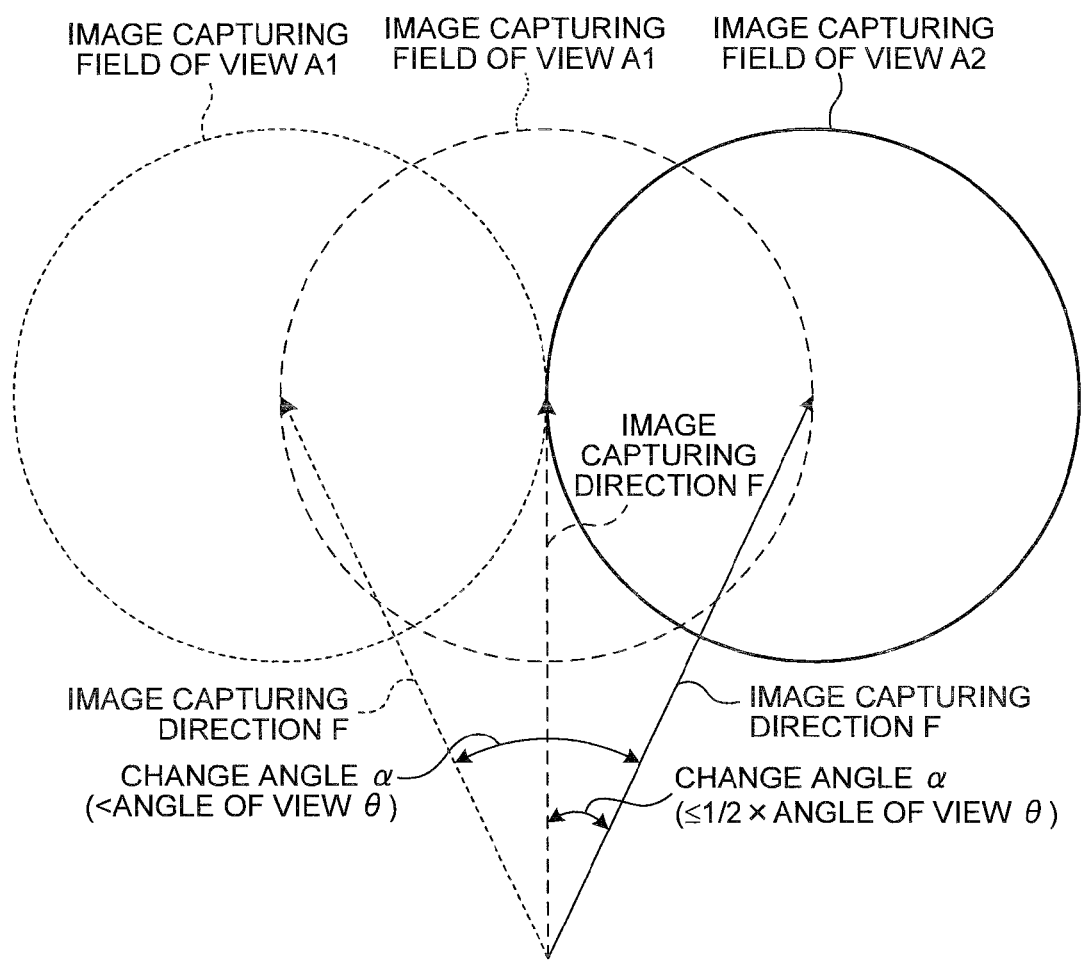
FIG. 6 is a schematic view exemplifying an image capturing field of view of the capsule endoscope offset by changing the image capturing direction.
Figure 7:
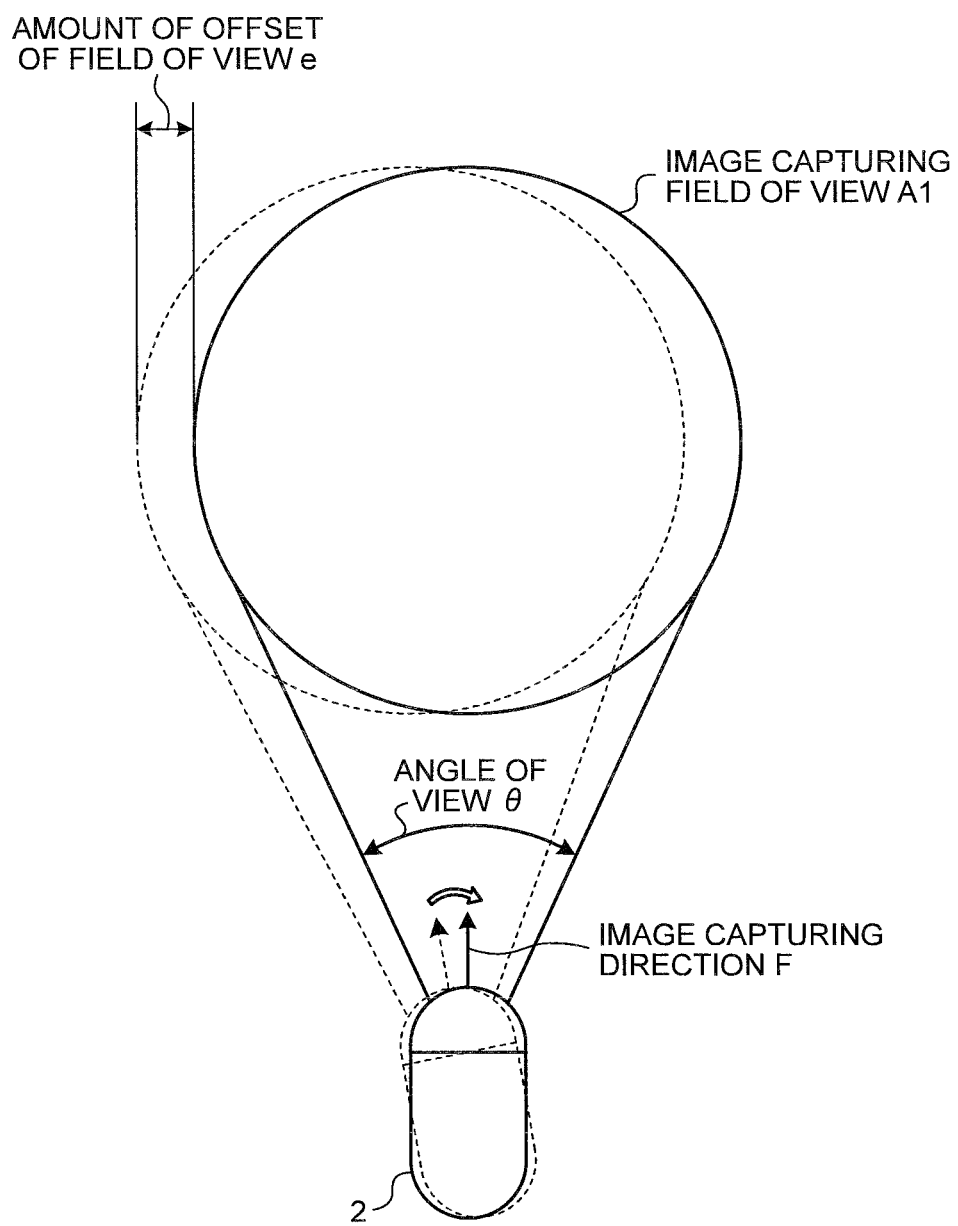
FIG. 7 is a schematic view exemplifying a state in which an image capturing field of view of the capsule endoscope is offset by changing the image capturing direction.

Next, how the capsule endoscope 2 in the subject is affected by the external magnetic fields of the magnetic field generating unit 3 whose magnetic field directions are controlled by the control unit 11 described above and an in-vivo image capturing step and an image capturing direction change step in the in-vivo observing method according to the invention will be specifically explained by exemplifying a case in which the capsule endoscope 2 in the subject sequentially captures in-vivo images of two frames. FIG. 5 is a schematic view exemplifying an image capturing state in which the capsule endoscope 2 sequentially captures in-vivo images while changing an image capturing direction F following the magnetic field directions of the external magnetic fields. FIG. 6 is a schematic view exemplifying an image capturing field of view of the capsule endoscope 2 offset by changing the image capturing direction F. FIG. 7 is a schematic view exemplifying a state in which an image capturing field of view of the capsule endoscope 2 is offset by changing the image capturing direction F.

In FIGS. 5 and 6, capturing fields of view A1, A2 are the capturing fields of view of the capsule endoscope 2, which catch inside of an organ of the subject (the imaging unit 23 in detail), and prescribed by the angle of view θ as described above. In the image capturing fields of view A1, A2, the image capturing field of view A1 is an image capturing field of view corresponding to the in-vivo image of a first frame of the in-vivo images of the two frames which are sequentially captured by the capsule endoscope 2, and the image capturing field of view A2 is an image capturing field of view corresponding to the in-vivo image of a second frame of the in-vivo images of the two frames.

As shown in FIG. 5, the capsule endoscope 2 changes the relative direction (i.e., the posture) to the subject following the external magnetic fields of the magnetic field generating unit 3 whose magnetic field directions are controlled by the control unit 11 described above and sequentially captures the in-vivo image corresponding to the image capturing field of view A1 and the in-vivo image corresponding to the image capturing field of view A2. In this case, the capsule endoscope 2 changes the image capturing direction F from the image capturing direction F of the image capturing field of view A1 (dotted line arrow) to the image capturing direction F of the image capturing field of view A2 (solid line arrow) following the magnetic field directions of the external magnetic fields of the magnetic field generating unit 3.

The magnetic field generating unit 3 described above changes the magnetic field directions of the external magnetic fields for inducing a change of posture of the capsule endoscope 2 at the angular speed $\omega 1$ (<frame rate f×angle of view $\theta$) in the image capturing interval T of the capsule endoscope 2 excluding the image capturing time of the in-vivo image based on the control of the magnetic field control unit 11a and changes the magnetic field directions of the external magnetic fields at the angular speed $\omega 2$ (<angle of view $\theta$÷(number of pixels m of one side×light emission time t) during the period in which the capsule endoscope 2 captures an in-vivo image in the image capturing interval T. The capsule endoscope 2 changes the image capturing direction F of the image capturing field of view A1 to the image capturing direction F of the image capturing field of view A2 at the angular speed $\omega 1$ and in particular changes the image capturing direction F at angular speed $\omega 2$ during the respective periods in which the in-vivo images of the image capturing fields of view A1, A2 are captured following the external magnetic fields for changing the magnetic field directions at the angular speeds $\omega 1$, $\omega 2$.

When the capsule endoscope 2 changes the image capturing direction F by an operation of the external magnetic fields of the magnetic field generating unit 3 as described above, a change angle $\alpha$ [degree] of the image capturing direction F is less than the angle of view $\theta$ of the capsule endoscope 2. Specifically, as shown in FIG. 6, the change angle $\alpha$ between the image capturing direction F of the image capturing field of view A1 and the image capturing direction F of the image capturing field of view A2 (i.e., the image capturing direction F after it is changed) is less than the angle of view $\theta$ at all times. When, for example, the frame rate f of the imaging unit 23 of the capsule endoscope 2 is 4 [frame/second] and the angle of view $\theta$ is 120 [degree], the angular speed $\omega 1$ described above is less than 480 [degree/second], and the change angle $\alpha$ of the image capturing direction F is less than 120 [degree] at all times due to the action of the external magnetic fields for changing the magnetic field directions at the angular speed $\omega 1$.

As a result, the image capturing field of view A1 in the image capturing direction F overlaps the field of view region of least a part of the image capturing field of view A2 in the image capturing direction F after it is changed. The capsule endoscope 2 can securely capture a group of in-vivo images in which at least parts of image portions overlap between the in-vivo images by sequentially capturing the respective in-vivo images of the image capturing fields of view A1, A2 in which field of view regions overlap as described above. When the capsule endoscope 2 time-sequentially captures a group of in-vivo images of the subject, it can securely obtain a group of continuous in-vivo images in which at least parts of image portions overlap between the in-vivo images adjacent to each other in time.

In the group of the continuous in-vivo images captured by the capsule endoscope 2, it is preferable to more increase the overlap portions of the in-vivo images between the images adjacent to each other in time. This is because when more portions of the images overlap, the respective in-vivo images in the group of the continuous in-vivo images can be more accurately coupled with each other by a pattern matching process between the in-vivo images adjacent to each other in time. In this case, it is preferable that the speed setting unit 11b described above sets the angular speed $\omega 1$, which is half or less than a multiplied value obtained by multiplying the angle of view $\theta$ by the frame rate f as an average angular speed of the external magnetic fields when the magnetic field directions of the external magnetic fields are changed in the image capturing interval T of the capsule endoscope 2.

The change angle $\alpha$ between the image capturing direction F of the image capturing field of view A1 and the image capturing direction F of the image capturing field of view A2 is equal to or less than half the angle of view $\theta$ at all times as shown in FIG. 6 by setting the angular speed $\omega 1$ (<=frame rate f×angle of view $\theta$÷2) as described above. When, for example, the frame rate f of the imaging unit 23 of the capsule endoscope 2 is 4 [frame/second] and the angle of view $\theta$ is 120 [degree], the angular speed $\omega 1$ is equal to or less than 240 [degree/second], and the change angle $\alpha$ of the image capturing direction F is equal to or less than 60 [degree] at all times due to the actions of the external magnetic fields for changing the magnetic field directions at the angular speed $\omega 1$.

As a result, the image capturing field of view A1 in the image capturing direction F overlaps a half or more part of the image capturing field of view A2 in the image capturing direction F after it is changed. The capsule endoscope 2 can securely capture a group of in-vivo images in which half or more parts of image portions overlap each other between the in-vivo images by sequentially capturing the respective in-vivo images of the image capturing fields of view A1, A2 in which the half or more parts of the field of view regions overlap each other as described above. Even when the center of rotation of the image capturing direction F, which rotates following the external magnetic fields, does not agree with the center of the angle of view $\theta$, the capsule endoscope 2 can more securely obtain a group of continuous in-vivo images in which at least parts of image portions overlap each other between the in-vivo images adjacent to each other in time.

In contrast, the capsule endoscope 2 changes the image capturing direction F at the angular speed $\omega 2$ following the external magnetic fields of the magnetic field generating unit 3 for changing the magnetic field directions at the angular speed $\omega 2$ (<angle of view $\theta$÷(number of pixels m of one side×light emission time t)) as described above during the respective periods of the image capturing interval T in which the in-vivo images of the image capturing fields of view A1, A2 are captured. In this case, the image capturing fields of view A1, A2 generate an amount of offset of field of view by changing the image capturing direction F due to the action of the external magnetic fields.

Specifically, as shown in FIG. 7, the image capturing field of view A1 generates the amount of offset e of field of view by changing the image capturing direction F following the external magnetic fields of the magnetic field generating unit 3. The image capturing direction F of the image capturing field of view A1 is changed (rotated) at the angular speed $\omega 2$ in the image capturing time of the in-vivo images as described above. Accordingly, the amount of offset e of field of view of the image capturing field of view A1, which is offset in the image capturing time of the in-vivo images by changing the image capturing direction F, is an amount of offset less than one pixel of an in-vivo image corresponding to the image capturing field of view A1. When, for example, the angle of view $\theta$ of the capsule endoscope 2 is 120 [degree], the image capturing time of in-vivo images of one frame, i.e., the light emission time t of the illumination light is 0.02 [second], and the number of pixels m of one side of an in-vivo image, for example, the number of pixels of one side of the light receiving surface of the imaging unit 23 is 200 pixels, the angular speed $\omega 2$ described above is less than 30 [degree/second].

The amount of offset e of field of view of the image capturing field of view A1 is an amount of offset less than one pixel of the light receiving surface of the imaging unit 23 at all times due to the action of the external magnetic fields for changing the magnetic field directions at the angular speed ω2.

When the number of pixels of the one side of the light receiving surface of the imaging unit 23 is equal to or less than the number of pixels of the one side of the display system of an in-vivo image corresponding to the one side of the light receiving surface, the number of pixels m of one side of the in-vivo image has the same value as the number of pixels of one side of the imaging unit 23. In contrast, when the number of pixels of the one side of the light receiving surface of the imaging unit 23 exceeds the number of pixels of the one side of the display system of the in-vivo image corresponding to the one side of the light receiving surface, the number of pixels m of the one side of the in-vivo image has the same value as the number of pixels of one side of the display system. Accordingly, when the number of pixels of the one side of the light receiving surface of the imaging unit 23 is equal to or less than the number of pixels of the one side of the display system of the in-vivo image corresponding to the one side of the light receiving surface, the amount of offset e of field of view of the image capturing field of view A1 is the amount of offset less than the one pixel of the light receiving surface of the imaging unit 23 as described above. In contrast, when the number of pixels of the one side of the imaging unit 23 exceeds the number of pixels of the one side of the display system, the amount of offset e of field of view of the image capturing field of view A1 described above is an amount of offset less than one pixel of the display system.

As a result, when the number of pixels of the one side of the imaging unit 23 is equal to or less than the number of pixels of the one side of the display system of the in-vivo image, an image fluctuation of the in-vivo image caused by an offset of the image capturing field of view A1 can be reduced to less than one pixel of the light receiving surface of the imaging unit 23, whereas when the number of pixels of the one side of the imaging unit 23 exceeds the number of pixels of the one side of the display system of the in-vivo image, the image fluctuation can be reduced to less than one pixel of the display system of the in-vivo image. Even when an in-vivo image is captured as well as the image capturing direction F is changed, the capsule endoscope 2 can sequentially capture vivid in-vivo images whose image fluctuation is reduced by changing the image capturing direction F at the angular speed ω2 described above. An effect of reducing an image fluctuation of the in-vivo images can be obtained also as to the image capturing field of view A2 of a next frame in which an in-vivo image next to the image capturing field of view A1 is captured likewise.

As explained above, in the first embodiment of the invention, the imaging unit, which sequentially captures in-vivo images whose image capturing direction is prescribed by the posture of the capsule casing, and the magnet, which changes the posture of the capsule casing following the magnetic field directions of the external magnetic fields, are disposed in the capsule casing formed in a size which can be easily introduced into an in-vivo of a subject, the magnetic field generating unit disposed outside of a body applies the external magnetic fields to the magnet in the capsule casing introduced into the subject, the magnetic field directions of the external magnetic fields are changed at the angular speed which is less than a multiplied value obtained by multiplying the angle of view and the frame rate of the imaging unit to thereby change the image capturing direction of the imaging unit at the angular speed together with the posture of the capsule casing.

Thus, a changed angle of the image capturing direction of the imaging unit, which changes following the magnetic field directions of the external magnetic fields, can be kept less than the angle of view of the imaging unit during a period from a time at which an in-vivo image of one frame starts to be captured to a time at which an in-vivo image of a next frame starts to be captured so that the field of view regions of at least parts of respective image capturing fields of view, which are offset by changing the image capturing direction, can be caused to overlap each other. As a result, there can be realized an in-vivo observing system and an in-vivo image obtaining device, which can securely obtain a group of continuous in-vivo images in which at least parts of image portions overlap between the in-vivo images adjacent to each other in time when a group of in-vivo images of the subject are sequentially captured, as well as an in-vivo observing method for observing inside of an organ of the subject by observing the group of in-vivo images.

Uncaptured portions inside of an organ of the subject can be reduced as much as possible as well as the group of continuous in-vivo images can be obtained over approximately the entire region inside of the organ using the in-vivo observing system and the in-vivo image obtaining device according to the first embodiment. As a result, insides of organs such as a stomach and a large intestine of the subject can be entirely observed.

Further, during a period in which an in-vivo image of one frame is captured, the magnetic field directions of the external magnetic fields are changed at the angular speed less than a divided value obtained by dividing the angle of view of the imaging unit by a multiplied value of the number of pixels of one side of the in-vivo image and the image capturing time so that the image capturing direction of the imaging unit is changed at the angular speed. Accordingly, the amount of offset of the image capturing field of view of the imaging unit, which is offset in the image capturing time of the in-vivo image by the change of the image capturing direction, can be kept less than the amount of offset of one pixel of the in-vivo image. An image fluctuation of the in-vivo image of the image capturing field of view can be reduced to less than one pixel of the light receiving surface of the imaging unit or less than one pixel of the display system of an in-vivo image. As a result, even when an in-vivo image is captured while changing the image capturing direction, vivid images whose image fluctuation is reduced can be sequentially captured.

Second Embodiment

Next, a second embodiment of the invention will be explained. In the first embodiment described above, the image capturing conditions of in-vivo images (for example, the light emission time of the illumination light, the light receiving time of the imaging unit 23, and the like) are fixed. However, in the second embodiment, a plurality of types of image capturing conditions of in-vivo images are set, and the in-vivo images are sequentially captured by switching the plurality of types of the image capturing conditions in a predetermined order.

Figure 8:
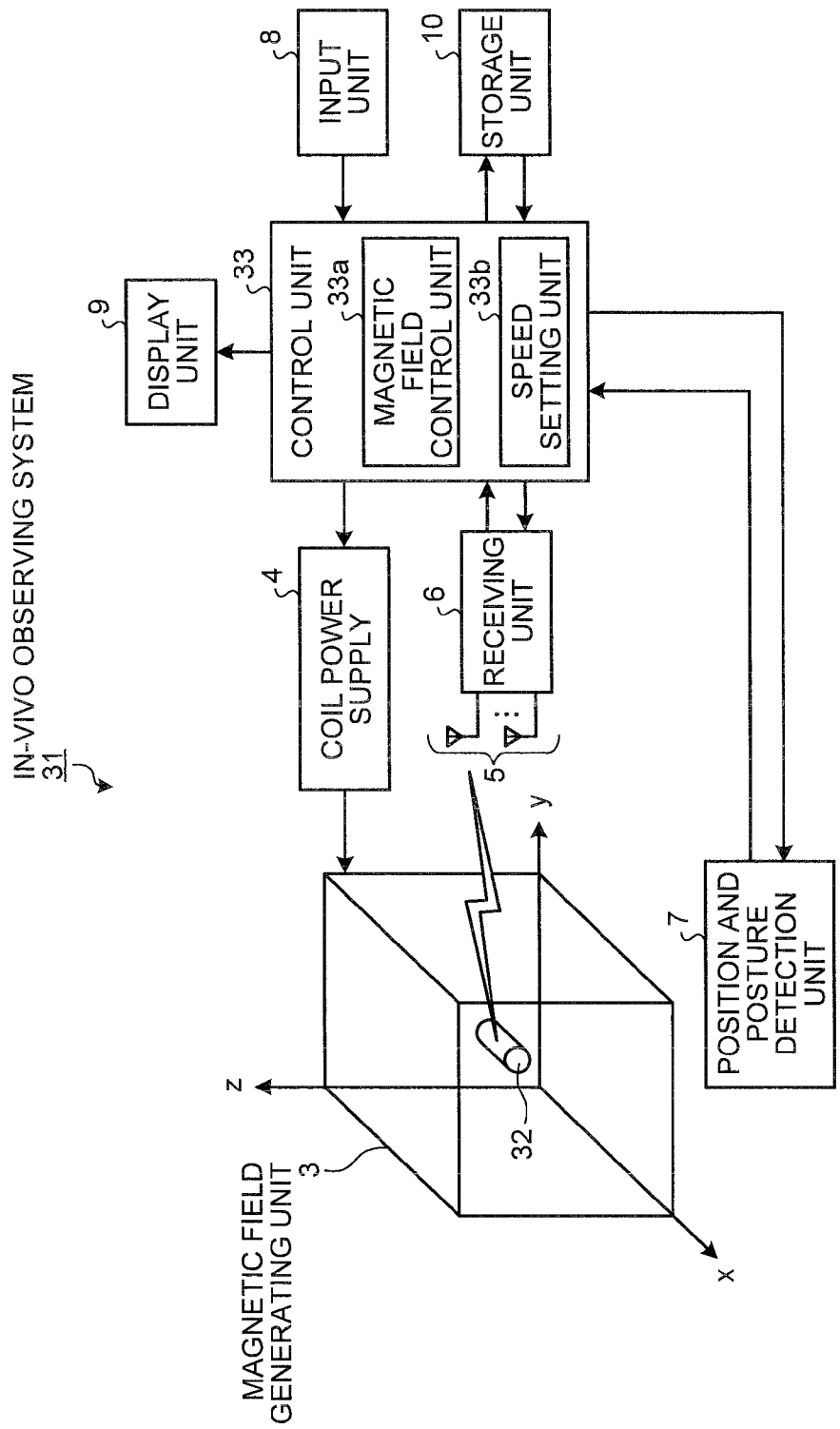
FIG. 8 is a block diagram schematically showing an arrangement example of an in-vivo observing system according to a second embodiment of the invention.

FIG. 8 is a block diagram schematically showing an arrangement example of an in-vivo observing system according to the second embodiment of the invention. As shown in FIG. 8, the in-vivo observing system 31 according to the second embodiment includes a capsule endoscope 32 having the plurality of types of the image capturing conditions in place of the capsule endoscope 2 of the in-vivo observing system 1 according to the first embodiment described above and a control unit 33 in place of the control unit 11. The other arrangements are the same as those of the first embodiment, and the same reference numerals are added to the same components.

The capsule endoscope 32 has the plurality of types of the image capturing conditions (for example, a light emitting condition of illumination light, a light receiving condition of an imaging unit, and the like) for capturing in-vivo images of a subject and sequentially captures in-vivo images of the subject by switching the plurality of types of the image capturing conditions in the predetermined order. With this operation, the capsule endoscope 32 obtains a group of in-vivo images captured under the plurality of types of the image capturing conditions. The types of the image capturing conditions are prescribed by a combination of a light emitting condition of the illumination light when an in-vivo image of one frame is captured, a light receiving condition of the imaging unit 23, and the like. The other functions of the capsule endoscope 32 and the structure of the capsule endoscope 32 are approximately the same as those of the capsule endoscope 2 according to the first embodiment described above. That the plurality of types of the image capturing conditions of the capsule endoscope 32 will be described later.

The control unit 33 includes a magnetic field control unit 33a and a speed setting unit 33b. The magnetic field generating unit 3 controls external magnetic fields applied to the capsule endoscope 32 in the subject to thereby control a guide of the capsule endoscope 32 in the subject (at least one of an offset and a posture in the subject). The speed setting unit 33b calculates an angular speed appropriately using information (for example, a frame rate, an angle of view, the number of pixels of one side of an in-vivo image, and the image capturing conditions) as to an imaging function of the capsule endoscope 32 input by the input unit 8 and the number of the types of the image capturing conditions and sets the calculated angular speed as an angular speed when the magnetic field directions of the external magnetic fields are changed by the magnetic field generating unit 3. The magnetic field control unit 33a causes the magnetic field generating unit 3 to change the magnetic field directions of the external magnetic fields (i.e., the image capturing direction of the capsule endoscope 32 which changes a posture following the external magnetic fields) at an angular speed set by the speed setting unit 33b. The other functions of the control unit 33 are the same as those of the control unit 11 of the in-vivo observing system 1 according to the first embodiment described above.

Figure 9:
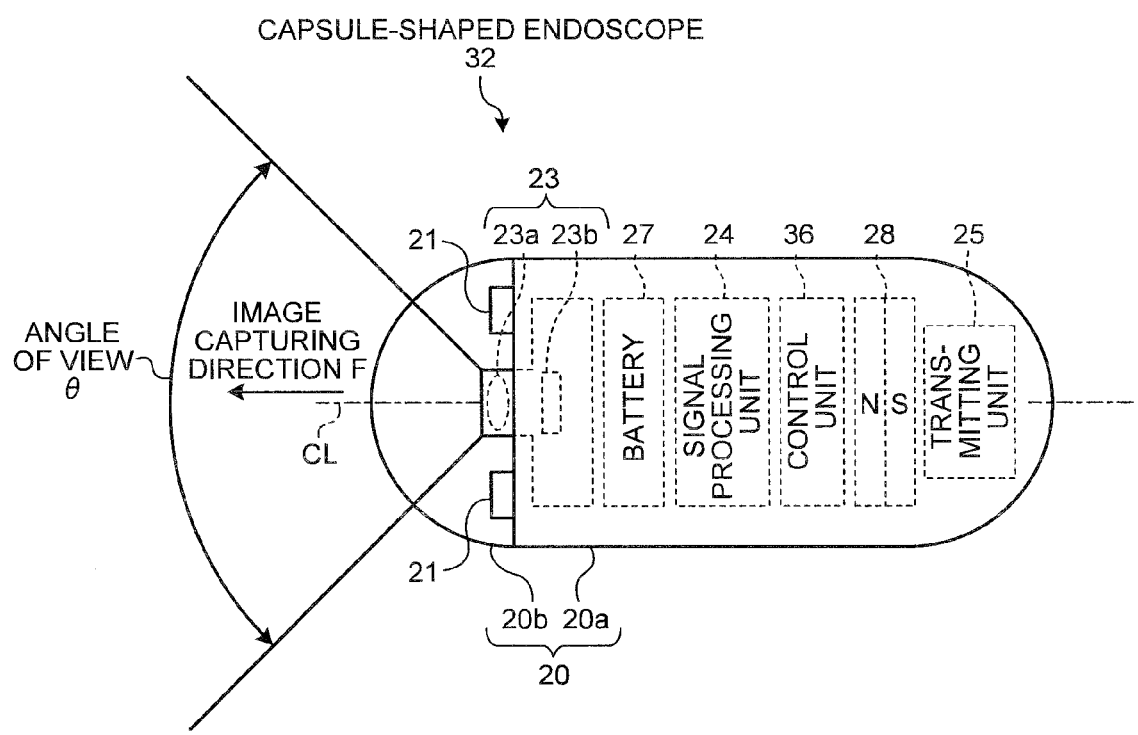
FIG. 9 is a schematic view showing an arrangement example of a capsule endoscope according to the second embodiment of the invention.
Figure 10:
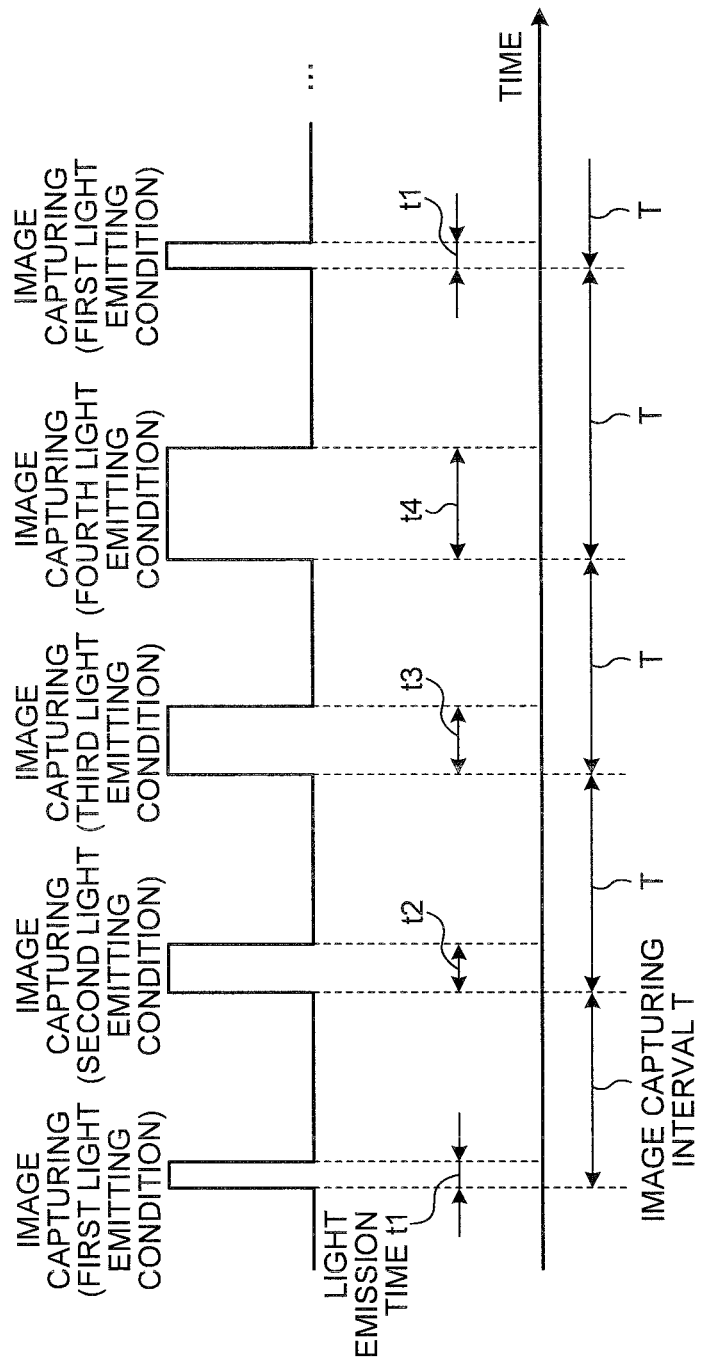
FIG. 10 is a schematic view exemplifying timings at which in-vivo images are captured by a capsule endoscope having a plurality of types of image capturing conditions.

Next, an arrangement of the capsule endoscope 32 as an example of an in-vivo image acquisition device according to the second embodiment of the invention will be explained in detail. FIG. 9 is a schematic view showing an arrangement example of the capsule endoscope 32 according to the second embodiment of the invention. FIG. 10 is a schematic view exemplifying timings at which in-vivo images are captured by the capsule endoscope 32 having the plurality of types of the image capturing conditions. As shown in FIG. 9, the capsule endoscope 32 according to the second embodiment includes a control unit 36 in place of the control unit 26 of the capsule endoscope 2 according to the first embodiment described above. The control unit 36 causes the imaging unit 23 to sequentially capture in-vivo images by sequentially switching the plurality of types of the image capturing conditions in the predetermined order. The other arrangements are the same as those of the first embodiment, and the same reference numerals are given to the same components.

The control unit 36 is previously set with the plurality of types of the image capturing conditions and causes the imaging unit 23 to sequentially capture in-vivo images of the subject by sequentially switching the plurality of types of the image capturing conditions in the predetermined order. Specifically, as shown in FIG. 10, the control unit 36 switches, for example, light emission times t1 to t4 of the illumination light in each image capturing interval T (i.e., each frame) in the predetermined order as the image capturing conditions of the in-vivo images and causes the imaging unit 23 to sequentially capture a plurality of types of in-vivo images which are classified depending on an amount of light emission of the illumination light. In the light emission times t1 to t4 of the illumination light, the light emission time t4 has a maximum value, the light emission time t3 is larger than the light emission times t1, t2, and the light emission time t2 is larger than the light emission time t1.

More specifically, the control unit 36 causes a plurality of illuminating units 21 to emit the illumination light only for the light emission time t1 as well as causes the imaging unit 23 to capture an in-vivo image of a subject (in-vivo image of a first light emitting condition) illuminated by the illumination light emitted for the light emission time t1. Just after the above operation, the control unit 36 causes the illuminating units 21 to emit the illumination light only for the light emission time t2 as well as causes the imaging unit 23 to capture an in-vivo image of the subject (in-vivo image of a second light emitting condition) illuminated by the illumination light emitted for the light emission time t2. Subsequently, the control unit 36 switches the light emission time t2 to the light emission time t3 and causes the illuminating units 21 to emit the illumination light only for the light emission time t3 as well as causes the imaging unit 23 to capture an in-vivo image of the subject (in-vivo image of a third light emitting condition) illuminated by the illumination light emitted for the light emission time t3. Just after the above operation, the control unit 36 causes the illuminating units 21 to emit the illumination light only for the light emission time t4 as well as causes the imaging unit 23 to capture an in-vivo image of the subject (in-vivo image of a fourth light emitting condition) illuminated by the illumination light emitted for the light emission time t4. Thereafter, the control unit 36 repeatedly switches the light emission times t1 to t4 of the illumination light likewise and causes the imaging unit 23 to repeatedly capture the in-vivo image of the first light emitting condition, the in-vivo image of the second light emitting condition, the in-vivo image of the third light emitting condition, and the in-vivo image of the fourth light emitting condition. The other functions of the control unit 36 are the same as those of the control unit 26 of the capsule endoscope 2 according to the first embodiment described above.

The control unit 36 sequentially switches the light receiving times of the imaging unit 23 in synchronization with switching of the light emission times t1 to t4 of the illumination light. In this case, the control unit 36 controls the light receiving time of the imaging unit 23 and the light emission time t1 to the same value when the in-vivo image of the first light emitting condition is captured, controls the light receiving time of the imaging unit 23 and the light emission time t2 to the same value when the in-vivo image of the second light emitting condition is captured, controls the light receiving time of the imaging unit 23 and the light emission time t3 to the same value when the in-vivo image of the third light emitting condition is captured, and controls the light receiving time of the imaging unit 23 and the light emission time t4 to the same value when the in-vivo image of the fourth light emitting condition is captured.

Next, an operation of the control unit 33 for causing the magnetic field generating unit 3 to change a relative image capturing direction F of the capsule endoscope 32 to the subject will be explained. The control unit 33 sets an angular speed ω1 of the external magnetic fields when the magnetic field directions are changed during the period of the image capturing interval T of an in-vivo image and an angular speed ω2 of the external magnetic fields when the magnetic field directions are changed in the image capturing time of respective in-vivo images by repeatedly performing process procedures approximately similar to steps S1 to S4 described above (refer to FIG. 4). The control unit 33 controls the magnetic field generating unit 3 so that it changes the image capturing direction F of the capsule endoscope 32 at the angular speeds ω1, ω2.

In this case, the speed setting unit 33b obtains information (image capturing conditions such as an angle of view θ, a frame rate f, the number of pixels m of one side of an in-vivo image, and the light emission times t1 to t4) as to the imaging function of the capsule endoscope 32 input by the input unit 8 and the numbers of types n of the image capturing conditions at step S101 described above. The speed setting unit 33b calculates the angular speed ω1 [degree/second] less than a divided value obtained by dividing a multiplied value of the angle of view θ and the frame rate f by the number of types m of the image capturing conditions and sets the calculated angular speed ω1 as an average angular speed of the external magnetic fields when the magnetic field directions of the external magnetic fields are changed in the image capturing interval T described above. Further, the speed setting unit 33b calculates the angular speed ω2 [degree/second] less than a divided value obtained by dividing the angle of view θ by a multiplied value of the number of pixels m of one side of the in-vivo image and the emission time of the illumination light and sets the calculated angular speed ω2 as an average angular speed of the external magnetic fields when the magnetic field directions of the external magnetic fields are changed in the image capturing time (for example, a light emission time of illumination light) of respective in-vivo images. The light emission time of the illumination light used for the calculation process of the angular speed ω2 is the maximum value (for example, the light emission time t4 of the light emission times t1 to t4 described above) of a plurality of light emission times which are switched based on the control of the control unit 36 of the capsule endoscope 32 described above.

At step S103, the magnetic field control unit 33a controls the magnetic field generating unit 3 so that it changes the magnetic field directions of the external magnetic fields at the angular speed ω1 (<frame rate f×angle of view θ÷number of types of image capturing conditions) in the image capturing interval T of the imaging unit 23 excluding the image capturing time of an in-vivo image (a light emission time of illumination light or the light receiving time of the imaging unit 23). Further, the magnetic field control unit 33a controls the magnetic field generating unit 3 so that it changes the magnetic field directions of the external magnetic fields at the angular speed ω2 (<angle of view θ÷(number of pixels m of one side×light emission time t4)) in the image capturing time of an in-vivo image in the image capturing interval T of the imaging unit 23, i.e., during the period in which the imaging unit 23 captures the in-vivo image.

Figure 11:
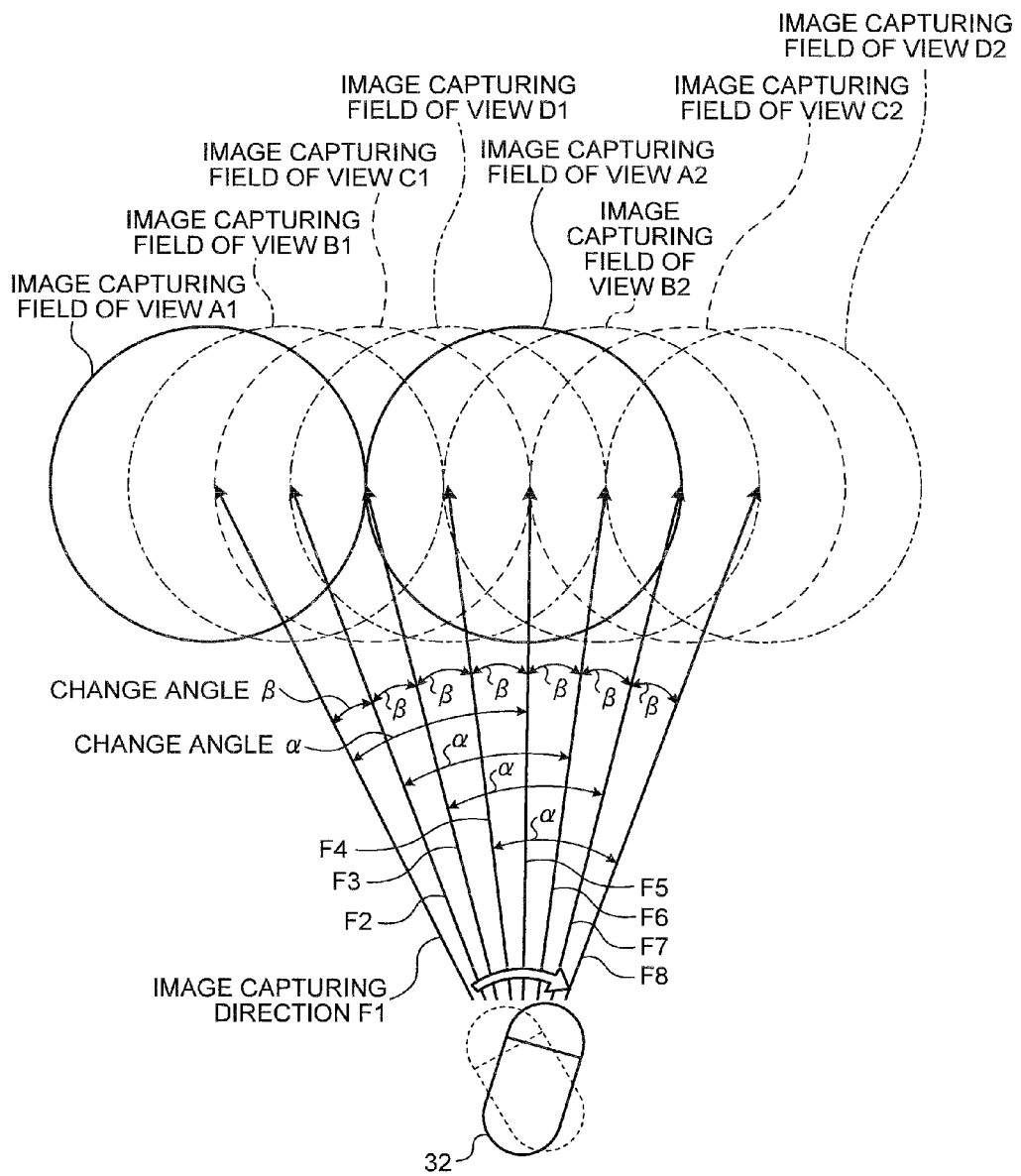
FIG. 11 is a schematic view exemplifying a state in which the capsule endoscope sequentially captures in-vivo images of the plurality of types of the image capturing conditions while changing an image capturing direction following magnetic field directions of external magnetic fields.

Next, how the capsule endoscope 32 in the subject is affected by the external magnetic fields of the magnetic field generating unit 3 whose magnetic field directions are controlled by the control unit 33 described above as well as an in-vivo image capturing step and an image capturing direction change step in the in-vivo observing method according to the invention will be specifically explained by exemplifying a case in which the capsule endoscope 32 in the subject sequentially captures in-vivo images by switching the four types of image capturing conditions (specifically, the four types of the light emission times t1 to t4) in the predetermined order as shown in FIG. 10. FIG. 11 is a schematic view exemplifying a state in which the capsule endoscope 32 sequentially captures in-vivo images of the plurality of types of the image capturing conditions while changing the image capturing direction F following the magnetic field directions of the external magnetic fields.

In FIG. 11, image capturing fields of view A1, A2 are image capturing fields of view illuminated by the illumination light of the light emission time t1 as the minimum value of the four types of the light emission times t1 to t4, image capturing fields of view B1, B2 are image capturing fields of view illuminated by the illumination light of the light emission time t2 larger than the light emission time t1, image capturing fields of view C1, C2 are image capturing fields of view illuminated by the illumination light of the light emission time t3 larger than the light emission time t2, and the image capturing fields of view D1, D2 are image capturing fields of view illuminated by the illumination light of the light emission time t4 larger than the light emission time t3. The image capturing fields of view A1, A2, the image capturing fields of view B1, B2, the image capturing fields of view C1, C2, and image capturing fields of view D1, D2 are image capturing fields of view of the capsule endoscope 32 which catch inside of an organ of the subject and are prescribed by the angle of view θ described above. Any of image capturing directions F1 to F8 is an example of the image capturing direction F of the capsule endoscope 32, and the image capturing directions F1, F5 correspond to the image capturing fields of view A1, A2, respectively, and the image capturing directions F2, F6 correspond to the image capturing fields of view B1, B2, respectively. Further, the image capturing directions F3, F7 correspond to the image capturing fields of view C1, C2, respectively, and the image capturing direction F4, F8 correspond to the image capturing fields of view D1, D2, respectively.

As shown in FIG. 11, the capsule endoscope 32 changes a relative direction (i.e., posture) to the subject following the external magnetic fields of the magnetic field generating unit 3 whose magnetic field directions are controlled by the control unit 33 described above as well as continuously changes the image capturing directions in the order of the image capturing direction F1, the image capturing direction F2, the image capturing direction F3, the image capturing direction F4, the image capturing direction F5, the image capturing direction F6, the image capturing direction F7, and the image capturing direction F8. In this case, the capsule endoscope 32 sequentially repeatedly captures an in-vivo image of a first light emitting condition, an in-vivo image of a second light emitting condition, an in-vivo image of a third light emitting condition, and an in-vivo image of a fourth light emitting condition by changing the image capturing field of view in the order of the image capturing field of view A1, the image capturing field of view B1, the image capturing field of view C1, the image capturing field of view D1, the image capturing field of view A2, the image capturing field of view B2, the image capturing field of view C2, and the image capturing field of view D2 as the image capturing directions change.

The magnetic field generating unit 3 described above changes the magnetic field directions of the external magnetic fields for inducing a change of posture of the capsule endoscope 32 at the angular speed ω1 (<frame rate f×angle of view θ÷number of types n of image capturing conditions) in the image capturing interval T of the capsule endoscope 32 excluding the image capturing time of the in-vivo image based on the control of the magnetic field control unit 33a, and changes the magnetic field directions of the external magnetic fields at the angular speed ω2 (<angle of view θ÷(number of pixels m of one side×light emission time t4) during the period in which the capsule endoscope 32 captures an in-vivo image in the image capturing interval T. The capsule endoscope 32 changes the image capturing directions at the angular speed ω1 in the order of the image capturing directions F1, F2, F3, F4, F5, F6, F7, and F8 following the external magnetic fields which change the magnetic field directions at the angular speeds ω1, ω2. The capsule endoscope 32 changes the image capturing direction at the angular speed ω2 particularly during the respective periods in which in-vivo images are captured.

As described above, when the capsule endoscope 32 changes the image capturing directions by the action of the external magnetic fields of the magnetic field generating unit 3, change angles β [degree] between the respective image capturing directions F1 to F8 are less than a divided value obtained dividing the angle of view θ by the number of types n (=4) of the image capturing conditions of the capsule endoscope 32. That is, the change angle α between the image capturing direction F1 and the image capturing direction F5 which correspond to the image capturing fields of view A1, A2 of the same type of in-vivo images (the in-vivo images of the first light emitting condition), respectively, is four times the change angles β between the respective image capturing directions as shown in FIG. 11 and is less than the angle of view θ at all times. Likewise, any of the change angle α between the image capturing direction F2 and the image capturing direction F6 which correspond to the image capturing fields of view B1, B2 of the in-vivo images of the second light emitting condition, the change angle α between the image capturing direction F3 and the image capturing direction F7 which correspond to the image capturing fields of view C1, C2 of the in-vivo images of the third light emitting condition, and the change angle α between the image capturing direction F4 and the image capturing direction F8 which correspond to the image capturing fields of view D1, D2 of the in-vivo images of the fourth light emitting condition is four times the change angle β and less than the angle of view θ at all times.

When, for example, the frame rate f of the imaging unit 23 of the capsule endoscope 32 is 4 [frame/second], the angle of view is 120 [degree], and the number of types n of the image capturing conditions is 4, the angular speed ω1 in the second embodiment is less than 120 [degree/second], the change angles β between the respective image capturing directions is less than 30 [degree] (=angle of view θ/4) at all times due to the action of the external magnetic fields for changing the magnetic field directions at the angular speed ω1, and the respective change angles α are less than 120 [degree] (=angle of view θ) at all times.

As a result, the image capturing field of view A1 in the image capturing direction F1 overlaps at least a part of a field of view region of the image capturing field of view A2 in the image capturing direction F5 after it is changed, and the image capturing field of view B1 in the image capturing direction F2 overlaps at least a part of a field of view region of the image capturing field of view B2 in the image capturing direction F6 after it is changed. Further, the image capturing field of view C1 in the image capturing direction F3 overlaps at least a part of a field of view region of the image capturing field of view C2 in the image capturing direction F7 after it is changed, and the image capturing field of view D1 in the image capturing direction F4 overlaps at least a part of a field of view region of the image capturing field of view D2 in the image capturing direction F8 after it is changed. The capsule endoscope 32 can capture a group of in-vivo images classified depending on an amount of light emission of the illumination light by overlapping the field of view regions, respectively between the image capturing fields of view A1, A2, the image capturing fields of view B1, B2, the image capturing fields of view C1, C2, and the image capturing fields of view D1, D2 as described above. Further, at least parts of image portions can be securely overlapped between the same type of the in-vivo images of the group of the in-vivo images (specifically, between the in-vivo images of the first light emitting condition, between the in-vivo images of the second light emitting condition, between the in-vivo images of the third light emitting condition, and between the in-vivo images of the fourth light emitting condition). When the capsule endoscope 32 time-sequentially captures a group of in-vivo images of the subject, it can securely obtain a group of continuous in-vivo images in which at least parts of image portions overlap between the in-vivo images having the same type of the image capturing conditions.

It is preferable to set the angular speed ω1 in the second embodiment equal to or less than one-half a divided value obtained by dividing a multiplied value of the angle of view θ and the frame rate f by the number of types n of the image capturing conditions approximately likewise the first embodiment described above. The change angle α between the image capturing directions F1, F5, the change angle α between the image capturing directions F2, F6, the change angle α between the image capturing directions F3, F7, and the change angle α between the image capturing direction F4, F8 are equal to or less than one-half the angle of view θ at all times by setting the angular speed ω1 (≤frame rate f×angle of view θ÷number of types n of image capture conditions÷2) as described above.

When, for example, the frame rate f of the imaging unit 23 of the capsule endoscope 32 is 4 [frame/second], the angle of view θ is 120 [degree], and the number of types n of the image capturing conditions is 4, the angular speed ω1 is equal to or less than 60 [degree/second], and the change angles β between the respective image capturing directions described above are less than 15 [degree] (=angle of view θ/4) at all times and the respective change angles α described above are less than 60 [degree] (=angle of view θ/2) at all times due to the action of the external magnetic fields for changing the magnetic field directions at the angular speed ω1.

As a result, the image capturing field of view A1 in the image capturing direction F1 overlaps a half or more portion of the image capturing field of view A2 in the image capturing direction F5 after it is changed, and the image capturing field of view B1 in the image capturing direction F2 overlaps a half or more portion of the image capturing field of view B2 in the image capturing direction F6 after it is changed. Further, the image capturing field of view C1 in the image capturing direction F3 overlaps a half or more portion of the image capturing field of view C2 in the image capturing direction F7 after it is changed, and the image capturing field of view D1 in the image capturing direction F4 overlaps a half or more portion of the image capturing field of view D2 in the image capturing direction F8 after it is changed. The capsule endoscope 32 can securely capture a group of in-vivo images in which half or more image portions overlap between the in-vivo images having the same type of the image capturing conditions by overlapping half or more image portions between the image capturing fields of view A1, A2, between the image capturing fields of view B1, B2, between the image capturing fields of view C1, C2, and between the image capturing fields of view D1, D2, respective as described above. Even when the center of rotation of the image capturing direction, which rotates following the external magnetic fields, does not agree with the center of the angle of view θ, the capsule endoscope 32 can more securely obtain a group of continuous in-vivo images in a mode in which at least parts of image portions overlap between the in-vivo images having the same type of the image capturing conditions.

The capsule endoscope 32 changes the image capturing direction at the angular speed ω2 following the external magnetic fields of the magnetic field generating unit 3 for changing the magnetic field directions at the angular speed ω2 (<angle of view θ÷(number of pixels m of one side×light emission time t)) during the respective periods of the image capturing interval T in which in-vivo images are captured as described above. The light emission time t4 is the maximum value of the four types of the light emitting conditions (the light emission times t1 to t4). Accordingly, even when the light emission times t1 to t4 of the illumination light are sequentially switched (that is, even when the amount of light emission of the illumination light is sequentially switched), the respective amounts of offset of field of view of the image capturing fields of view A1, A2, B1, B2, C1, C2, D1, and D2, which are offset following the external magnetic fields for changing the magnetic field directions at the angular speed ω2, are an amount of offset less than one pixel of the light receiving surface of the imaging unit 23 at all times. As a result, even when the capsule endoscope 32 captures in-vivo images as well as changes the image capturing directions by changing them at the angular speed ω2 during the respective periods in which the in-vivo images of the plurality of types of the image capturing conditions are captured, it can reduce an image fluctuation of a group of in-vivo images of the plurality of types of the image capturing conditions and can sequentially capture the group of in-vivo images of the plurality of types of the image capturing conditions vividly approximately likewise the first embodiment described above.

As explained above, in the second embodiment of the invention, the plurality of types of the image capturing conditions, under which the imaging unit captures in-vivo images, are sets. The plurality of types of the image capturing conditions are switched in the predetermined order, and the in-vivo images of the plurality of types of the image capturing conditions are sequentially captured. The magnetic field directions of the external magnetic fields are changed at the angular speed, which is less than a divided value obtained by dividing a multiplied value of the frame rate and the angle of view by the number of types of the image capturing conditions, and the image capturing direction of the imaging unit following the magnetic field directions of the external magnetic fields is changed at the angular speed. The other arrangements of the first embodiment is the same as those of the first embodiment described above. Accordingly, the change angle of the image capturing direction, in which the same type of the image capturing conditions is repeated, of the respective image capturing directions of the group of the plurality of types of the in-vivo images, can be kept less than the angle of view of the imaging unit during the periods of the respective image capturing intervals of the plurality of types of the in-vivo images classified depending on the plurality of types of the image capturing conditions so that at least parts of the field of view regions can be overlapped each other between the respective image capturing fields of view, in which the same type of the image capturing conditions is repeated, in the respective image capturing fields of view which are offset by changing the image capturing direction. As a result, there can be realized an in-vivo observing system and an in-vivo image acquisition device as well as an in-vivo observing method for observing inside of an organ of a subject by observing the group of the in-vivo images, the system, the device and the method being capable of obtaining the same operation/working effect as that of the first embodiment described above as well as securely obtaining a group of continuous in-vivo images which are continuous in time in a mode in which at least parts of image portions overlap between the in-vivo images having the same type of the image capturing conditions.

Uncaptured portions inside of an organ of the subject can be reduced as much as possible using the in-vivo observing system and the in-vivo image obtaining device according to the second embodiment. Further, in-vivo images having various amounts of light in conformity with a relative distance between an inner wall portion of an organ, which varies in an organ such as a stomach or a large intestine that forms a relatively large space, and the imaging unit, can be continuously and sequentially captured according to each amount of light. As a result, the in-vivo images, which are continuous in time, can be classified depending on an amount of light as well as an inside of an organ of the subject can be vividly observed without remaining unobserved portion.

When the in-vivo observing system and the in-vivo image acquisition device according to the second embodiment of the invention have one type of the in-vivo image capturing conditions (i.e., number of types n of image capturing conditions=1), they are the same as the in-vivo observing system and the in-vivo image acquisition device according to the first embodiment.

Third Embodiment

Next, a third embodiment of the invention will be explained. The first embodiment described above changes the image capturing direction F of the capsule endoscope 2 following the magnetic field directions of the external magnetic fields by changing the magnetic field directions of the external magnetic fields applied to the magnet 28 of the capsule endoscope 2. However, in the third embodiment, a posture of a subject on a placing unit such as a bed on which the subject is placed is changed by driving the placing unit to thereby change the image capturing direction of the capsule endoscope in the subject relatively with respect to the subject.

Figure 12:
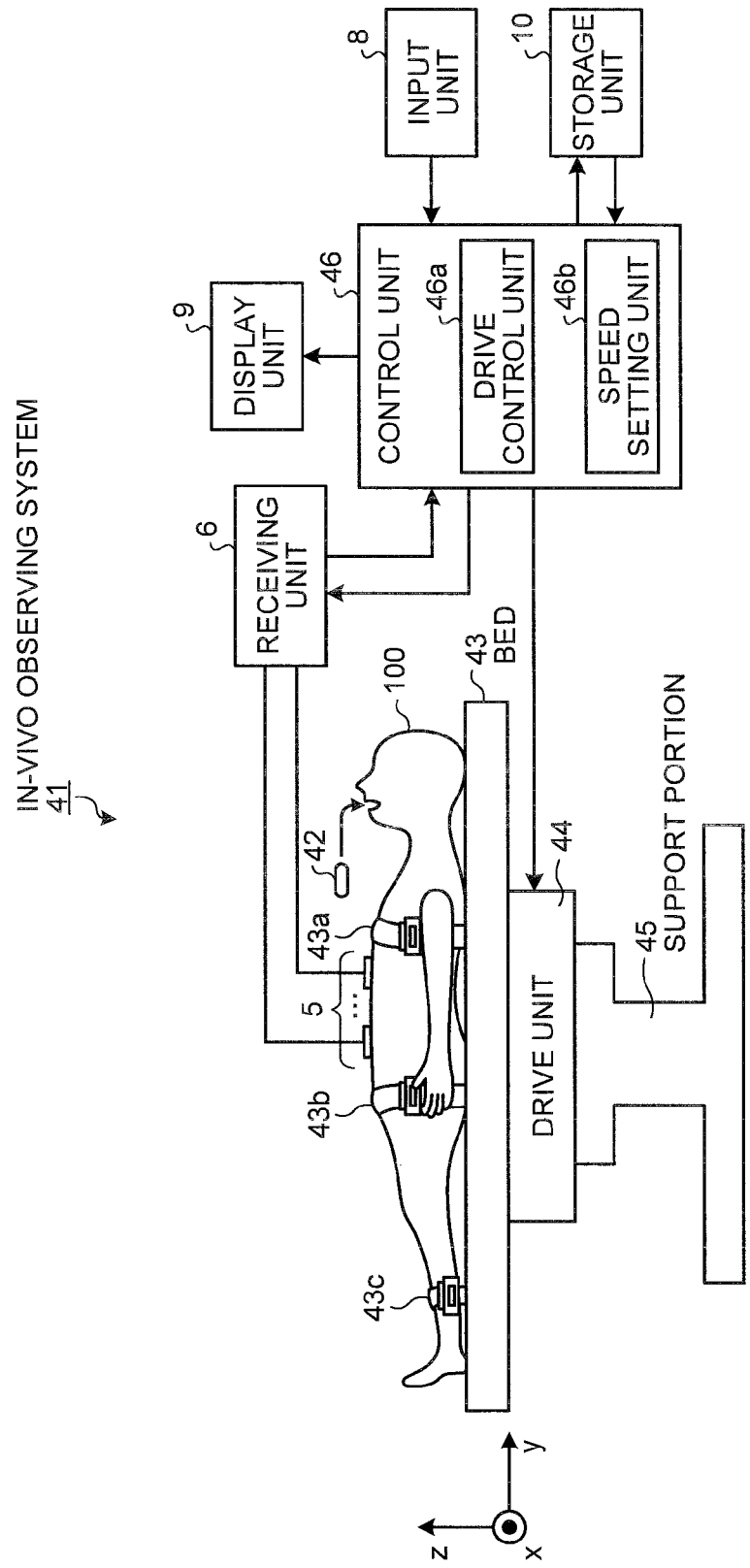
FIG. 12 is a block diagram schematically showing an arrangement example of an in-vivo observing system according to a third embodiment of the invention.

FIG. 12 is a block diagram schematically showing an arrangement example of an in-vivo observing system according to the third embodiment of the invention. As shown in FIG. 12, an in-vivo observing system 41 according to the third embodiment includes a capsule endoscope 42, which can float on a liquid, in place of the capsule endoscope 2 of the in-vivo observing system 1 according to the first embodiment described above and a control unit 46 in place of the control unit 11. Further, the in-vivo observing system 41 does not include the magnetic field generating unit 3, the coil power supply 4, and the position and posture detection unit 7 described above and includes a bed 43 for placing a subject 100 thereon, into an organ of which the capsule endoscope 42 is introduced, a drive unit 44 for changing the posture of the subject 100 by driving the bed 43, and a support portion 45 for supporting the bed 43 and the drive unit. The other arrangements are the same as those of the first embodiment, and the same reference numerals are given to the same components.

The capsule endoscope 42 has a specific gravity smaller than that of the liquid (for example, water, normal saline, or the like) introduced into an organ of the subject and sequentially captures in-vivo images of the subject while keeping a specific floating posture on a liquid surface of the liquid. After the capsule endoscope 42 is introduced into the organ of the subject 100, it float on the liquid surface in the organ, and relatively changes an image capturing direction of an in-vivo image with respect to the subject 100 by changing the posture of the subject 100 placed on the bed 43 in place of changing the image capturing direction following the external magnetic fields described above. The other functions and the structure of the capsule endoscope 42 are the same as those of the capsule endoscope 2 according to the first embodiment described above. An arrangement of the capsule endoscope 42 will be described later.

The bed 43 acts as a placing unit for placing the subject 100 thereon, into the organ of which the capsule endoscope 42 is introduced. Specifically, an xyz coordinate system is prescribed on the bed 43 as shown in FIG. 12, and the subject 100 is placed in a space of the xyz coordinate system. Further, the bed 43 has belts 43a, 43b, and 43c. The belts 43a, 43b, 43c bind the subject 100 placed on the bed 43 to thereby prevent the subject 100 from dropping from the bed 43 when the posture thereof is changed.

The drive unit 44 acts as a direction change unit for changing the image capturing direction of the capsule endoscope 42 in the subject 100 placed on the bed 43. Specifically, the drive unit 44 rotates the bed 43 about the axes of the xyz coordinate system (for example, about an x-axis and a y-axis) based on the control of the control unit 46 and changes the posture of the subject 100 on the bed 43. With this operation, the drive unit 44 relatively changes the image capturing direction of the capsule endoscope 42 which floats on the liquid surface in the organ of the subject 100.

The control unit 46 includes a drive control unit 46a and a speed setting unit 46b and controls the relative posture of the capsule endoscope 42 to the subject 100 on the bed 43 by controlling the drive unit 44 in place of controlling the external magnetic fields of the magnetic field generating unit 3 by controlling an amount of alternating current supplied from the coil power supply 4 likewise the control unit 11 of the first embodiment described above. The speed setting unit 46b calculates an angular speed appropriately using information (for example, a frame rate, an angle of view, the number of pixels of one side of an in-vivo image, and capturing conditions) as to an imaging function of the capsule endoscope 42 input by the input unit 8 and sets the calculated angular speed as an angular speed when the bed 43 is rotated about the axes of the xyz coordinate system described above. The drive control unit 46a causes the drive unit 44 to rotate the bed 43 at the angular speed set by the speed setting unit 46b and controls the relative posture of the capsule endoscope 42 to the subject 100 on the bed 43 through the drive control of the drive unit 44. As a result, the drive control unit 46a causes the drive unit 44 to relatively change the image capturing direction of the capsule endoscope 42 in the subject 100 with respect to the subject 100. The control unit 46 has an image processing function similar to that of the control unit 11 of the in-vivo observing system 1 according to the first embodiment described above and controls the receiving unit 6, the input unit 8, the display unit 9, and the storage unit 10 likewise the control unit 11.

Figure 13:
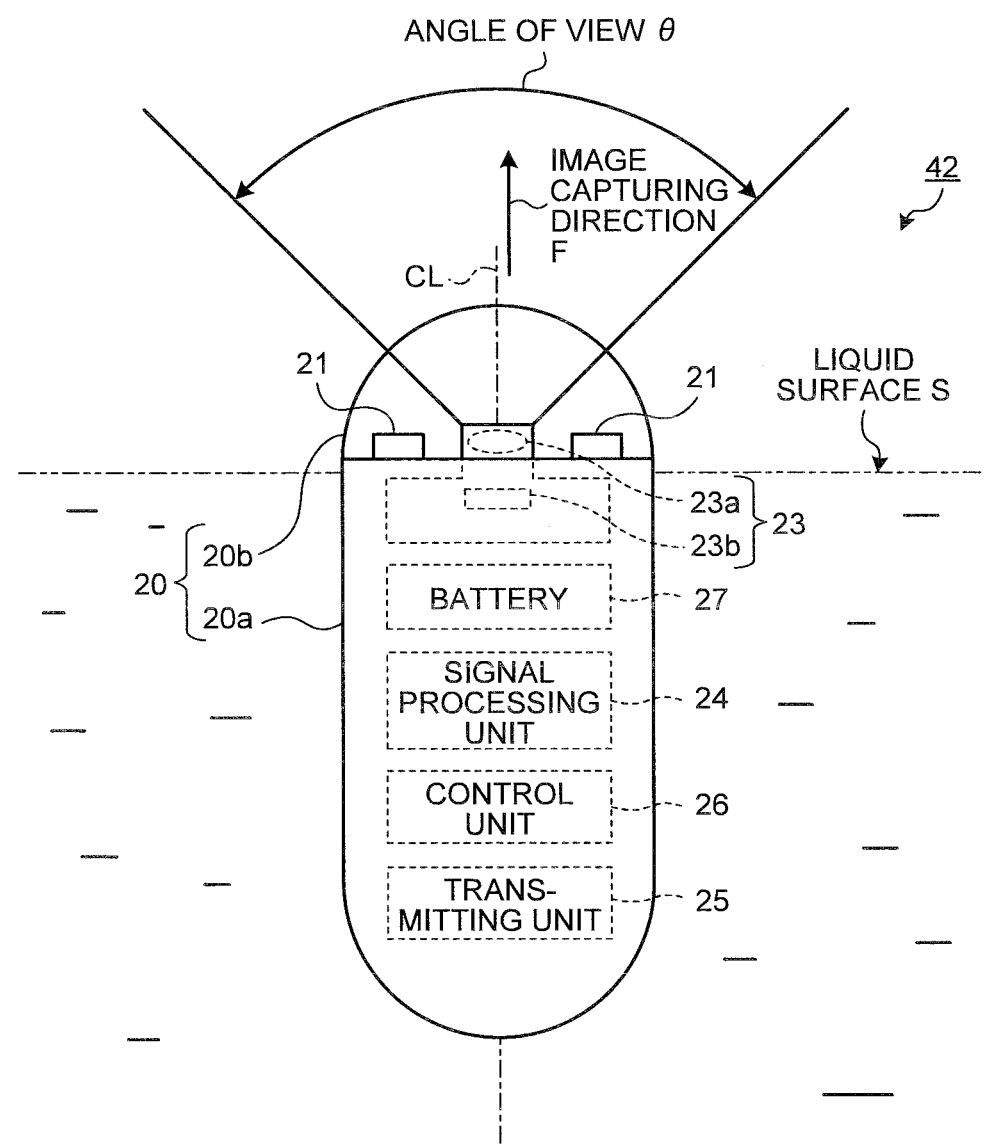
FIG. 13 is a schematic view showing an arrangement example of a capsule endoscope according to the third embodiment of the invention.

Next, the arrangement of the capsule endoscope 42 as an example of an in-vivo image acquisition device according to the third embodiment of the invention will be explained in detail. FIG. 13 is a schematic view showing an arrangement example of the capsule endoscope 42 according to the third embodiment of the invention. As shown in FIG. 13, the capsule endoscope 42 according to the third embodiment does not include the magnet 28 of the capsule endoscope 2 according to the first embodiment described above. The capsule endoscope 42 has the specific gravity smaller than that of the liquid introduced into the organ of the subject 100 and floats on the liquid surface S of the liquid in the organ of the subject 100. Further, the capsule endoscope 42 has a center of gravity at a position out of the center of the casing 20 and keeps a specific floating posture prescribed by the center of gravity in the state that it floats on the liquid surface S. The other arrangements are the same as those of the first embodiment, and the same reference numerals are given to the same components.

The capsule endoscope 42, which keeps the specific floating posture on the liquid surface S, causes the image capturing direction F to face a predetermined direction (for example, an upper vertical direction) to the liquid surface S. The image capturing direction F is relatively changed with respect to the subject 100 by changing the posture of the subject 100 on the liquid surface S in a state that the capsule endoscope 42 is floated on the liquid surface S in the organ by rotating the bed 43 on which the subject 100 is placed.

Next, an operation of the control unit 46 for causing the drive unit 44 to change the relative image capturing direction F of the capsule endoscope 42 to the subject 100 will be explained. The control unit 46 sets an angular speed ω1 when the bed 43 is rotated in the period of an image capturing interval T of an in-vivo image and an angular speed ω2 when the bed 43 is rotated in the image capturing time of the in-vivo images by repeatedly executing a process procedure approximately similar to steps S101 to S103 described above (refer to FIG. 4). Then, the control unit 46 controls the drive unit 44 so that it relatively changes the image capturing direction F of the capsule endoscope 42 in the subject 100 with respect to the subject 100 at the set angular speeds ω1, ω2.

In this case, the control unit 46 sets an angular speed at which the bed 43 is rotated in place of step S101 described above. Specifically, the speed setting unit 46b obtains the information (image capturing conditions such as an angle of view θ, a frame rate f, the number of pixels m of one side of an in-vivo image, and a light emission time t) as to the imaging function of the capsule endoscope 42 input by the input unit 8. The speed setting unit 11b calculates the angular speed ω1 [degree/second] less than a multiplied value of the angle of view θ and the frame rate f and sets the calculated angular speed ω1 as an average angular speed of the bed 43 when the posture of the subject 100 on the bed 43 is changed in the image capturing interval T described above. Further, the speed setting unit 46b calculates the angular speed ω2 [degree/second] less than a divided value obtained by dividing the angle of view θ by a multiplied value of the number of pixels m of the one side of the in-vivo image and the light emission time t of illumination light and sets the calculated angular speed ω2 as an average angular speed of the bed 43 when the posture of the subject 100 on the bed 43 is changed in the image capturing time of respective in-vivo images (for example, a light emission time of illumination light).

The control unit 46 causes the drive unit 44 to rotate the bed 43 at the angular speeds ω1, ω2 in place of step S103 described above. Specifically, the drive control unit 46a controls the drive unit 44 so that it rotates the bed 43 about the axes of the xyz coordinate system at the angular speed ω1 (<frame rate f×angle of view θ) in the image capturing interval T of the imaging unit 23 excluding an image capturing time of an in-vivo image (a light emission time of the illumination light or a light receiving time of the imaging unit 23). Further, the drive control unit 46a controls the drive unit 44 so that it rotates the bed 43 about the axes of the xyz coordinate system at the angular speed ω2 (<angle of view θ÷(number of pixels m of one side×light emission time t)) in the image capturing time of the in-vivo images in the image capturing interval T of the imaging unit 23, i.e., during the period in which the imaging unit 23 captures in-vivo images.

Figure 14:
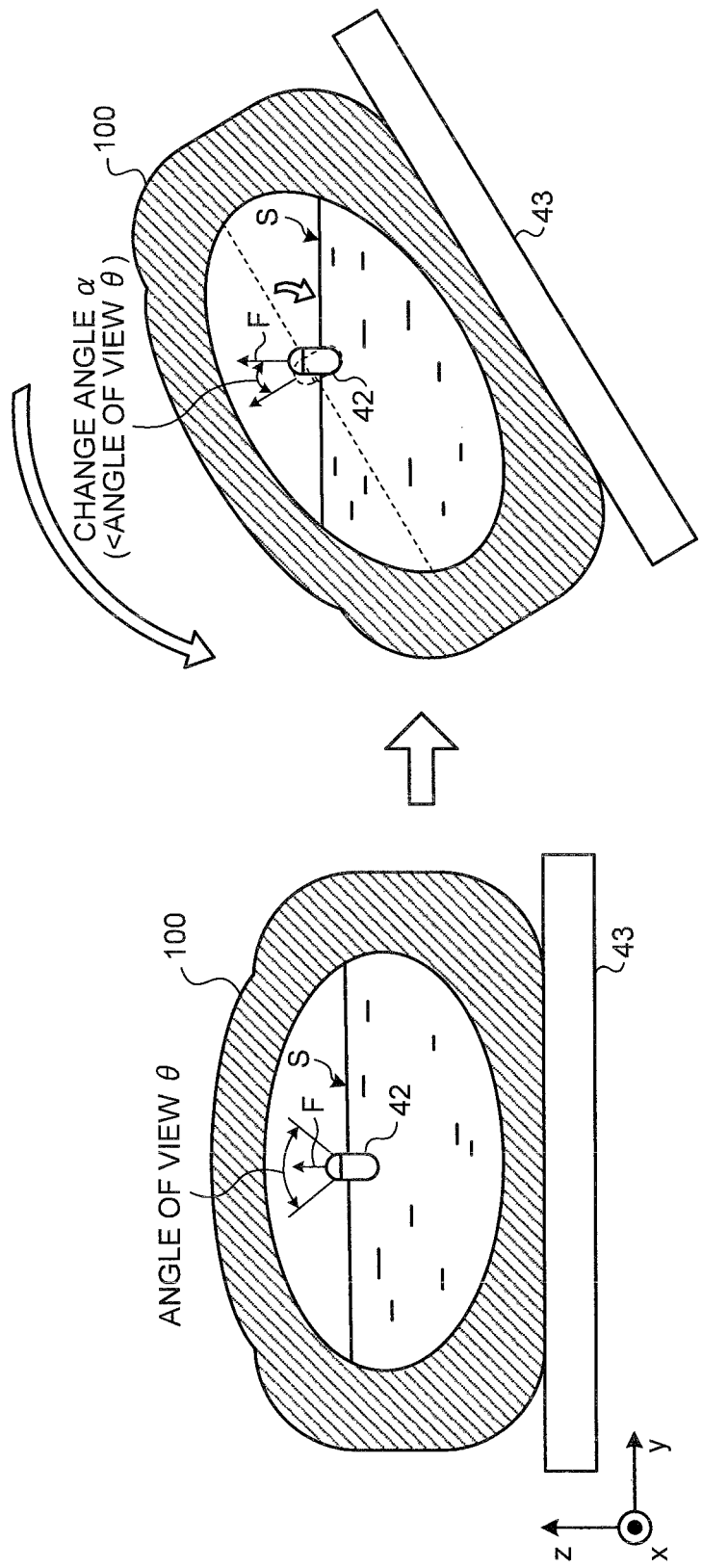
FIG. 14 is a schematic view exemplifying a state in which the capsule endoscope sequentially captures in-vivo images while changing an image capturing direction relatively with respect to a subject due to the rotation of a bed.

Next, how the capsule endoscope 32 in the subject is affected by the bed 43 rotated by the drive unit 44 controlled by the control unit 46 described above as well as an in-vivo image capturing step and an image capturing direction change step in the in-vivo observing method according to the invention will be specifically explained by exemplifying a case in which the capsule endoscope 42, which floats on the liquid surface S in an organ of the subject 100, sequentially captures in-vivo images while causing the image capturing direction F to face vertically upward to the liquid surface S. FIG. 14 is a schematic view exemplifying a state in which the capsule endoscope sequentially captures in-vivo images while relatively changing the image capturing direction with respect to the subject 100 due to the rotation of the bed 43 on which the subject 100 is placed.

As shown in FIG. 14, the capsule endoscope 42 floats on the liquid surface S in the organ of the subject 100 (for example, a stomach and the like) as well as keeps a specific floating posture and faces the image capturing direction F vertically upward to the liquid surface S. As the bed 43 is rotated (for example, rotated about the y-axis) by the drive unit 44 that is controlled by the control unit 46 described above, the capsule endoscope 42 in the floating state changes a relative direction (i.e., posture) to the subject 100 on the bed 43 as well as sequentially captures in-vivo images of an image capturing field of view which is relatively offset to the subject 100. In this case, the capsule endoscope 42 relatively changes the image capturing direction F with respect to the subject 100 as the bed 43 is rotated while causing the image capturing direction F to face vertically upward to the liquid surface S in the organ.

The drive unit 44 described above rotates the bed 43 on which the subject 100 is placed at the angular speed $\omega 1$ (<frame rate f×angle of view $\theta$) in the image capturing interval T of the imaging unit 23 excluding the image capturing time of the in-vivo image based on the control of the drive control unit 46a and rotates the bed 43 at the angular speed $\omega 2$ (<angle of view $\theta$÷(number of pixels m of one side×light emission time t)) during the period in which the capsule endoscope 42 captures in-vivo images in the image capturing interval T. As the bed 43 is rotated at the angular speeds $\omega 1$, $\omega 2$, the capsule endoscope 42 relatively changes the image capturing direction F at the angular speed $\omega 1$ with respect to the subject 100 and in particular relatively changes the image capturing direction F at the angular speed $\omega 2$ with respect to the subject 100 during the respective periods in which it captures in-vivo images.

When the capsule endoscope 42 relatively changes the image capturing direction F with respect to the subject 100 by the rotating operation of the bed 43, the change angle $\alpha$ [degree] of the image capturing direction F is less than the angle of view $\theta$ of the capsule endoscope 42 at all times as shown in FIG. 14. As a result, the image capturing field of view in the image capturing direction F overlaps at least a part of the field of view region of the image capturing field of view in the image capturing direction F after it is changed. The capsule endoscope 42 can securely capture a group of in-vivo images in which at least parts of image portions overlap between in-vivo images by sequentially capturing in-vivo images while overlapping the field of view regions of the image capturing field of view as described above. When the capsule endoscope 42 time-sequentially captures a group of in-vivo images of the subject, it can securely obtain a group of continuous in-vivo images in which at least parts of image portions overlap between the in-vivo images adjacent to each other in time.

It is preferable to set the angular speed $\omega 1$ in the third embodiment equal to or less than one-half a multiplied value of the angle of view $\theta$ and the frame rate f likewise the first embodiment described above. The change angle $\alpha$ between the respective image capturing directions is equal to or less than one-half the angle of view $\theta$ at all times by setting the angular speed $\omega 1$ (≤frame rate f×angle of view $\theta$÷2) as described above. As a result, the image capturing field of view in the image capturing direction F overlaps a half or more portion of the image capturing field of view in the image capturing direction F after it is changed. The capsule endoscope 42 can securely capture a group of in-vivo images in which half or more image portions overlap between the in-vivo images by overlapping the one-half or more field of view regions between the respective image capturing fields of view as described above. Even when the center of rotation of the image capturing direction F does not agree with the center of the angle of view $\theta$, the capsule endoscope 42 can more securely obtain a group of continuous in-vivo images in which at least parts of image portions overlap between the in-vivo images adjacent to each other in time.

As the bed 43 is rotated at the angular speed $\omega 2$ (<angle of view $\theta$÷(number of pixels m of one side×light emission time t)), the capsule endoscope 42 relatively changes the image capturing direction F at the angular speed $\omega 2$ during the respective periods, in which it captures in-vivo images, in the image capturing interval T as described above. Accordingly, an amount of offset of field of view of the image capturing field of view, which is offset following the image capturing direction F changed at the angular speed $\omega 2$, is less than one pixel of a light receiving surface of the imaging unit 23 at all times. As a result, the capsule endoscope 42 captures in-vivo images by changing the image capturing direction F at the angular speed $\omega 2$ during the respective periods in which it captures in-vivo images likewise the first embodiment described above as well as can sequentially capture vivid in-vivo images whose image fluctuation is reduced.

As explained above, in the third embodiment of the invention, the imaging unit is fixedly arranged in a capsule casing formed in a size which can be easily introduced into the body of a subject. The specific gravity of the capsule endoscope having the capsule casing and the imaging unit is set smaller than that of the liquid introduced into the body of the subject, and the capsule endoscope is floated on the liquid surface of the liquid. The center of gravity of the capsule endoscope is set at the position out of the center of the capsule casing, and the capsule endoscope is caused to keep the specific floating posture on the liquid surface of the liquid. Further, the imaging unit is faced in the predetermined image capturing direction to the liquid surface, and the image capturing direction is relatively changed with respect to the subject by rotating the placing unit (for example, the bed 43 described above), on which the subject is placed who is in the state that the capsule endoscope is floated on the liquid surface in the organ of the subject, at the angular speed less than a multiplied value of the angle of view and the frame rate of the imaging unit. Accordingly, the change angle of the image capturing direction which relatively changes with respect to the subject can be kept less than the angle of view of the imaging unit during the period of the image capturing interval in which in-vivo images are sequentially captured by the imaging unit so that at least parts of the field of view regions of the respective capturing fields of view, which are offset by changing the image capturing direction, can be overlapped each other. As a result, there can be realized an in-vivo observing system and an in-vivo image acquisition device, which can securely obtain a group of continuous in-vivo images in which at least parts of image portions overlap between the in-vivo images adjacent to each other in time as well as an in-vivo observing method, which observes inside of an organ of a subject by observing the group of the in-vivo images, likewise the first embodiment described above.

Uncaptured portions inside of the organ of the subject can be reduced as much as possible as well as a group of continuous in-vivo images can be obtained over approximately the entire region inside of the organ using the in-vivo observing system and the in-vivo image obtaining device according to the third embodiment. As a result, insides of organs such as a stomach and a large intestine of the subject can be entirely observed.

Further, during the period in which an in-vivo image of one frame is captured, the placing unit of the subject is rotated at the angular speed less than a divided value obtained by dividing the angle of view of the imaging unit by a multiplied value of the number of pixels of one side of the in-vivo image and the image capturing time, and the image capturing direction of the imaging unit is relatively changed with respect to the subject at the angular speed. Accordingly, an amount of offset of field of view of the image capturing field of view of the imaging unit, which is offset by the change of the image capturing direction in the image capturing time of the in-vivo image, can be kept less than the amount of offset of one pixel of an in-vivo image. An image fluctuation of the in-vivo image of the image capturing field of view can be reduced to less than one pixel of the light receiving surface of the imaging unit or less than one pixel of a display system of an in-vivo image. As a result, even when an in-vivo image is captured as well as the image capturing direction is changed, vivid images whose image fluctuation is reduced can be sequentially captured.

Fourth Embodiment

Next, a fourth embodiment of the invention will be explained. In the third embodiment described above, the image capturing direction F of the capsule endoscope 42 is relatively changed with respect to the subject 100 by rotating the bed 43 on which the subject 100 is placed. In the fourth embodiment; however, an image capturing direction F of the imaging unit 23 is changed by rotating the imaging unit 23 in a capsule endoscope in place of rotating the bed 43.

Figure 15:
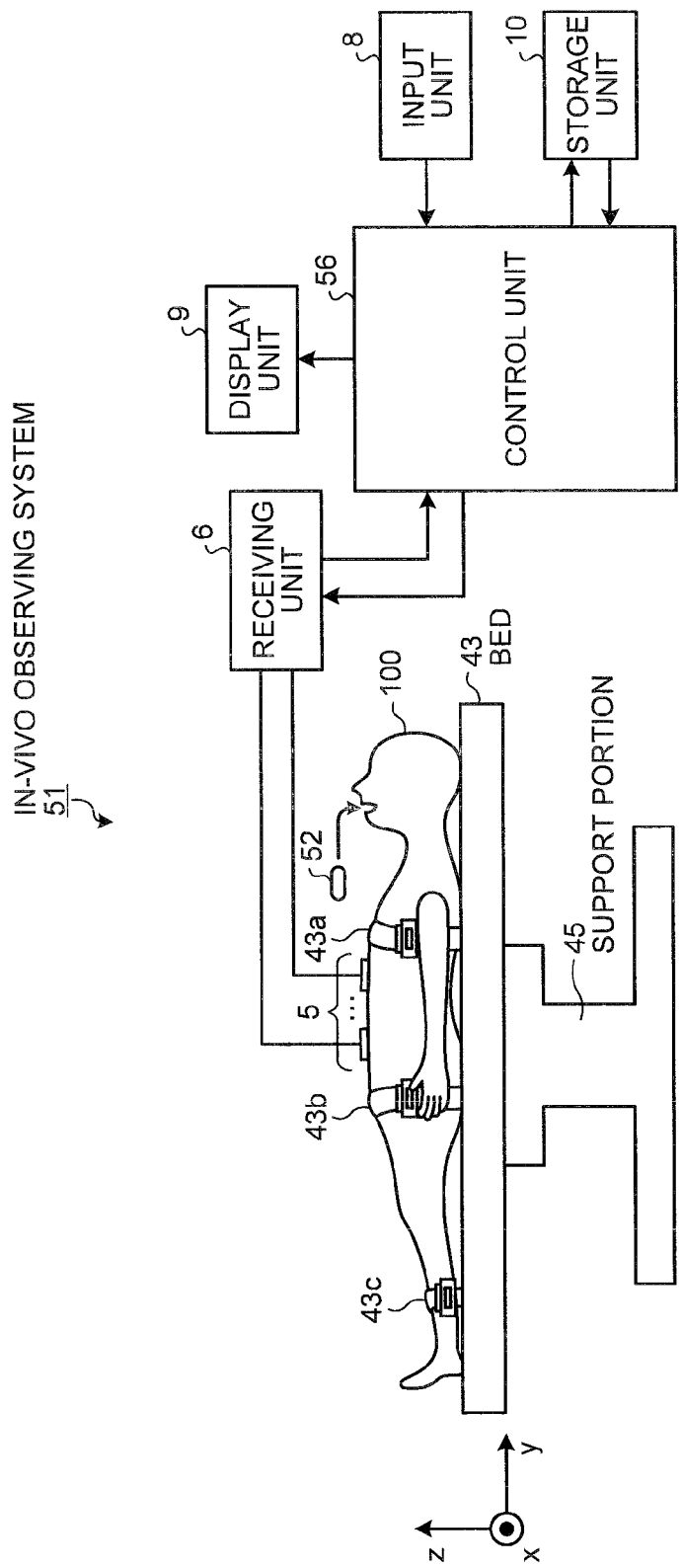
FIG. 15 is a block diagram schematically showing an arrangement example of an in-vivo observing system according to a fourth embodiment of the invention.

FIG. 15 is a block diagram schematically showing an arrangement example of an in-vivo observing system according to the fourth embodiment of the invention. As shown in FIG. 15, an in-vivo observing system 51 according to the fourth embodiment includes a capsule endoscope 52 in place of the capsule endoscope 42 of the in-vivo observing system 41 according to the third embodiment described above and a control unit 56 in place of the control unit 46. The capsule endoscope 52 has a function for changing the image capturing direction by itself without depending on the control unit 56 disposed to the outside the subject 100. Further, the in-vivo observing system 51 does not include the drive unit 44 described above. That is, in the in-vivo observing system 51, the bed 43 does not change a posture of the subject 100 by rotating about the axes of an xyz coordinate system and is fixed by the support portion 45. The other arrangements are the same as those of the third embodiment, and the same reference numerals are given to the same components.

The capsule endoscope 52 changes the image capturing direction of an in-vivo image by itself without depending on the control of the control unit 56 disposed to the outside of the subject 100 as described above. For example, the capsule endoscope 52 is set with a specific gravity and a center of gravity likewise the capsule endoscope 41 of the third embodiment described above, floats on a liquid surface of a liquid introduced into an organ of the subject 100 as well as keeps a specific floating posture on the liquid surface. The capsule endoscope 52 changes the image capturing direction by itself as well as sequentially captures in-vivo images of the subject in a state that it keeps the specific floating posture. The other functions of the capsule endoscope 52 and the structure of the capsule endoscope 52 are the same as those of the capsule endoscope 42 according to the third embodiment described above.

Note that the capsule endoscope 52 need not particularly float on the liquid surface in the subject 100. That is, the specific gravity of the capsule endoscope 52 may be larger than a specific gravity of the liquid introduced into the organ of the subject 100. In this case, it is sufficient to set the center of gravity of the capsule endoscope 52 at a specific position in a capsule casing (the casing 20 shown in FIG. 16 described later), and it is not necessary to set the center of gravity to a position out of the center of the casing 20.

The control unit 56 controls the receiving unit 6, the input unit 8, the display unit 9, and the storage unit 10 likewise the control unit 46 of the in-vivo observing system 41 according to the third embodiment described above. In contrast, the control unit 56 does not have a function for controlling a change of the image capturing direction of the capsule endoscope 52. In this case, it is sufficient for the input unit 8 to input instruction information for instructing the control unit 56, patient information of the subject, examination information of the subject, and the like to the control unit 56, and the input unit 8 need not input information as to an imaging function of the capsule endoscope 52 such as a frame rate, an angle of view, the number of pixels of one side of an in-vivo image, image capturing conditions and the like to the control unit 56.

In the fourth embodiment, since the bed 43, on which the subject 100 is placed, does not change the posture of the subject 100 by rotating about the axes of the xyz coordinate system, it is not necessary to bind the subject 100 with the belts 43a, 43b, 43c described above. That is, the bed 43 need hot include the belts 43a, 43b, 43c.

Figure 16:
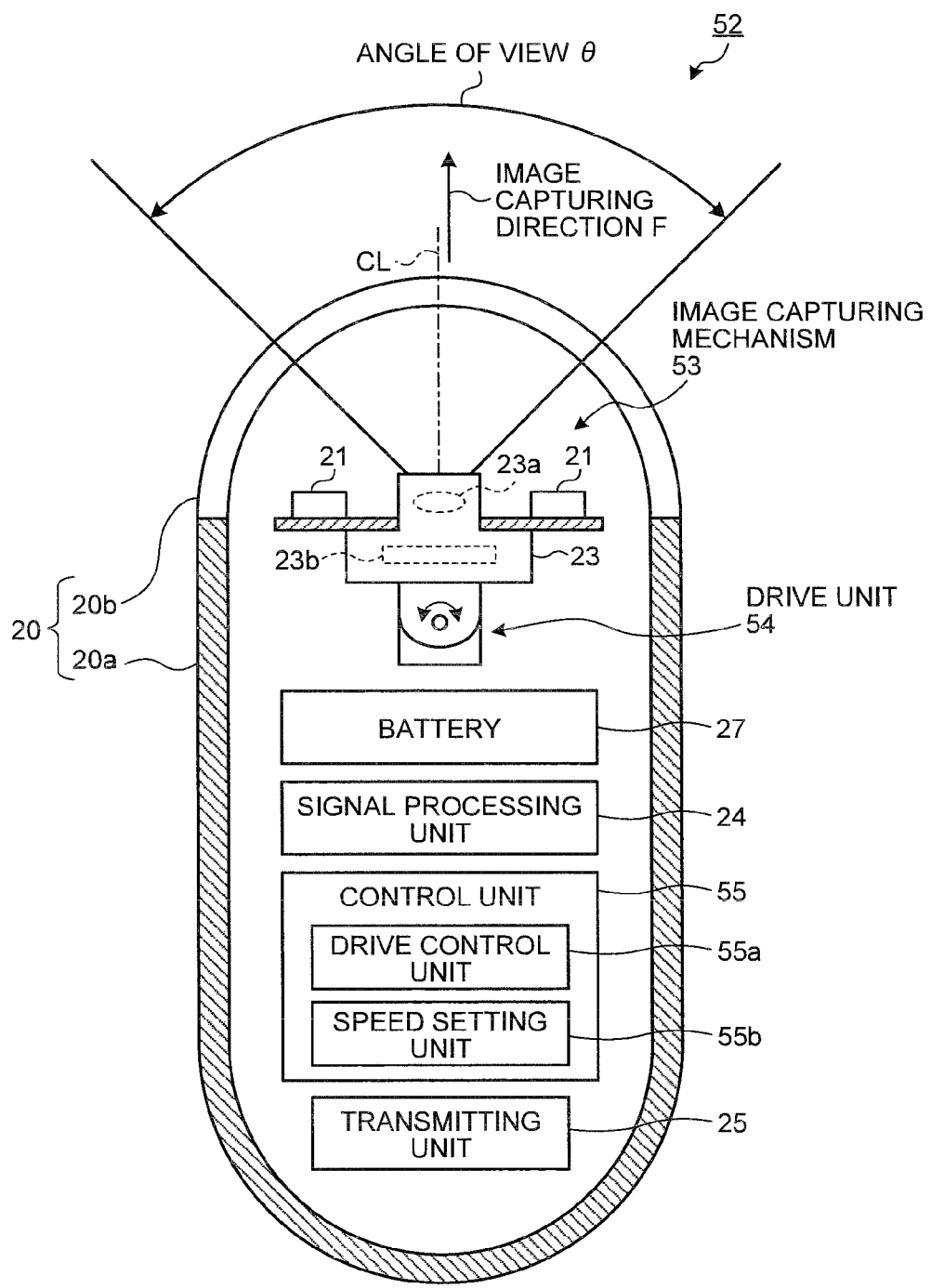
FIG. 16 is a schematic view showing an arrangement example of a capsule endoscope according to the fourth embodiment of the invention.

Next, an arrangement of the capsule endoscope 52 as an example of an in-vivo image acquisition device according to the fourth embodiment of the invention will be explained in detail. FIG. 16 is a schematic view showing an arrangement example of the capsule endoscope 52 according to the fourth embodiment of the invention. As shown in FIG. 16, the capsule endoscope 52 according to the fourth embodiment further includes a drive unit 54 for changing the image capturing direction F of the imaging unit 23 and includes a control unit 55 having a drive control function of the drive unit 54 in place of the control unit 26 of the capsule endoscope 42 according to the third embodiment described above. The drive unit 54 changes the image capturing direction F of the imaging unit 23 by rotating an image capturing mechanism 53 including a plurality of illuminating units 21 and the imaging unit 23. The other arrangements are the same as those of the third embodiment, and the same reference numerals are given to the same components.

The drive unit 54 acts as a direction change unit for changing the image capturing direction F of the imaging unit 23 by rotating at least the imaging unit 23. Specifically, the drive unit 54 changes (rotates) the image capturing direction F while securing radiation of illumination light to an image capturing field of view in the image capturing direction F (i.e., illumination of the image capturing field of view by the illumination light) by rotating the image capturing mechanism 53 including the illuminating units 21 and the imaging unit 23. The drive unit 54 sequentially changes the image capturing direction F even if the capsule endoscope 52 in the subject 100 is in a relative rest state with respect to the subject 100.

The control unit 55 includes a drive control unit 55a and a speed setting unit 55b and controls the image capturing direction F of the capsule endoscope 52 by controlling the drive unit 54 described above. The speed setting unit 55b previously obtains information as to the imaging function of the capsule endoscope 52 (image capturing conditions, for example, a frame rate f, an angle of view θ, the pixel numbers m of one side of an in-vivo image, a light emission time t, and the like) and calculates an angular speed appropriately using the obtained information. The speed setting unit 55b sets the calculated angular speed as an angular speed when the image capturing mechanism 53 is rotated (that is, the image capturing direction F is rotated) by the drive unit 54 described above. The drive control unit 55a causes the drive unit 54 to rotate the image capturing mechanism 53 at the angular speed set by the speed setting unit 55b to thereby cause the drive unit 54 to change the image capturing direction F of the imaging unit 23. That is, the drive control unit 55a controls the image capturing direction F of the imaging unit 23 through the drive control the drive unit 54. The other functions of the control unit 55 are the same as those of the control unit 26 of the capsule endoscope 42 according to the third embodiment described above.

Next, an operation of the control unit 55 of the capsule endoscope 52 for causing the drive unit 54 to change the image capturing direction F of the imaging unit 23 for sequentially capturing in-vivo images of the subject 100 will be explained. The control unit 55 sets an angular speed ω1 when the image capturing mechanism 53 is rotated in the period of an image capturing interval T of in-vivo images and an angular speed ω2 when the image capturing mechanism 53 is rotated in the image capturing time of the in-vivo images by repeatedly executing a process procedure approximately similar to steps S101 to S103 described above and controls the drive unit 54 so that it changes the image capturing direction F at the set angular speeds ω1 and ω2 (refer to FIG. 4).

In this case, the control unit 55 sets the angular speed at which the image capturing mechanism 53 is rotated in place of step S101 described above. Specifically, the speed setting unit 55b previously obtains the information (the image capturing conditions such as the angle of view θ, the frame rate f, the number of pixels m of the one side of the in-vivo image, and the light emission time t) as to the imaging function of the capsule endoscope 52. The speed setting unit 55b calculates the angular speed ω1 [degree/second] less than a multiplied value of the angle of view θ and the frame rate f and sets the calculated angular speed ω1 as the angular speed when the image capturing mechanism 53 is rotated in the image capturing interval T described above. Further, the speed setting unit 55b calculates the angular speed ω2 [degree/second] less than a divided value obtained by dividing the angle of view θ by a multiplied value of the number of pixels m of one side of the in-vivo image and the light emission time t of the illumination light and sets the calculated angular speed ω2 as the angular speed when the image capturing mechanism 53 is rotated in the image capturing time (for example, a light emission time of illumination light) of respective in-vivo images.

The control unit 46 causes the drive unit 54 to rotate the image capturing mechanism 53 at the angular speeds ω1, ω2 in place of step S103 described above. Specifically, the drive control unit 55a controls the drive unit 54 so that it rotates the image capturing mechanism 53 at the angular speed ω1 (<frame rate f×angle of view θ) in the image capturing interval T of the imaging unit 23 excluding an image capturing time of an in-vivo image (a light emission time of illumination light or the light receiving time of the imaging unit 23). Further, the drive control unit 55a controls the drive unit 54 so that it rotates the image capturing mechanism 53 at the angular speed ω2 (<angle of view θ÷(number of pixels m of one side×light emission time t)) in the image capturing time of the in-vivo images in the image capturing interval T of the imaging unit 23, that is, during the period in which the imaging unit 23 captures in-vivo images.

Figure 17:
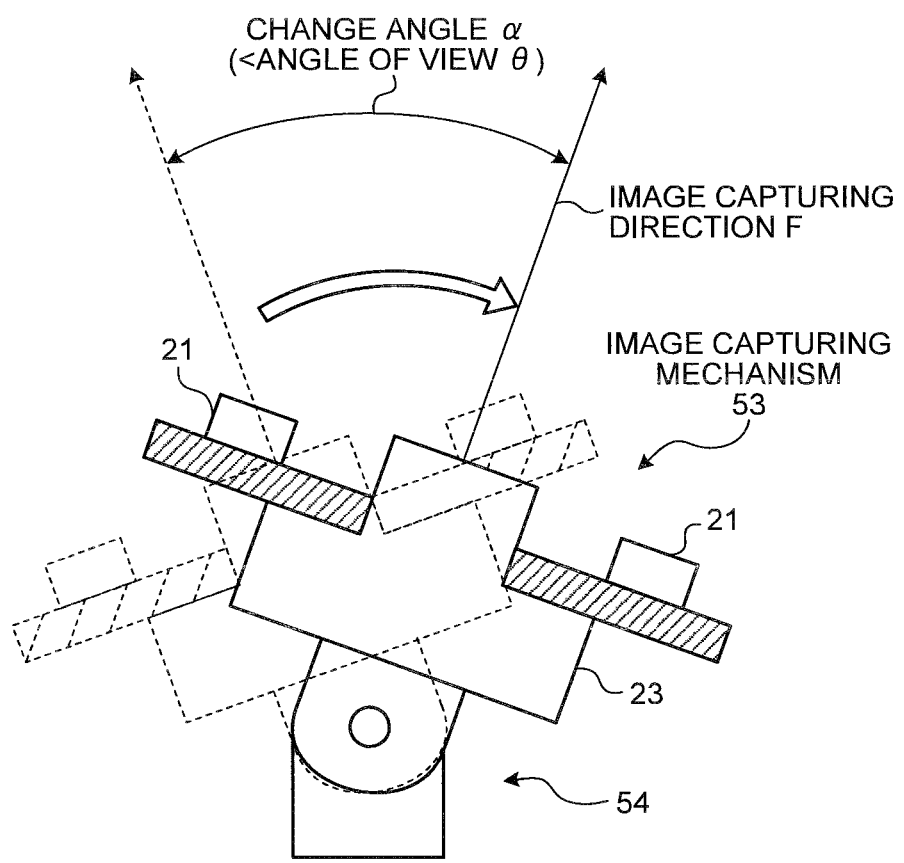
FIG. 17 is a schematic view exemplifying a state in which an image capturing direction of the capsule endoscope is changed by an operation of a drive unit.

Next, a change operation of the image capturing direction F performed by the drive unit 54 controlled by the control unit 55 as well as an in-vivo image capturing step and an image capturing direction change step in the in-vivo observing method according to the invention will be specifically explained by exemplifying a case in which in-vivo images of the subject 100 illuminated by the illumination light for the light emission time t are sequentially captured in the image capturing interval T as shown in FIG. 3 described above. FIG. 17 is a schematic view exemplifying a state in which the image capturing direction F of the capsule endoscope is changed by the operation of the drive unit 54.

As shown in FIG. 17, the image capturing mechanism 53 is rotated by the operation of the drive unit 54 and sequentially changes the image capturing direction F. In this case, the illuminating units 21 sequentially illuminate the image capturing field of view in the image capturing direction F which is changed (rotated) by the operation of the drive unit 54 only for the light emission time t in the image capturing interval T, and the imaging unit 23 sequentially captures images of the image capturing field of view in the image capturing direction F, i.e., in-vivo images of the subject 100 in the image capturing interval T.

The drive unit 54 rotates the image capturing mechanism 53 at the angular speed ω1 (<frame rate f×angle of view θ) in the image capturing interval T of the imaging unit 23 excluding the image capturing time of the in-vivo image based on the control of the drive control unit 55a described above and rotates the image capturing mechanism 53 at the angular speed ω2 (<angle of view θ÷(number of pixels m of one side×light emission time t)) during the period in which the imaging unit 23 captures in-vivo images in the image capturing interval T. In this case, as the image capturing mechanism 53 is rotated at the angular speeds ω1, ω2, the imaging unit 23 changes the image capturing direction F at the angular speed ω1 and changes the image capturing direction F at the angular speed ω2 particularly during the respective periods in which in-vivo images are captured.

When the drive unit 54 changes the image capturing direction F by rotating the image capturing mechanism 53 as described above, a change angle α [degree] of the image capturing direction F is less than the angle of view θ of the capsule endoscope 52 at all times as shown in FIG. 17. As a result, the image capturing field of view in the image capturing direction F overlaps at least a part of the field of view region of the image capturing field of view in the image capturing direction F after it is changed. The imaging unit 23 can securely capture a group of in-vivo images in which at least parts of image portions overlap between in-vivo images by sequentially capturing the in-vivo images while overlapping the field of view regions of the image capturing field of view as described above. When the imaging unit 23 time-sequentially captures a group of in-vivo images of the subject, the capsule endoscope 52 according to the fourth embodiment can securely obtain a group of continuous in-vivo images in which at least parts of image portions overlap between the in-vivo images adjacent to each other in time.

It is preferable to set the angular speed ω1 in the fourth embodiment equal to or less than one-half a multiplied value of the angle of view θ and the frame rate f likewise the third embodiment described above. The change angles α between the respective image capturing directions are equal to or less than one-half the angle of view θ at all times by setting the angular speed ω1 (≤frame rate f×angle of view θ÷2) as described above. As a result, the image capturing field of view in the image capturing direction F overlaps a half or more portion of the image capturing field of view in the image capturing direction F after it is changed. The capsule endoscope 52 can securely capture a group of in-vivo images in which half or more image portions overlap between the in-vivo images by overlapping the one-half or more field of view region between the respective image capturing fields of view as described above. Even when the center of rotation of the image capturing direction F does not agree with the center of the angle of view θ, the capsule endoscope 52 can more securely obtain a group of continuous in-vivo images in which at least parts of image portions overlap between the in-vivo images adjacent to each other in time.

As the image capturing mechanism 53 is rotated at the angular speed ω2 (<angle of view θ÷(number of pixels m of one side×light emission time t)), the capsule endoscope 42 changes the image capturing direction F at the angular speed ω2 during the respective periods in which it captures in-vivo images in the image capturing interval T as described above. Accordingly, an amount of offset of field of view of the image capturing field of view, which is offset following the image capturing direction F changed at the angular speed ω2 is less than one pixel of a light receiving surface of the imaging unit 23 at all times. As a result, the capsule endoscope 52 captures in-vivo images by changing the image capturing direction F at the angular speed ω2 during respective periods in which it captures in-vivo images likewise the third embodiment described above as well as can sequentially capture vivid in-vivo images whose image fluctuation is reduced even when the image capturing direction F is changed.

As explained above, in the fourth embodiment of the invention, the imaging unit for sequentially capturing in-vivo images and the drive unit for rotating the imaging unit are arranged in the capsule casing formed in a size which can be easily introduced into the body of a subject. The image capturing direction of the imaging unit is changed by causing the drive unit to rotate the imaging unit at the angular speed less than a multiplied value of the angle of view and the frame rate of the imaging unit. Accordingly, the change angle of the image capturing direction, which is changed by the operation of the drive unit, can be kept less than the angle of view of the imaging unit during the period of the image capturing interval in which in-vivo images are sequentially captured by the imaging unit so that at least parts of the field of view regions of the respective image capturing fields of view, which are offset by changing the image capturing direction, can be overlapped each other. As a result, there can be realized an in-vivo observing system and an in-vivo image acquisition device, which can securely obtain a group of continuous in-vivo images in which at least parts of image portions overlap between the in-vivo images adjacent to each other in time and can sequentially change the image capturing direction of the imaging unit even if the capsule casing is in a rest state to the subject as well as an in-vivo observing method, which observes inside of an organ of the subject by observing the group of the in-vivo images, likewise the third embodiment described above.

Uncaptured portions inside of an organ of the subject can be reduced as much as possible as well as a group of continuous in-vivo images can be obtained over approximately the entire region inside of the organ using the in-vivo observing system and the in-vivo image obtaining device according to the fourth embodiment. As a result, insides of organs such as a stomach and a large intestine of the subject can be entirely observed.

Further, during the period in which an in-vivo image of one frame is captured, the drive unit is caused to rotate the imaging unit at the angular speed less than a divided value obtained by dividing the angle of view of the imaging unit by a multiplied value of the number of pixels of one side of the in-vivo image and the image capturing time, and the image capturing direction of the imaging unit is changed at the angular speed. Accordingly, an amount of offset of field of view of the image capturing field of view of the imaging unit, which is offset by the change of the image capturing direction in the image capturing time of the in-vivo image, can be kept less than the amount of offset of one pixel of the in-vivo image. An image fluctuation of the in-vivo image of the image capturing field of view can be reduced to less than one pixel of the light receiving surface of the imaging unit or less than one pixel of a display system of an in-vivo image. As a result, even when an in-vivo image is captured as well as the image capturing direction is changed, vivid images whose image fluctuation is reduced can be sequentially captured.

Fifth Embodiment

Next, a fifth embodiment of the invention will be explained. In the first embodiment described above, the image capturing direction F of the capsule endoscope 2 is changed by changing the posture of the capsule endoscope 2 introduced into an organ of the subject by the external magnetic fields of the magnetic field generating unit 3. However, in the fifth embodiment, an endoscope device having a slender insertion portion which can be introduced into an organ of a subject is used, and an image capturing direction of an imaging unit is changed by curving a distal end of the insertion portion.

Figure 18:
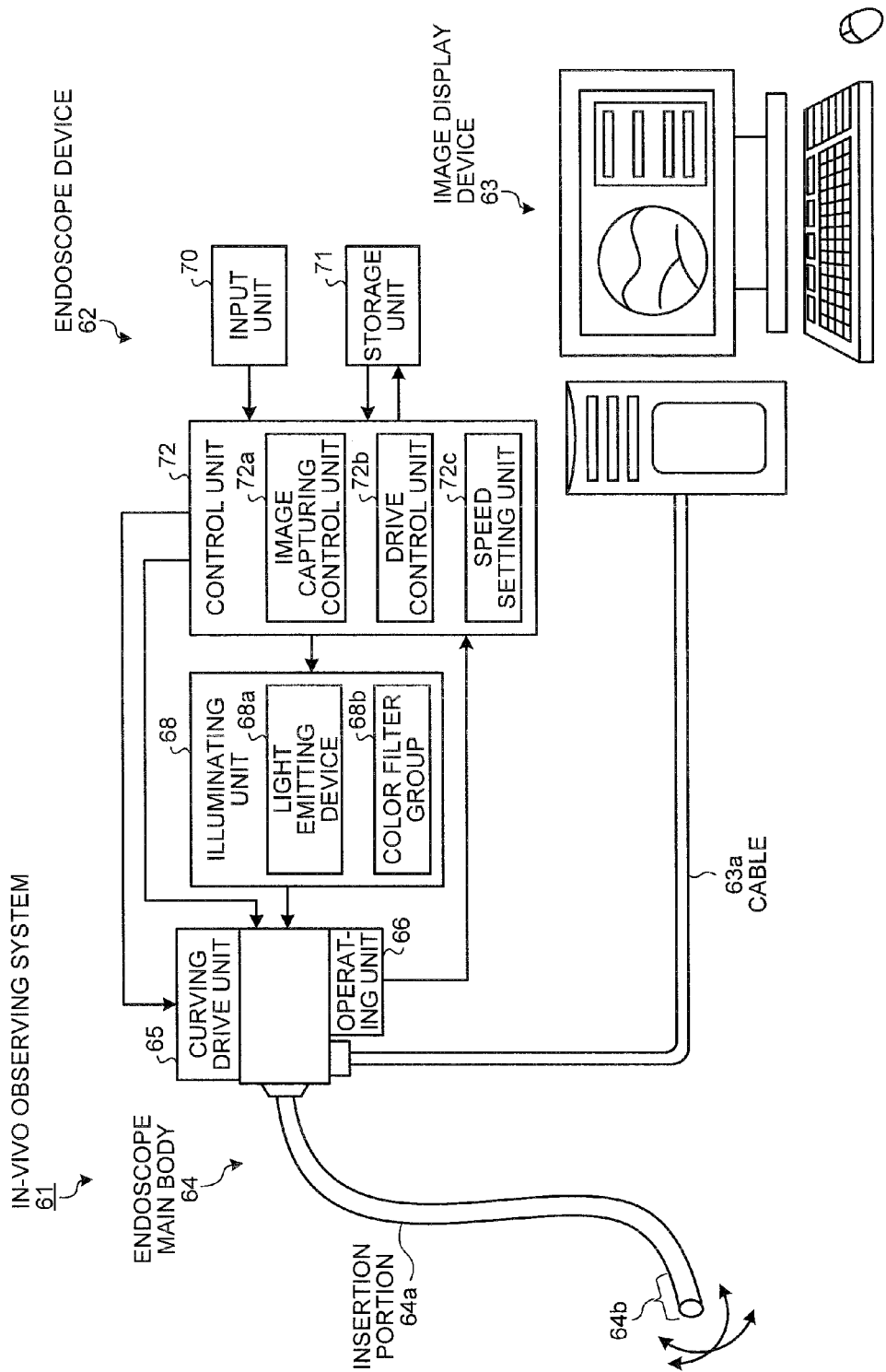
FIG. 18 is a block diagram schematically showing an arrangement example of an in-vivo observing system according to a fifth embodiment of the invention.
Figure 19:
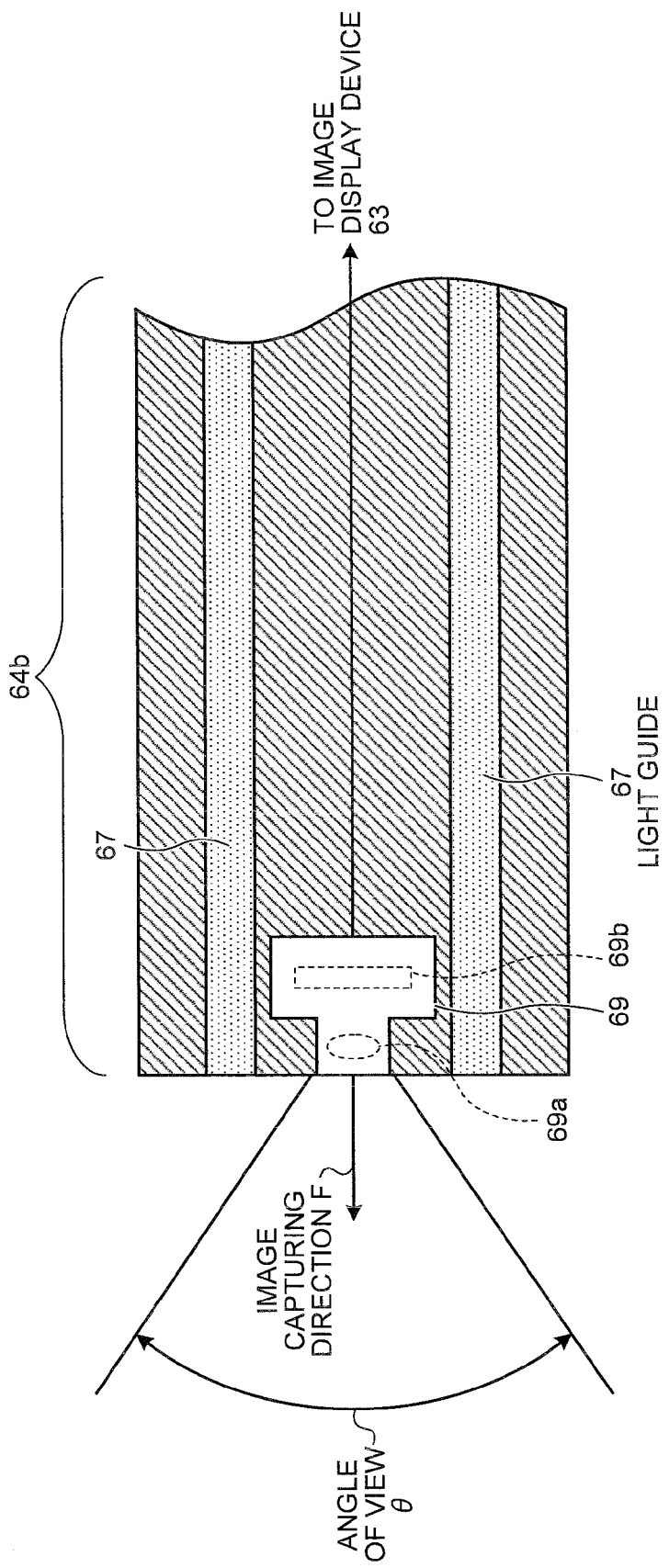
FIG. 19 is a schematic longitudinal sectional view exemplifying an internal arrangement of a distal end of an insertion portion of an endoscope device as an example of an in-vivo image acquisition device according to the fifth embodiment of the invention.

FIG. 18 is a block diagram schematically showing an arrangement example of an in-vivo observing system according to the fifth embodiment of the invention. FIG. 19 is a schematic longitudinal sectional view exemplifying an internal arrangement of the distal end of the insertion portion of the endoscope device as an example of an in-vivo image acquisition device according to the fifth embodiment of the invention. As shown in FIG. 18, an in-vivo observing system 61 according to the fifth embodiment includes an endoscope device 62 for sequentially obtaining in-vivo images of a subject and an image display device 63 for displaying a group of the in-vivo images obtained by the endoscope device 62. The endoscope device 62 includes an endoscope main body 64 having a slender insertion portion 64a which can be introduced into an organ of the subject, a curving drive unit 65 for curving a distal end 64b of the insertion portion 64a, an operating unit 66 for curving the distal end 64b, and an illuminating unit 68 for illuminating inside of an organ through the insertion portion 64a introduced into the organ of the subject. Further, the endoscope device 62 includes an input unit 70 for inputting various kinds of information, a storage unit 71 for storing various kinds of information such as a group of in-vivo images of the subject, and a control unit 72 for controlling the respective components of the endoscope device 62.

As described above, the endoscope main body 64 includes the slender insertion portion 64a which can be introduced into the organ of the subject. Further, as shown in FIG. 19, the endoscope main body 64 includes a light guide 67 such as an optical fiber and an imaging unit 69 in the insertion portion 64a. The insertion portion 64a is a flexible slender member which is introduced into the organ from a mouth, an anus, and the like of the subject. The insertion portion 64a curves the distal end 64b by the operation of the curving drive unit 65 to be described later.

The light guide 67 is realized using the optical fiber and the like and forms a light guide path in the insertion portion 64a. The light guide 67 transmits the illumination light emitted by the illuminating unit 68 from a proximal end side of the insertion portion 64a to the distal end 64b side thereof and guides the illumination light to the image capturing field of view (for example, inside of an organ of the subject) of the imaging unit 69.

The imaging unit 69 is fixedly arranged in the distal end 64b of the insertion portion 64a and captures in-vivo images of the subject illuminated by the illumination light introduced through the light guide 67, i.e., the illumination light of the illuminating unit 68. Specifically, the imaging unit 69 includes an optical system 69a such as a condenser lens and a solid image capturing device 69b such as a CMOS image sensor or a CCD. The optical system 69a collects the light reflected from inside of an organ of the subject (that is, the image capturing field of view of the imaging unit 69) illuminated by the illumination light of the illuminating unit 68 and focuses the image of the subject on a light receiving surface of the solid image capturing device 69b. The solid image capturing device 23b disposes the light receiving surface at the focus position of the optical system 23a, receives the light reflected from inside of the organ through the light receiving surface, and creates image data of in-vivo images by subjecting the reflected light received to a photoelectric conversion process.

As shown in FIG. 19, the imaging unit 69, which includes the optical system 69a and the solid image capturing device 69b, has an angle of view θ [degree] and an image capturing field of view prescribed by the angle of view θ in the image capturing direction F approximately parallel to a center axis CL in a longitudinal direction of the insertion portion 64a. In this case, the optical axis of the imaging unit 23 is approximately parallel to the center axis in the longitudinal direction of the insertion portion 64a and preferably approximately agrees therewith. Further, the imaging unit 69 sequentially captures in-vivo images inside of an organ positioned in the image capturing field of view at a predetermined frame rate f [frame/second]. The image data of the in-vivo images captured by the imaging unit 69 is sequentially transmitted to the image display device 63.

The curving drive unit 65 acts as a direction change unit for changing the image capturing direction F of the imaging unit 69 by curving the distal end 64b of the insertion portion 64a. Specifically, the curving drive unit 65 includes a cable (not shown) connected to the distal end 64b of the insertion portion 64a and an actuator (not shown) for curving the distal end 64b through the cable. The curving drive unit 65 curves the distal end 64b in a desired direction (up/down direction, right/left direction, and the like) in a space of an xyz coordinate system based on the control of the control unit 72. With this operation, the curving drive unit 65 changes the image capturing direction F of the imaging unit 69 in the distal end 64b.

The operating unit 66 is used to operate the curving drive unit 65 for changing the image capturing direction F of the imaging unit 69. The operating unit 66 is gripped by a user such as a doctor or a nurse who inputs instruction information for causing the curving drive unit 65 to curve the distal end 64b of the insertion portion 64a to the control unit 72.

The illuminating unit 68 radiates the illumination light to the image capturing field of view of the imaging unit 69 through the light guide 67 disposed in the insertion portion 64a described above and illuminates an image capturing field of view of the imaging unit 69. Specifically, the illuminating unit 68 includes a light emitting device 68a such as an LED and a color filter group 68b including color filters having a plurality of colors. The light emitting device 68a emits white light and causes the emitted white light to pass through the color filter group 68b. The color filter group 68b includes the color filters having the plurality of colors, for example, color filters having red, green, and blue colors which are the three primary colors of light (hereinafter, called RGB color filters) and sequentially changes the colors of the color filters through which the white light from the light emitting device 68a passes by rotating the RGB color filters. The color filter group 68b sequentially changes the white light from the light emitting device 68a to red light, green light, and blue light at a predetermined interval. The illuminating unit 68, which includes the light emitting device 68a and the color filter group 68b, radiates red, green, and blue illumination light to the image capturing field of view of the imaging unit 69 through the light guide 67 described above and sequentially illuminates the image capturing field of view of the imaging unit 69 by the red illumination light, the green illumination light, and the blue illumination light based on the control of the control unit 72.

The input unit 70 is realized using an input device such as a keyboard and a mouse and inputs various kinds of information to the control unit 72 in response to an input operation performed by the user such as the doctor or the nurse. The various kinds of information input to the control unit 72 by the input unit 70 are, for example, instruction information instructed to the control unit 72, information as to an imaging function of the imaging unit 69, and the like. The information as to the imaging function of the imaging unit 69 is in-vivo image capturing conditions and the like, for example, a frame rate and the angle of view θ at the time in-vivo images of the subject are sequentially captured, the number of pixels m of one side of an in-vivo image, a focusing position or an image capturing time of an optical system, and the like.

The storage unit 71 is realized using various storage mediums such as a RAM, an EEPROM, a flash memory or a hard disk for rewritably storing information. The storage unit 71 stores various kinds of information whose storage is instructed by the control unit 72 and sends the information whose read-out is instructed by the control unit 72 from the various stored information to the control unit 72. The information stored in the storage unit 71 are, for example, information as to the imaging function of the imaging unit 69 and the like input by the input unit 70.

The control unit 72 controls the respective operations of the respective units (the curving drive unit 65, the operating unit 66, the illuminating unit 68, the imaging unit 69, the input unit 70, and the storage unit 71) of the endoscope device 62 and controls signals which are input and output between the respective units. Specifically, the control unit 72 controls the light emission operation of the illumination light performed by the illuminating unit 68 and the in-vivo image capturing operation performed by the imaging unit. Further, the control unit 72 controls the operation of the curving drive unit 65 based on the instruction information input by the operating unit 66.

Figure 20:
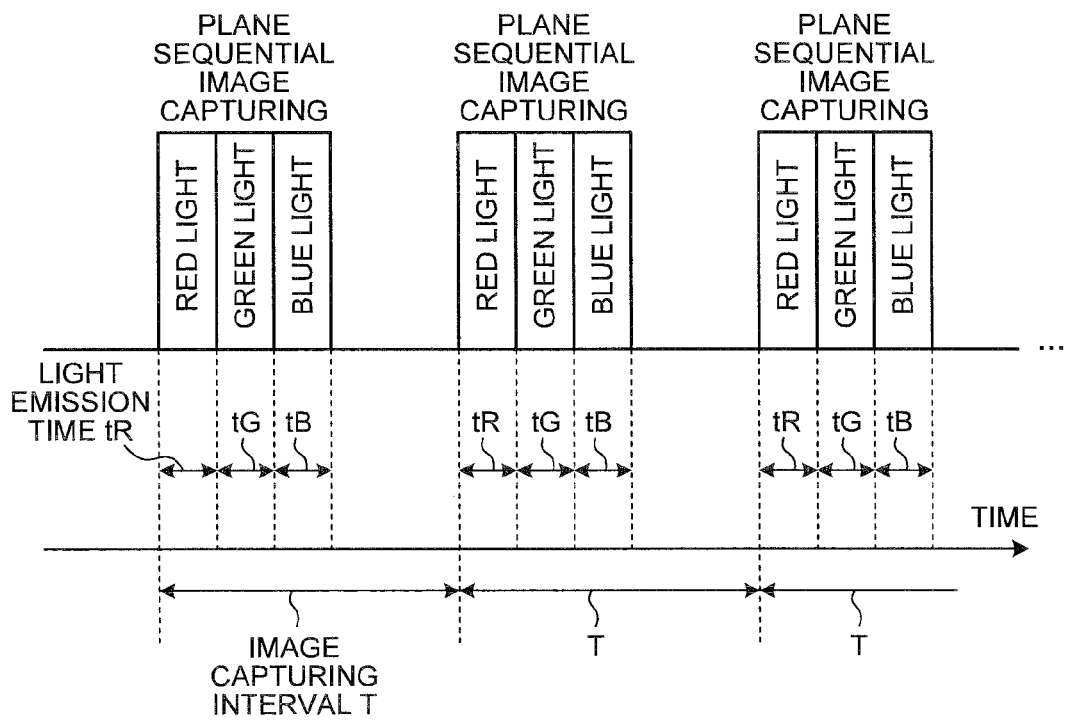
FIG. 20 is a schematic view exemplifying timings at which in-vivo images are captured by the endoscope device.

The control unit 72 includes an image capturing control unit 72a, a drive control unit 72b, and a speed setting unit 72c. The image capturing control unit 72a causes the illuminating unit 68 to sequentially output red illumination light, green illumination light, and blue illumination light at a predetermined interval and causes the imaging unit 69 to capture in-vivo images of the subject which are sequentially illuminated by the red illumination light, the green illumination light, and the blue illumination light (hereinafter, may be called red light, green light, and blue light) by a plane sequential method. Specifically, as shown in FIG. 20, the image capturing control unit 72a causes the illuminating unit 68 to sequentially output red light having a light emission time tR, green light having a light emission time tG, and blue light having a light emission time tB and causes the imaging unit 69 to capture in-vivo images of the subject sequentially illuminated by the red light, the green light, and the blue light in a predetermined image capturing interval T. In this case, the image capturing control unit 72a causes the illuminating unit 68 to repeatedly output the red light, the green light, and the blue light in a predetermined order (for example, in an order of the red light, the green light, the blue light) in the image capturing interval T and sequentially exposes the imaging unit 69 in synchronization with the respective light emission times tR, tG, tB of the illumination light.

An in-vivo image of one frame captured by the imaging unit 69 by the plane sequential method is formed by combining an in-vivo image of the subject illuminated by the red light having the light emission time tR (hereinafter, called a red spectral image), an in-vivo image of the subject illuminated by the green light having the light emission time tG (hereinafter, called a green spectral image), and an in-vivo image of the subject illuminated by the blue light having the light emission time tB (hereinafter, called a blue spectral image). That is, the image capturing time of the in-vivo image of the one frame of the imaging unit 69 is an added value obtained by adding the respective light emission times tR tG, tB of the red light, the green light, and the blue light. Further, as described above, the image capturing interval T of the imaging unit 69 is a time interval from a time at which the in-vivo image of the one frame starts to be captured to a time at which an in-vivo image of a next frame starts to be captured and includes the respective light emission times tR, tG, tB of the red light, the green light, and blue light and a light receiving time (exposure time) of the imaging unit 69, and the like.

The speed setting unit 72c previously obtains information as to the imaging function of the imaging unit 69 (the image capturing conditions such as the frame rate f, the angle of view θ, the pixel numbers m of one side of an in-vivo image, the light emission time, and the like) input by the input unit 70 and calculates an angular speed appropriately using the obtained information. The speed setting unit 72c sets the calculated angular speed as an angular speed when the distal end 64b of the insertion portion 64a is curved by the curving drive unit 65 described above (that is, when the image capturing direction F of the imaging unit 69 is changed). The drive control unit 72b causes the curving drive unit 65 to curve the distal end 64b of the insertion portion 64a at the angular speed set by the speed setting unit 72c to thereby cause the curving drive unit 65 to change the image capturing direction F of the imaging unit 69 in the distal end 64b. That is, the drive control unit 72b controls the image capturing direction F of the imaging unit 69 through the drive control of the curving drive unit 65.

The image display device 63 has a configuration like a work station and the like which obtain a group of in-vivo images of the subject sequentially captured by the imaging unit 69 described above by using the plane sequential method and displays the group of the in-vivo images of the subject. Specifically, the image display device 63 obtains a group of image data from the imaging unit 69 through a cable 63a and the like and creates a group of in-vivo images of the subject by subjecting the obtained group of the image data to a predetermined image processing. The image display device 63 includes a storage medium having a large capacity and stores the obtained group of the in-vivo images of the subject to the storage medium. Further, the image display device 63 has an input unit for inputting various kinds of information and displays the various kinds of information input by the input unit (for example, patient information and examination information of the subject) together with the in-vivo images of the subject. That is, the image display device 63 displays information useful for an endoscope examination to the subject. Further, the image display device 63 has a processing function for causing the user such as the doctor or the nurse to observe (examine) in-vivo images of the subject. The user can observe inside of an organ of the subject by causing the image display device 63 to display the group of the in-vivo images of the subject thereon.

Figure 21:
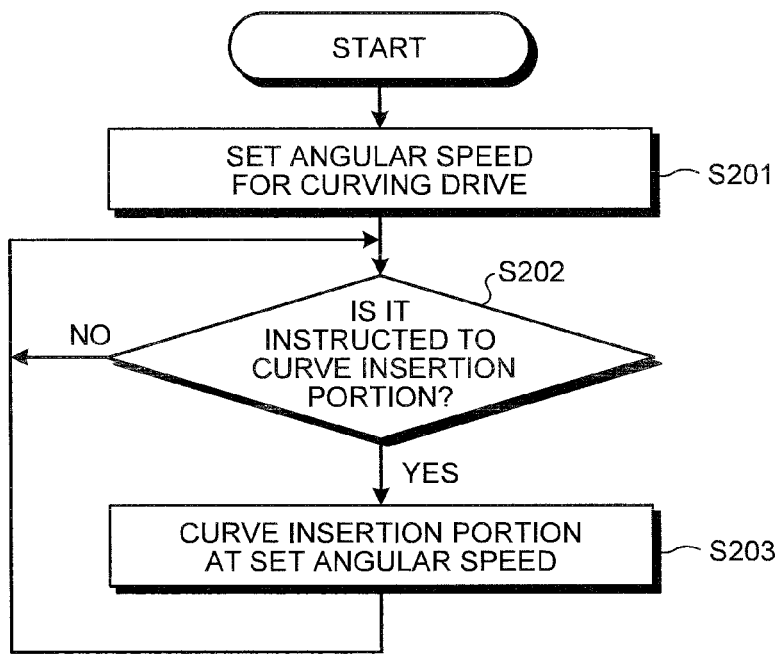
FIG. 21 is a flowchart exemplifying a process procedure of a control unit for controlling an image capturing direction of an imaging unit by the drive control of a curving drive unit.

Next, an operation of the control unit 72 for causing the curving drive unit 65 to change the image capturing direction F of the imaging unit 69 contained in the distal end 64b of the insertion portion 64a of the endoscope main body 64 will be explained. FIG. 21 is a flowchart exemplifying a process procedure of the control unit 72 for controlling the image capturing direction F of the imaging unit 69 by the drive control of the curving drive unit 65. The control unit 72 causes the curving drive unit to curve the distal end 64b of the insertion portion 64a introduced into an organ of the subject so that the curving drive unit 65 changes the image capturing direction F of the imaging unit 69 in the distal end 64b.

More specifically, as shown in FIG. 21, the control unit 72 first sets an angular speed at which the insertion portion 64a described above is curved (step S201). At step S201, the speed setting unit 72c obtains the information as to the imaging function of the imaging unit 69 input by the input unit 70, for example, the angle of view θ and the frame rate f of the imaging unit 69, the number of pixels m of one side of an in-vivo image, and the light emission times tR, tG, tB of the illumination lights, and sets the angular speed at which the insertion portion 64a is curved approximately using the obtained various kinds of information.

More specifically, the speed setting unit 72c calculates an angular speed ω1 [degree/second] less than a multiplied value obtained by multiplying the angle of view θ by the frame rate f and sets the calculated angular speed ω1 as an average angular speed when the distal end 64b is curved in the image capturing interval T described above. Further, the speed setting unit 72c calculates an angular speed ω2 [degree/second] less than a divided value obtained by dividing the angle of view θ by a multiplied value obtained by multiplying the number of pixels m of the one side of the in-vivo image by the light emission time tS of the illumination light and sets the calculated the angular speed ω2 as an average angular speed when the distal end 64b is curved in an image capturing time in the image capturing interval T described above. The light emission time tS is a total value obtained by adding the light emission time tR of the red light, the light emission time tG of the green light, and the light emission time tB of blue light described above. These angular speeds ω1, ω2 are stored to the storage unit 71 and read out by the control unit 72 when necessary.

Next, the control unit 72 determines whether or not it is instructed to curve the insertion portion 64a (step S202).

When instruction information for instructing to curve the insertion portion 64a is not input at step S202, the control unit 72 determines that it is not instructed to curve the insertion portion 64a (step S202, No) and repeats a process procedure at step S202. In contrast, when the instruction information for instructing to curve the insertion portion 64a is input by the operating unit 66, the control unit 72 determines that it is instructed to curve the insertion portion 64a (step S202, Yes) and causes the curving drive unit 65 to change the distal end 64b of the insertion portion 64a at the angular speeds ω1, ω2 set at step S201 described above (step S203).

At step S203, the drive control unit 72b controls the curving drive unit 65 so that it curves the distal end 64b of the insertion portion 64a at the angular speed ω1 described above (<frame rate f×angle of view θ) in the image capturing interval T of the imaging unit 69 excluding an image capturing time of an in-vivo image. The drive control unit 72b also controls the curving drive unit 65 so that it curves the distal end 64b of the insertion portion 64a at the angular speed ω2 described above (<angle of view θ÷(number of pixels m of one side×light emission time tS)) in the image capturing time of in-vivo images in the image capturing interval T of the imaging unit 69, i.e., in a period during which the imaging unit 69 captures in-vivo images by using the plane sequential method.

By controlling the curving drive unit 65 by the drive control unit 72b as described above, the curving drive unit 65 changes the image capturing direction F of the imaging unit 69, which is changed by curving the distal end 64b of the insertion portion 64a, at the angular speed ω1 described above in the image capturing interval T of the imaging unit 69 excluding the image capturing time of the in-vivo image and changes the image capturing direction F of the imaging unit 69, which is changed by curving the distal end 64b of the insertion portion 64a, at the angular speed ω2 described above during the period in which the imaging unit 69 captures in-vivo images by using the plane sequential method. Thereafter, the control unit 72 returns to step S202 described above and repeats process procedures at step S202 and subsequent steps.

Figure 22:
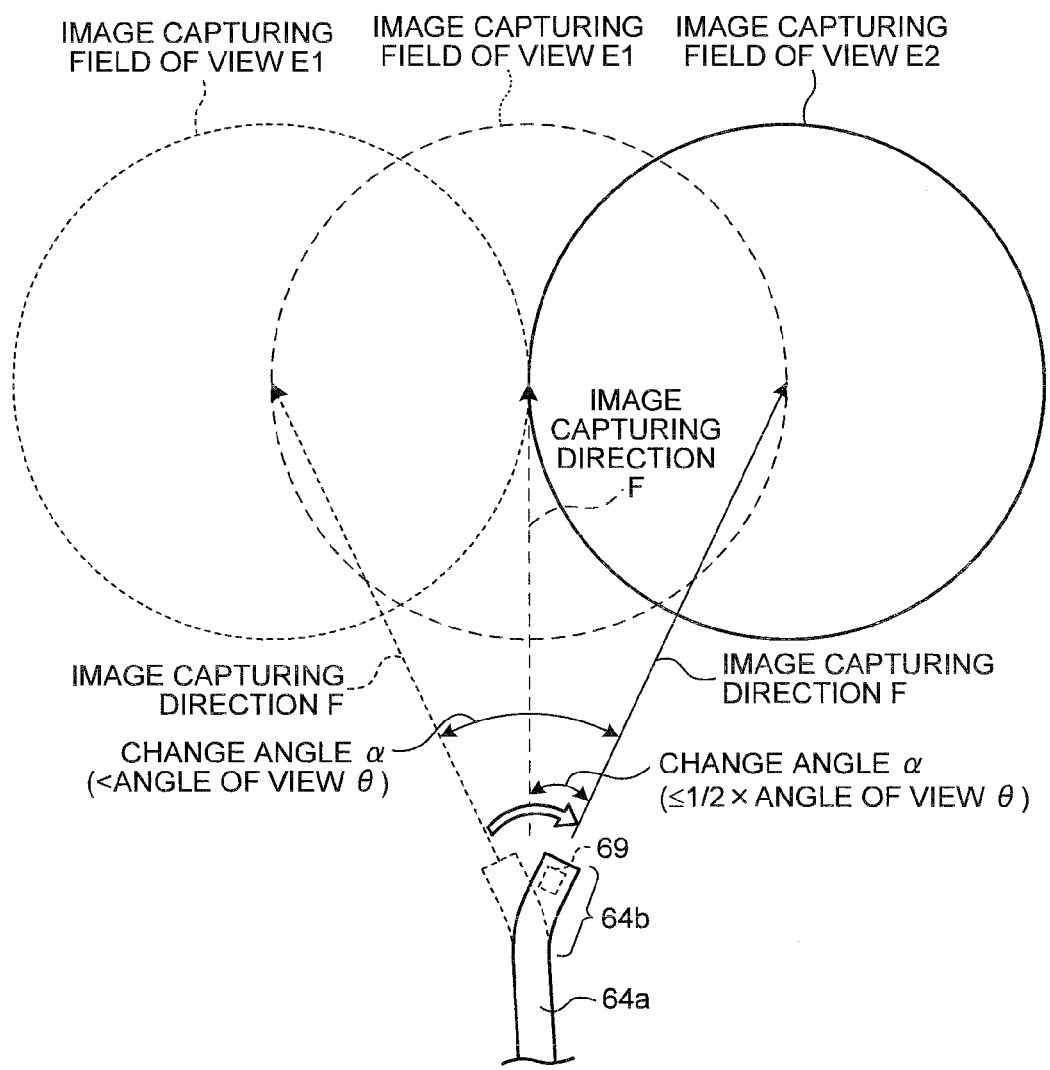
FIG. 22 is a schematic view exemplifying an image capturing state in which in-vivo images are sequentially captured by the imaging unit by a plane sequential method while changing the image capturing direction by curving the insertion portion.
Figure 23:
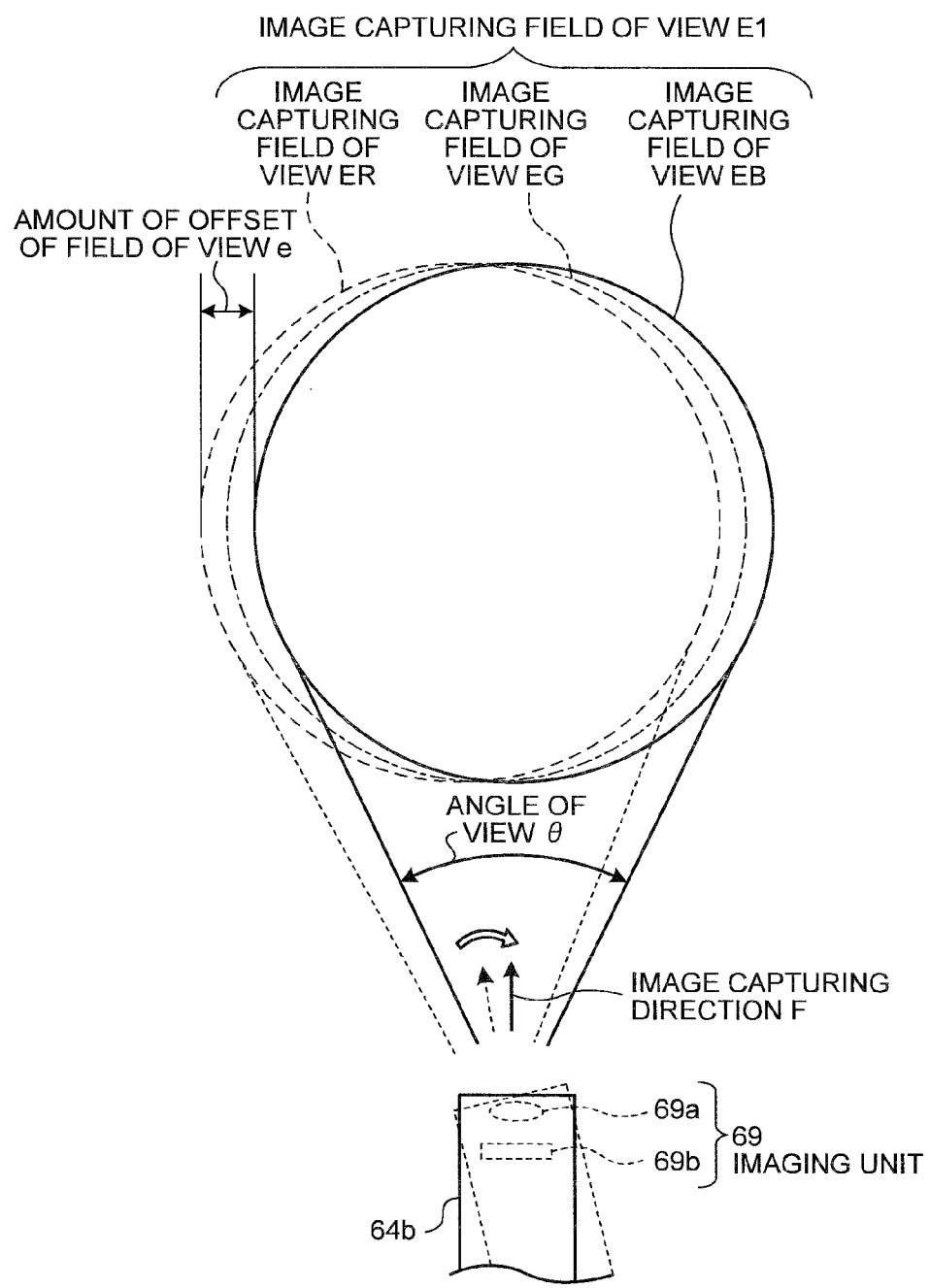
FIG. 23 is a schematic view exemplifying a state in which image capturing fields of view of respective spectral images are offset by changing an image capturing direction.

Next, a change operation of the image capturing direction F performed by the curving drive unit 65 controlled by the control unit 72 described above as well as an in-vivo image capturing step and an image capturing direction change step in the in-vivo observing method according to the invention will be specifically explained by exemplifying a case in which the imaging unit 69 in the distal end 64b of the insertion portion 64a introduced into an organ of the subject sequentially captures in-vivo images of two frames. FIG. 22 is a schematic view exemplifying an image capturing state in which in-vivo images are sequentially captured by using the plane sequential method while changing the image capturing direction by the imaging unit 69 by curving the distal end 64b of the insertion portion 64a. FIG. 23 is a schematic view exemplifying a state in which image capturing fields of view of respective spectral images are offset by changing the image capturing direction F.

In FIG. 22, image capturing fields of view E1, E2 are image capturing fields of view of the imaging unit 69, which catch inside of an organ of the subject, and prescribed by the angle of view ω as described above. In the image capturing fields of view E1, E2, the image capturing field of view E1 is an image capturing field of view corresponding to the in-vivo image of a first frame of the in-vivo images of the two frames which are sequentially captured by the imaging unit 69 by using the plane sequential method, and the image capturing field of view E2 is an image capturing field of view corresponding to the in-vivo image of a second frame of the in-vivo images of the two frames. Further, in FIG. 23, image capturing field of views ER, EG, EB are image capturing fields of view included in the image capturing field of view E1 of the in-vivo image of one frame. The image capturing field of view ER is an image capturing field of view of a red spectral image of the in-vivo image of the one frame, the image capturing field of view EG is an image capturing field of view of a green spectral image of the in-vivo image of the one frame, and the image capturing field of view EB is an image capturing field of view of a blue spectral image of the in-vivo image of the one frame.

As shown in FIG. 22, the insertion portion 64a curves the distal end 64b by the operation of the curving drive unit 65 controlled by the control unit 72 described above. The imaging unit 69 in the distal end 64b changes the image capturing direction F from the image capturing direction F of the image capturing field of view E1 (dotted arrow line) to the image capturing direction F of the image capturing field of view E2 (solid arrow line) by curving the distal end 64b as well as sequentially captures the respective in-vivo images of the image capturing field of views E1, E2 by using the plane sequential method.

The curving drive unit 65 curves the distal end 64b of the insertion portion 64a at the angular speed ω1 (<frame rate f×angle of view θ) in the image capturing interval T of the imaging unit 69 excluding the image capturing time of the in-vivo image and changes the distal end 64b at the angular speed ω2 (<angle of view θ÷(number of pixels m of one side×light emission time t S)) during the period in which the imaging unit 69 captures in-vivo images by using the plane sequential method in the image capturing interval T based on the control of the drive control unit 72b described above. In this case, the imaging unit 69 changes the image capturing direction F of the image capturing field of view E1 to the image capturing direction F of the image capturing field of view E2 at the angular speed ω1 and more particularly changes the image capturing direction F at the angular speed ω2 during the respective periods in which the in-vivo images of the image capturing field of views E1, E2 are captured by curving the distal end 64b at the angular speeds ω1, ω2.

When the curving drive unit 65 changes the image capturing direction F by curving the distal end 64b as described above, a change angle α [degree] of the image capturing direction F is less than the angle of view θ of the imaging unit 69 at all times as shown in FIG. 22. As a result, the image capturing field of view E1 in the image capturing direction F overlaps at least parts of the field of view regions of the image capturing field of view E2 in the image capturing direction F after it is changed. The imaging unit 69 can securely capture a group of in-vivo images in which at least parts of image portions overlap between in-vivo images by sequentially capturing the respective in-vivo images of the image capturing fields of view E1, E2 while overlapping the field of view regions as described above. When the imaging unit 69 time-sequentially captures a group of in-vivo images of the subject, it can securely obtain a group of continuous in-vivo images in which at least parts of image portions overlap between the in-vivo images adjacent to each other in time.

It is preferable to set the angular speed ω1 in the fifth embodiment equal to or less than one-half a multiplied value of the angle of view θ and the frame rate f likewise the first embodiment described above. The change angle α between the image capturing direction F of the image capturing field of view E1 and the image capturing direction F of the image capturing field of view E2 is equal to or less than the angle of view θ at all times as shown in FIG. 22 by setting the angular speed ω1 (≤=frame rate f×angle of view θ÷2) as described above. As a result, the image capturing field of view E1 in the image capturing direction F overlaps half or more parts of the image capturing field of view E2 in the image capturing direction F after it is changed. The imaging unit 69 can securely capture a group of in-vivo images in which half or more parts of image portions overlap between the in-vivo images by sequentially capturing the respective in-vivo images of the image capturing fields of view E1, E2 in which half or more parts of the field of view regions overlap as described above. Even when the center of rotation of the image capturing direction F does not agree with the center of the angle of view θ, the imaging unit 69 can more securely obtain a group of continuous in-vivo images in which at least parts of image portions overlap between the in-vivo images adjacent to each other in time.

As described above, the imaging unit 69 changes the image capturing direction F at the angular speed ω2 (<angle of view θ÷(number of pixels m of one side×light emission time t S)) as the distal end 64b is curved at the angular speed ω2 during the respective periods in which the in-vivo images of the image capturing fields of views E1, E2 in the image capturing interval T are sequentially captured by the plane sequential method. In this case, the image capturing fields of views E1, E2 of the in-vivo images captured by the plane sequential method are offset in a certain amount as the image capturing direction F is changed.

Specifically, as shown in FIG. 23, the image capturing fields of view ER, EG, EB included in the image capturing field of view E of the in-vivo image captured by using the plane sequential method are offset in an amount e as the image capturing direction F is changed. The image capturing direction F of the imaging unit 69 is changed (rotated) at the angular speed ω2 in the image capturing time of the in-vivo images, i.e., in the light emission time tS of the respective illumination light as described above. Accordingly, the amounts of offset of the field of view e of the capturing fields of view ER, EG, EB, which are offset in the image capturing time of the in-vivo images as the image capturing direction F is changed, are an amount of offset less than one pixel of the in-vivo image (i.e., the in-vivo image captured by the plane sequential method) corresponding to the image capturing field of view E1 including the image capturing fields of view ER, EG, EB.

As a result, when the number of pixels of the one side of the imaging unit 69 is equal to or less than the number of pixels of the one side of a display system of an in-vivo image, image fluctuations of the red spectral image, the green spectral image, and the blue spectral image caused by the offset of the image capturing fields of view ER, EG, EB, i.e., the color fluctuation of the above in-vivo images of the plane sequential method formed by combining the red spectral image, the green spectral image, and the blue spectral image can be reduced to less than one pixel of a light receiving surface of the imaging unit 69, whereas when the number of pixels of the one side of the imaging unit 69 exceeds the number of pixels of the one side of the display system of in-vivo images, the color fluctuation can be reduced to less than one pixel of the display system of the in-vivo image. As described above, the imaging unit 69 captures in-vivo images by changing the image capturing direction F at the angular speed ω2 described above. Further, even when the image capturing direction F is changed, the imaging unit 69 can reduce the color fluctuation of the in-vivo images captured by using the plane sequential method and can sequentially capture vivid in-vivo images by the plane sequential method. An effect of reducing the color fluctuation of the in-vivo images can be also obtained as to an image capturing field of view E2 of a next frame in which in-vivo images are captured next to the image capturing field of view E1 likewise.

As explained above, in the fifth embodiment of the invention, the imaging unit is fixedly disposed to the distal end of the slender insertion portion introduced into the subject, the distal end of the insertion portion is curved at the angular speed less than a multiplied value of the angle of view and the frame rate of the imaging unit, and the image capturing direction of the imaging unit is changed at the angular speed. Accordingly, the change angle of the image capturing direction of the imaging unit, which is changed as the distal end is curved, can be kept less than the angle of view of the imaging unit during the period of the image capturing interval of the in-vivo images which are sequentially captured by the imaging unit. Thus, at least parts of the view field regions of the respective image capturing fields of view, which are offset as the image capturing direction is changed, can be overlapped each other. As a result, there can be realized an in-vivo observing system and an in-vivo image obtaining device, which can securely obtain a group of continuous in-vivo images in which at least parts of image portions overlap between the in-vivo images adjacent to each other in time when a group of in-vivo images of the subject is sequentially captured as well as an in-vivo observing method of observing inside of an organ of the subject through observation of the group of the in-vivo images.

By using the in-vivo observing system and the in-vivo image obtaining device according to the fifth embodiment, uncaptured portions inside of an organ of the subject can be reduced as much as possible, and a group of continuous in-vivo images can be obtained over approximately the entire region inside of the organ. As a result, insides of organs such as a stomach and a large intestine of the subject can be entirely observed.

Further, during the period in which an in-vivo image of one frame is captured by using the plane sequential method, the distal end of the insertion portion is curved at the angular speed less than a divided value obtained by dividing the angle of view of the imaging unit by a multiplied value of the number of pixels of one side of the in-vivo image and the image capturing time, and the image capturing direction of the imaging unit is changed at the angular speed. Accordingly, amounts of offset of field of view of the image capturing fields of view of the respective spectral images for forming in-vivo images by the plane sequential method can be kept less than the amount of offset of one pixel of the in-vivo image so that an image fluctuation of the respective spectral images can be reduced to less than one pixel of the light receiving surface of the imaging unit or less than one pixel of the display system of the in-vivo image. As a result, even when in-vivo images are captured by using the plane sequential method and the image capturing direction is changed, the color fluctuation of the in-vivo images caused by an image fluctuation of the respective spectral images can be reduced, and vivid in-vivo images can be sequentially captured by the plane sequential method.

In the first and second embodiments of the invention, the magnetization direction of the magnet 28 contained in the capsule endoscope is caused to agree with the image capturing direction F of the imaging unit 23. However, the invention is not limited thereto, and the magnetization direction of the magnet 28 may not be caused to agree with the image capturing direction F of the imaging unit 23 by magnetizing the magnet 28 in, for example, a direction which tilts at a predetermined angle to the longitudinal direction of the casing 20 of the capsule casing 20 or a diameter direction of the casing 20. In this case, an amount of change of the image capturing direction F, which changes following the external magnetic fields of the magnetic field generating unit 3, is equal to or less than an amount of change of the image capturing direction F of the capsule endoscope in which the magnetization direction of the magnet 28 is caused to agree with the image capturing direction F of the imaging unit 23. Accordingly, when a posture of the capsule endoscope is controlled by the same condition as the angular speed condition of the magnetic field direction at the time the image capturing direction F of the imaging unit 23, in which the magnetization direction of the magnet 28 is caused to agree with the image capturing direction F of the imaging unit 23, is changed, even if the magnetization direction of the magnet 28 is not caused to agree with the image capturing direction F of the imaging unit 23, continuous in-vivo images can be securely obtained and an image fluctuation of in-vivo images can be reduced likewise when they are caused to agree with each other.

Further, in the second embodiment of the invention, the plurality of types of the light emission time of the illumination light are set, and the amount of light emission of the illumination light is changed by switching the plurality of types of the light emission time in the predetermined order. However, the invention is not limited thereto, and the control unit 36 of the capsule endoscope 32 may adjust an amount of light emission of preferable illumination light or a light emission time of illumination light depending on a relative distance between the imaging unit 23 and an inner wall of an organ based on the luminance information and the like of an in-vivo image. In this case, the control unit 33 outside of the subject may find the light emission time of the illumination light based on the luminance information and the like of the in-vivo image obtained from the capsule endoscope 32 and set the angular speed $\omega 2$ in the magnetic field directions based on the found light emission time.

Further, in the first to third embodiments of the invention, the information necessary to calculate the angular speeds $\omega 1$, $\omega 2$, such as the frame rate f of in-vivo images and the image capturing conditions and the like, is input by the input unit 8. However, the invention is not limited thereto, and the information necessary to calculate the angular speeds $\omega 1$, $\omega 2$, such as the frame rate f, the image capturing conditions such as the light emission time, the number of types n of the image capturing conditions, the number of pixels m of one side of an in-vivo image, and the like may be obtained from the information, for example, the receiving time of in-vivo images, the luminance information of the in-vivo image, and the like, which are received from the capsule endoscope by the receiving unit 6.

Further, in the second embodiment of the invention, the four types of the image capturing conditions (image capturing conditions of the light emission times t1 to t4) having different light emission times of illumination light are set as the plurality of the image capturing conditions. However, the image capturing conditions are not limited thereto and may be image capturing conditions classified by two or more types of light emission times. Further, a plurality of types of image capturing conditions classified by each light emission wavelength of the illumination light may be set in place of the light emission times, a plurality of types of image capturing conditions classified by each focus position of an optical system, i.e., each focus position of the imaging unit may be set, and a plurality of types of image capturing conditions classified by an appropriate combination of the light emission times of the illumination light, the light emission wavelengths, the focus positions, and the like may be set. In any of the cases, it is sufficient to change the magnetic field directions of the external magnetic fields described above so that at least parts of image portions overlap between the in-vivo images of the same type of the image capturing conditions.

Figure 24:
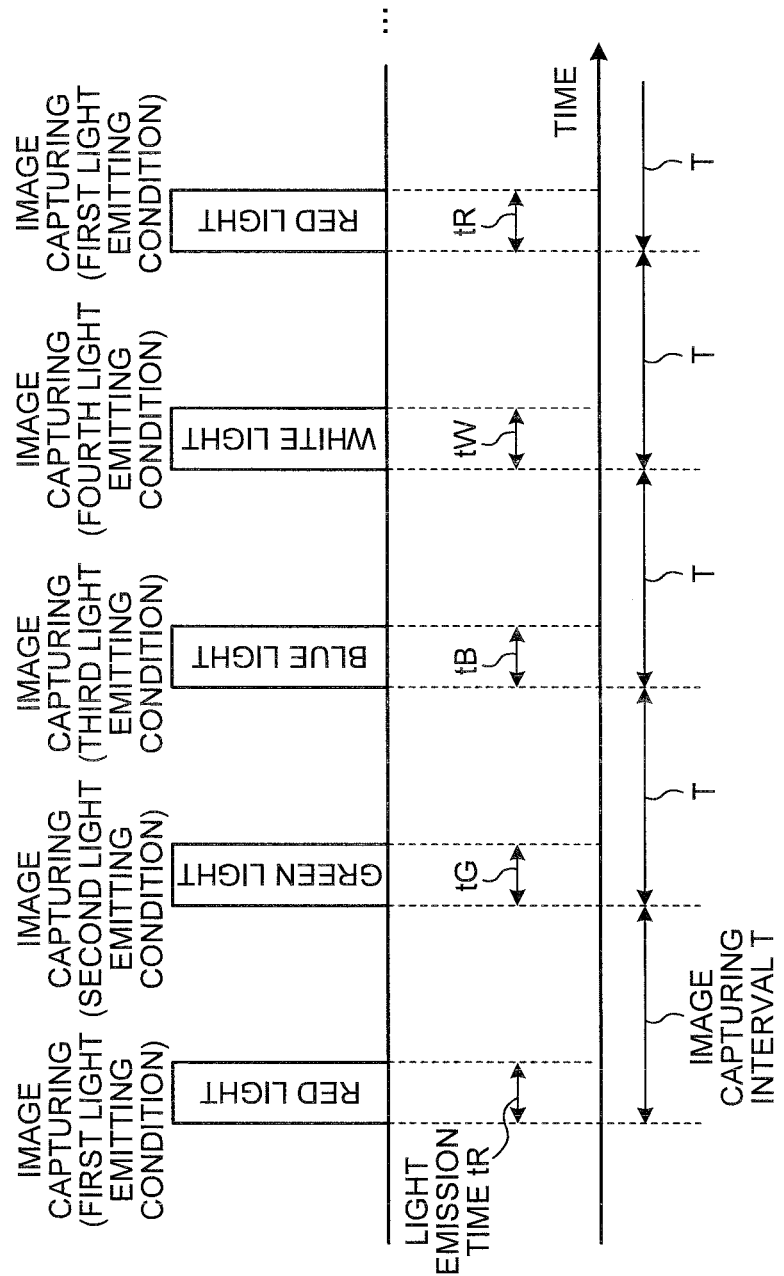
FIG. 24 is a schematic view exemplifying timings at which in-vivo images are captured by a capsule endoscope for switching a light emission wavelength of illumination light.

When, for example, the plurality of types of light emission wavelengths are set as the image capturing conditions, it is sufficient to switch the plurality of types of light emission wavelengths (i.e., light emission colors of illumination light) in a predetermined order in each image capturing interval T of in-vivo images as shown in FIG. 24. In this case, the control unit 36 of the capsule endoscope 32 may repeatedly switch the red light of the light emission time tR, the green light of the light emission time tG, the blue light of the light emission time tB, and the white light of a light emission time tW in a predetermined order as the illumination light of the plurality of type of emission wavelengths. Further, it is sufficient for the control unit 33 outside of the subject to cause the magnetic field generating unit 3 to change the magnetic field directions of the external magnetic fields so that at least parts of image portions overlap between respective in-vivo images of the same light emission wavelength band (or the same received light wavelength band) in a group of in-vivo images captured by the capsule endoscope 32.

Further, in the second embodiment of the invention, the order, in which the light emission time sequentially increases from the light emission time t1 which is the minimum time of the four types of the light emission times t1 to t4, is set as a switching order of one cycle. However, the invention is not limited thereto, and an order in which the light emission time-sequentially decrease or an order in which the light emission time repeats an increase or a decrease of the light emission time may be set as the switching order of the one cycle as long as the switching order of the one cycle is fixed.

Further, in the first to fifth embodiments of the invention, the angular speeds $\omega 1$, $\omega 2$ are calculated by the speed setting unit. However, the invention is not limited thereto, and the angular speeds $\omega 1$, $\omega 2$ previously set according to the image capturing conditions may be input to the control unit outside of the subject through the input unit, or the angular speeds $\omega 1$, $\omega 2$ may be previously set to the capsule endoscope whose image capturing direction is changed or to the control unit of the endoscope device.

Further, in the second embodiment of the invention, the angular speed $\omega 2$ is calculated using the light emission time t4 which is the maximum value of the light emission times t1 to t4. However, the invention is not limited thereto. A plurality of types of angular speeds $\omega 2$ may be calculated according to a plurality of types of light emission times, and the angular speed $\omega 2$ may be switched according to a light emission time. For example, when illumination light of the light emission time t1 is emitted, it is sufficient to change the image capturing direction F at the angular speed $\omega 2$ calculated using the light emission time t1; when illumination light of the light emission time t2 is emitted, it is sufficient to change the image capturing direction F at the angular speed $\omega 2$ calculated using the light emission time t2; when illumination light of the light emission time t3 is emitted, it is sufficient to change the image capturing direction F at the angular speed $\omega 2$ calculated using the light emission time t3; and when illumination light of the light emission time t4 is emitted, it is sufficient to change the image capturing direction F at the angular speed $\omega 2$ calculated using the light emission time t4. With this operation, since the angular speed $\omega 2$ in the magnetic field directions can be set to an optimum value according to an image capturing time, the angular speed $\omega 2$ can be reduced when the image capturing time is long and further the angular speed $\omega 2$ can be increased when the image capturing time is short. As a result, an image fluctuation of an in-vivo image can be efficiently reduced in a short time.

Further, in the third embodiment of the invention, the image capturing direction F is relatively changed with respect to the subject 100 by rotating the bed 43 on which the subject 100 is placed. However, the invention is not limited thereto, and the image capturing direction F may be relatively changed with respect to the subject 100 by changing a body position of the subject 100 including the capsule endoscope in an organ by an examiner or the subject 100 itself. In this case, the image capturing direction F of the capsule endoscope in the subject 100 may be relatively changed with respect to the subject 100 by appropriately changing the body position of the subject 100 to a lying position, a standing position, and a sitting position using a bed 101 as shown in FIG. 25. In this case, it is sufficient to change the body position of the subject 100 at the angular speed $\omega 1$ in the image capturing interval T of an in-vivo image, and it is sufficient to change the body position of the subject 100 at the angular speed $\omega 2$ in the image capturing time of an in-vivo image (for example, the light emission time t).

In the third embodiment of the invention, the bed 43 is used as the placing unit on which the subject 100 is placed. However, the invention is not limited thereto, and the placing unit may be a reclining seat on which the subject 100 can be placed so that his or her posture (body position) can be changed. In this case, it is sufficient to change the body position of the subject 100 by driving the reclining seat (driving, for example, a back) at the angular speed $\omega 1$ in the image capturing interval T of the in-vivo image, and it is sufficient to change the body position of the subject 100 by driving the reclining seat at the angular speed $\omega 2$ in the image capturing time of the in-vivo image.

Further, in the first to fifth embodiments of the invention, although the information necessary to calculate the angular speeds $\omega 1$, $\omega 2$, such as the frame rate f, the angle of view $\theta$, the number of types n of the image capturing conditions, the image capturing condition, and the like, is input through the input unit 8, the invention is not limited thereto. The information may be previously set according to a specification of the capsule endoscope. At the time, the angular speed $\omega 1$ is determined based on the maximum value of the frame rate f set to the capsule endoscope, and the angular speed $\omega 2$ is determined based on the maximum value of the of the light emission time t set to the capsule endoscope. Accordingly, even when the image capturing condition is changed, an image can be securely obtained.

Further, in the first to fifth embodiments of the invention, although angles are changed at a constant speed by the angular speeds $\omega 1$, $\omega 2$ set to the speed setting unit according to the input to the input unit 8, the invention is not limited thereto, and they may be changed depending on an amount of input to the input unit 8. At the time, the angular speeds $\omega 1$, $\omega 2$ are set to the speed setting unit as the maximum values of the angular speeds. Accordingly, since a change speed in an observation direction can be changed by an intention of an operator, an image can be securely obtained as well as an operability can be improved.

Further, in the first and fifth embodiments of the invention, the direction of the imaging unit is changed at the angular speed $\omega 1$ during the period of the image capturing interval T excluding the image capturing time of the in-vivo image and at the angular speed $\omega 2$ during the period in which images are captured. However, the invention is not limited thereto, and an image can be securely obtained by setting a smaller value of the angular speeds $\omega 1$, $\omega 2$ as the angular speeds and changing the direction of the imaging unit by the set angular speed. As described above, the smaller value of the angular speeds $\omega 1$, $\omega 2$ may be set as the maximum value of the angular speeds.

Further, in the first to fifth embodiments of the invention, a group of continuous in-vivo images, in which at least parts of image portions overlap, can be securely obtained by prescribing the angular speeds. However, the invention is not limited thereto, and an image can be securely obtained by prescribing an amount of change of angle. Specifically, a moving amount setting unit is provided in place of the speed setting unit described above, and an amount of change $\phi$ of angle during the period of the image capturing interval T excluding the image capturing time of the in-vivo image is set to the moving amount setting unit. At the time, the amount of change $\phi$ of the angle is set equal to or less than the angle of view $\theta$. After the period, in which in-vivo images are captured, is finished, an angle of the imaging unit is changed by the amount of change $\phi$ (<angle of view $\theta$) during the period of the image capturing interval T excluding the image capturing time of the in-vivo image. It is sufficient to keep a posture of the imaging unit thereafter until a period in which a next in-vivo image is captured is finished. The same operation/working effect as that of the case in which the angular speeds are prescribed can be obtained as described above also in this case.

The in-vivo observing system provided with the moving amount setting unit finds the period (timing) in which an in-vivo image is captured and the direction of the imaging unit is changed during the period of the image capturing interval T excluding the image capturing time of the in-vivo image. However, the invention is not limited thereto. Even in a state that image capture timing is not detected, a group of continuous and overlapping in-vivo images can be securely obtained by keeping the direction of the imaging unit during a period of a sum of the image capturing interval T and the time in which the in-vivo image is captured after an angle of the imaging unit is changed by the amount of change $\phi$.

After the direction of the imaging unit is kept for a predetermined time, the imaging unit may be controlled so that the angle thereof is changed by an angle which is smaller than a multiplied value obtained by multiplying the predetermined time, the frame rate f, and the angle of view $\theta$ as well as smaller than the angle of view $\theta$. In this case, since an average angular speed of the direction of the imaging unit is equal to or less than the angular speed $\omega 1$ at all times, a group of overlapping and continuous in-vivo images can be obtained.

Further, in the first embodiment of the invention, the angular speed $\omega 2$ is set less than the divided value obtained by dividing the angle of view $\theta$ by the multiplied value of the number of pixels m of one side of the imaging unit 23 or the display unit 9 and the light emission time t. However, the invention is not limited thereto, and the angular speed $\omega 2$ may be set less than a divided value obtained by dividing the minimum value of angles captured in the respective pixels of the imaging unit 23 or angles displayed on the respective pixels of the display unit 9 by the light emission t. In this case, even when the angles captured in the respective pixels of the imaging unit 23 and the angles displayed on the respective pixels of the display unit 9 are different, an image fluctuation can be reduced in all the pixels with a result that in-vivo images can be captured more vividly.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An in-vivo observing system for observing inside of a subject, comprising:
an illuminating unit configured to illuminate inside of the subject by illumination light;
an imaging unit configured to sequentially capture in-vivo images of the subject illuminated by the illumination light;
a direction change unit configured to change an image capturing direction of the imaging unit; and
a control unit configured to control the direction change unit to set an angular difference in the imaging capturing direction less than an angle of view of the imaging unit when the imaging unit captures two continuous in-vivo images while causing the direction change unit to change the image capturing direction, wherein
the control unit causes the direction change unit to change the image capturing direction of the imaging unit at an angular speed equal to or less than one-half a multiplied value of the frame rate and the angle of view of the imaging unit.

2. The in-vivo observing system according to claim 1, wherein each time the imaging unit captures an in-vivo image, the control unit causes the direction change unit to keep the image capturing direction for a predetermined time and then change the image capturing direction of the imaging unit by an angle smaller than a value obtained by multiplying the predetermined time and a frame rate and the angle of view of the imaging unit as well as smaller than the angle of view.

3. The in-vivo observing system according to claim 1, wherein the imaging unit sequentially captures in-vivo images of the su claim 1 itching a plurality of types of image capturing conditions in a predetermined order, and the control unit causes the direction change unit to change the image capturing direction of the imaging unit at the angular speed less than a divided value obtained by dividing the multiplied value of the frame rate and the angle of view of the imaging unit by the number of types of the image capturing conditions.

4. The in-vivo observing system according to claim 1, further comprising a capsule casing that fixedly arranges therein the illuminating unit and the imaging unit, wherein
the capsule casing is a casing of a capsule endoscope which is introduced into a body of the subject and obtains a group of in-vivo images of the subject by the imaging unit, and
the direction change unit changes the image capturing direction of the imaging unit by changing a relative direction of the capsule endoscope to the subject.

5. The in-vivo observing system according to claim 1, further comprising a capsule casing that contains the illuminating unit, the imaging unit, the direction change unit, and the control unit and that is introduced into a body of the subject, wherein
the direction change unit changes the image capturing direction of the imaging unit by relatively rotating the imaging unit with respect to the capsule casing, and
the control unit controls an angular speed of the imaging unit rotated by the direction change unit.

6. The in-vivo observing system according to claim 1, further comprising a slender insertion portion configured to fixedly dispose the imaging unit in a distal end thereof and to be introduced into a body of the subject from the distal end side, wherein
the direction change unit changes the image capturing direction of the imaging unit by curving the distal end of the insertion portion, and
the control unit controls an angular speed of the distal end of the insertion portion which is curved by the direction change unit.

7. The in-vivo observing system according to claim 2, wherein the control unit comprises a detecting unit configured to detect image capture timing and an image capturing time at and in which the imaging unit captures the in-vivo image and causes the direction change unit to keep the image capturing direction of the imaging unit for a predetermined time at the image capture timing detected by the detecting unit.

8. The in-vivo observing system according to claim 4, further comprising a placing unit on which the subject is placed, wherein
the capsule endoscope has a center of gravity at a position deviated from a center of the capsule casing and keeps a specific posture prescribed by the center of gravity in a liquid introduced into the body of the subject,
the direction change unit changes a relative image capturing direction of the imaging unit with respect to the subject by rotating the placing unit to relatively change the posture of the subject with respect to the capsule endoscope which keeps the specific posture, and
the control unit controls an angular speed of the placing unit rotated by the direction change unit.

9. An in-vivo observing system for observing inside of a subject, comprising:
an illuminating unit configured to illuminate inside of the subject by illumination light;
an imaging unit configured to sequentially capture in-vivo images of the subject illuminated by the illumination light;
a direction change unit configured to change an image capturing direction of the imaging unit; and
a control unit configured to control the direction change unit to set an angular difference in the imaging capturing direction less than an angle of view of the imaging unit when the imaging unit captures two continuous in-vivo images while causing the direction change unit to change the image capturing direction, wherein,
the control unit causes the direction change unit to change the image capturing direction of the imaging unit at an angular speed less than a multiplied value of the frame rate and the angle of view of the imaging unit,
when the number of pixels of one side of a light receiving surface of the imaging unit is equal to or less than the number of pixels of one side of a display system of the in-vivo image corresponding to the one side of the light receiving surface of the imaging unit, the control unit causes the direction change unit to change the image capturing direction of the imaging unit at an angular speed less than a divided value obtained by dividing a minimum value of angles that allow the imaging unit to capture the in-vivo image in the respective pixels of the light receiving surface of the imaging unit by an image capturing time of the imaging unit, and
when the number of pixels of the one side of the light receiving surface of the imaging unit exceeds the number of pixels of the one side of the display system, the control unit causes the direction change unit to change the image capturing direction of the imaging unit at an angular speed less than a divided value obtained by dividing a minimum value of angles that allow the display system to display the in-vivo image on the respective pixels of the display system by the image capturing time of the imaging unit.

10. The in-vivo observing system according to claim 9, wherein
the image capturing time has the same value as a light emission time of the illumination light, and
the illuminating unit changes the light emission time of the illumination light depending on an image capturing condition of the in-vivo image.

11. An in-vivo observing system for observing inside of a subject, comprising:
an illuminating unit configured to illuminate inside of the subject by illumination light;
an imaging unit configured to sequentially capture in-vivo images of the subject illuminated by the illumination light;
a direction change unit configured to change an image capturing direction of the imaging unit;
a control unit configured to control the direction change unit to set an angular difference in the imaging capturing direction less than an angle of view of the imaging unit when the imaging unit captures two continuous in-vivo images while causing the direction change unit to change the image capturing direction; and
an input unit configured to receive an amount of change of the image capturing direction of the imaging unit, wherein
the control unit causes the direction change unit to change the image capturing direction of the imaging unit at an angular speed less than a multiplied value of the frame rate and the angle of view of the imaging unit,
the control unit changes the angular speed depending on to an amount of input to the input unit and controls the direction change unit so that the angular speed is maximized when the amount of input is maximized, and
the maximum value of the angular speed is less than the multiplied value of the frame rate and the angle of view of the imaging unit.

12. An in-vivo observing system for observing inside of a subject, comprising:
an illuminating unit configured to illuminate inside of the subject by illumination light;
an imaging unit configured to sequentially capture in-vivo images of the subject illuminated by the illumination light;
a direction change unit configured to change an image capturing direction of the imaging unit; and
a control unit configured to control the direction change unit to set an angular difference in the imaging capturing direction less than an angle of view of the imaging unit when the imaging unit captures two continuous in-vivo images while causing the direction change unit to change the image capturing direction; and
an input unit configured to receive an amount of change of the image capturing direction of the imaging unit, wherein
the control unit causes the direction change unit to change the image capturing direction of the imaging unit at an angular speed less than a multiplied value of the frame rate and the angle of view of the imaging unit, and
the control unit changes the angular speed depending on an amount of input to the input unit.

13. An in-vivo observing system for observing inside of a subject, comprising:
an illuminating unit configured to illuminate inside of the subject by illumination light;
an imaging unit configured to sequentially capture in-vivo images of the subject illuminated by the illumination light;
a direction change unit configured to change an image capturing direction of the imaging unit;
a control unit configured to control the direction change unit to set an angular difference in the imaging capturing direction less than an angle of view of the imaging unit when the imaging unit captures two continuous in-vivo images while causing the direction change unit to change the image capturing direction; and
a capsule casing that fixedly arranges therein the illuminating unit and the imaging unit, wherein
the capsule casing is a casing of a capsule endoscope which is introduced into a body of the subject and obtains a group of in-vivo images of the subject by the imaging unit,
the direction change unit changes the image capturing direction of the imaging unit by changing a relative direction of the capsule endoscope to the subject,
the capsule casing comprises a magnetic substance that changes a posture of the capsule endoscope following external magnetic field,
the direction change unit applies the external magnetic field to the magnetic substance in a body of the subject from outside of the body and changes a posture of the capsule endoscope as well as the image capturing direction of the imaging unit by changing magnetic field direction of the applied external magnetic field, and
the control unit controls an angular speed in the magnetic field direction of the external magnetic field which is changed by the direction change unit.

14. An in-vivo observing method of observing inside of an organ of a subject by observing in-vivo images of the subject captured by an in-vivo image acquisition device introduced into the organ of the subject comprising:
a first image capturing step of capturing a first in-vivo image of the subject by the in-vivo image acquisition device;
an image capturing direction change step of changing an image capturing direction of the in-vivo image acquisition device; and
a second image capturing step of capturing a second in-vivo image of the subject by the in-vivo image acquisition device whose image capturing direction has been changed at the image capturing direction change step, wherein
at the image capturing direction change step, the image capturing direction of the in-vivo image acquisition device is changed at an angular speed less than a multiplied value of the frame rate and the angle of view of the imaging unit so that the first in-vivo image and the second in-vivo image have image portions overlapping each other.

15. The in-vivo observing method according to claim 14, further comprising:
a liquid introduction step of introducing a liquid inside of an organ of the subject; and
a capsule introduction step of introducing a capsule endoscope as the in-vivo image acquisition device which keeps a specific floating posture in the liquid into the organ of the subject, wherein
at the image capturing direction change step, an image capturing direction of the capsule endoscope is changed by changing a posture of the subject.

16. The in-vivo observing method according to claim 15, wherein, at the image capturing direction change step, the image capturing direction of the capsule endoscope is changed by changing the posture of the subject at an angular speed less than a multiplied value of a frame rate of the capsule endoscope and an angle of view of the capsule endoscope.

17. The in-vivo observing method according to claim 15, wherein, at the image capturing direction change step, the image capturing direction of the capsule endoscope is changed by changing the posture of the subject at an angular speed less than a divided value obtained dividing a minimum value of angles that allow a solid image capturing device to capture the in-vivo image in respective pixels of a light receiving surface of the solid image capturing device contained in the capsule endoscope by an image capturing time of the capsule endoscope.

* * * * *